United States Patent
Slingluff et al.

(10) Patent No.: US 6,660,276 B1
(45) Date of Patent: *Dec. 9, 2003

(54) PEPTIDES RECOGNIZED BY MELANOMA-SPECIFIC CYTOTOXIC LYMPHOCYTES, AND USES THEREFOR

(75) Inventors: Craig L. Slingluff, Charlottesville, VA (US); Victor M. Engelhard, Charlottesville, VA (US); Donald F. Hunt, Charlottesville, VA (US); Jeffrey Shabanowitz, Charlottesville, VA (US); Andrea L. Cox, Charlottesville, VA (US)

(73) Assignee: The University of Virginia Patent Foundation, Charlottesville, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/234,784

(22) Filed: Apr. 29, 1994

Related U.S. Application Data

(63) Continuation-in-part of application No. 08/197,399, filed on Feb. 16, 1994, now abandoned.

(51) Int. Cl.[7] ............................................. A61K 39/00
(52) U.S. Cl. ............................ 424/277.1; 424/185.1; 514/14; 514/15
(58) Field of Search ............................ 424/186.1, 193.1, 424/195.11, 196.11, 198.1, 199.1, 277.1, 185.1; 514/14–15

(56) References Cited

U.S. PATENT DOCUMENTS 5,010,175 A    4/1991  Rutter et al.
5,196,512 A  * 3/1993  Bianchi
5,472,856 A  * 12/1995 Harris
5,487,974 A  * 1/1996  Boon-Falleur
5,610,031 A  * 3/1997  Burgeson
5,844,075 A    12/1998 Kawakami et al.
5,874,560 A    2/1999  Kawakami et al.

FOREIGN PATENT DOCUMENTS

WO         8600991     2/1986
WO         8606487    11/1986
WO       WO9423067   10/1994

OTHER PUBLICATIONS

Jaeger et al. 1996 Int. J. Cancer 66:162.*
Boon et al 1994 Ann. Rev. Immunol. 12:337.*

(List continued on next page.)

*Primary Examiner*—Sheela Huff
(74) *Attorney, Agent, or Firm*—Iver P. Cooper

(57) ABSTRACT

The instant disclosure identifies and synthesizes peptide residues initially isolated from a melanoma cell line. The peptides are capable of reconstituting an epitope recognized by tumor specific CTL. Some of the sequences are homologous with proteins identified as pMEL17, tyrosinase and cofilin. The present invention provides for the treatment of melanoma patients using synthetic peptides that reconstitute epitopes for melanoma specific CTL. In another embodiment the peptides are used as vaccines for imparting immunity. Alternatively, in one embodiment the peptides may be used to bind to antigen presenting cells in a method for providing specific antigenic stimulation of CTL. The instant invention provides CTL cell lines capable of recognizing reconstituted HLA-A2.1 epitopes and their use in methods of adoptive immunotherapy. The invention additionally provides for genes encoding for peptides capable of reconstituting epitopes recognized by tumor specific CTL and their use as vaccines in the prevention and management of melanoma. A splitter is also disclosed to identify active peptides.

12 Claims, 13 Drawing Sheets

OTHER PUBLICATIONS

Brichard et al. 1993 J. Exp. Med. 178:489.*
Slingluff et al. 1993 J of Immunol. 150:2955.*
Adema et al. 1993 Am. J. of Pathology 143:1579.*
Maketa et al. 1986 Haptens and Carriers in Handbook of Immunology vol. 1: Immunochemistry Ed. by Herzenberg et al Blackwell Scientic Pub. 1986.*
Karin et al. J. Exp. Med. 180:227, 1994.*
Sakai et al. PNAS 85:8608 1988.*
Martin et al. J. Immunology 146:1359, 1992.*
Cox et al., *Identification of a Peptide Recognized by Five Melanoma–Specific Human Cytotoxic T Cell Lines,* SCIENCE, vol. 264, pp. 716–719, Apr. 29, 1994.
Maresh et al., *Cloning and Expression of the Gene for the Melanoma–Associated ME20 Antigen,* DNA and Cell Biology, vol. 13, No. 2, pp. 87–95, Feb. 1994.
Salgaller et al., *Generation of specific anti–melanoma reactivity by stimulation of human tumor–infiltrating lymphocytes with MAGE–1 synthetic peptide,* Cancer Immunol. Immunother., vol. 39, No. 2, pp. 105–116, Aug. 1994.
Storkus et al., *Identification of Human Melanoma Peptides Recognized by Class I Restricted Tumor Infiltrating T Lymphocytes,* Journal of Immunology, vol. 151, No. 7, pp. 3719–3727, Oct. 1993.
Huang, et al. *Packed–Capillary Liquid Chromatography/Ion–Spray Tandem Mass Spectrometry Determination of Biomolecules,* Analytical Chemistry, vol. 63, No. 7, pp. 732–739, Apr. 1, 1991.
Arpino, et al. *Supercritical Fluid Chromatography–Mass Spectrometry Coupling,* Trac, Trends in Analytical Chemistry, vol. 6, No. 3, pp. 69–73, 1987.
Anichini, et al., *Melanoma Cells and Normal Melanocytes Share Antigens Recognized by HLA–A2–restricted Cytotoxic T Cell Clones from Melanoma Patients,* J. Exp. Med., vol. 177, pp. 989–998, Apr. 1993.
Bakker, et al., *Melanocyte Lineage–specific Antigen gp100 is Recognized by Melanoma–derived Tumor–infiltrating Lymphocytes,* The Journal of Experimental Medicine, vol. 179, pp. 1005–1009, Mar. 1994.
Bednarek, et al., *The Minimum Peptide Epitope From the Influenza Virus Matrix Protein,* The Journal of Immunology, vol. 147, No. 12, pp. 4047–4053, Dec. 15, 1991.
Bertoletti, et al., *Definition of a Minimal Optimal Cytotoxic T–Cell Epitope within the Hepatitis B Virus Nucleocapsid Protein,* Journal of Virology, vol. 67, No. 4, pp. 2376–2380, Apr. 1993.
Bouchard, et al., *Induction of Pigmentation in Mouse Fibroblasts by Expression of Human Tyrosinase cDNA,* J. Exp. Med., vol. 169, pp. 2029–2042, Jun. 1989.
Chen, et al., *Naturally Processed Peptides Longer than Nine Amino Acid Residues Bind to the Class I MHC Molecule HLA–A2.1 with High Affinity and in Different Conformations,* Journal of Immunology, vol. 152, No. 6, pp. 2874–2881, Mar. 15, 1994.
Coulie, et al., *A New Gene Coding for a Differentiation Antigen Recognized by Autologous Cytolytic T Lymphocytes on HLA–A2 Melanomas,* J. Exp. Med., vol. 180, pp. 35–42, Jul. 1994.
Darrow, et al., *The Role of HLA Class I Antigens in Recognition of Melanoma Cells by Tumor–Specific Cytotoxic T Lymphocytes,* The Journal of Immunology, vol. 142, No. 9, pp. 3329–3335, 1989.

Falk, et al., *Identification of Naturally Processed Viral Nonapeptides Allows Their Quantification in Infected Cells and Suggests an Allele–specific T Cell Epitope Forecast,* J. Exp. Med., vol. 174, pp. 425–434, Aug. 1991.
Finn, et al., *Tumor–rejection antigens recognized by T lymphocytes,* Current Opinion in Immunology, vol. 5, pp. 701–708, 1993.
Henderson, et al., *Direct Identification of an Endogenous Peptide Recognized by Multiple HLA–A2.1–specific cytotoxic T cells,* Proc. Natl. Acad. Sci. USA, vol. 90, pp. 10275–10279, Nov. 1993.
Hom, et al., *Common Expression of Melanoma–Tumor–Associated Antigens Recognized by Human Tumor Infiltrating Lymphocytes: Analysis by Human Lymphocyte Antigen Restriction,* Journal of Immunotherapy, vol. 10, pp. 153–164, 1991.
Huczko, et al., *Characteristics of Endogenous Peptides Eluted from the Class I MHC Molecule HLA–B7 Determined by Mass Spectrometry and Computer Modeling,* Journal of Immunology, vol. 151, No. 5, pp. 2572–2587, Sep. 1, 1993.
Hunt, et al., *Characterization of Peptides Bound to the Class I MHC Molecule HLA–A2.1 by Mass Spectrometry,* SCIENCE, vol. 255, pp. 1261–1263, Mar. 6, 1992.
Kawakami, et al., *Identification of a human melanoma antigen recognized by tumor–infiltrating lymphocytes associated with in vivo tumor rejection,* Proc. Natl. Acad. Sci. USA, vol. 91, pp. 6458–6462, Jul. 1994.
Kawakami, et al., *Identification of the Immunodominant Peptides of the MART–1 Human Melanoma Antigen Recognized by the Majority of HLA–A2–restricted Tumor Infiltrating Lymphocytes,* The Journal of Experimental Medicine, vol. 180, pp. 347–352, Jul. 1994.
Kawakami, et al., *Recognition by Tumor–Infiltrating Lymphocytes in HLA–A2.1–Transfected Melanomas,* The Journal of Immunology, vol. 148, No. 2, pp. 638–643, Jan. 15, 1992.
Kwon, et al., *A Melanocyte–specific Complementary DNA Clone Whose Expression is Inducible by Melanotropin and Isobutylmethyl Xanthine,* Mol. Biol. Med., vol. 4, pp. 339–355, 1987.
Kwon, et al., *A melanocyte–specific gene, Pmel 17, maps near the silver coat color locus on mouse chromosome 10 and is in a syntenic region on human chromosome 12,* Proc. Natl. Acad. Sci., USA, vol. 88, pp. 9228–9232, Oct. 1991.
Kwon, et al., *Isolation and sequence of a cDNA clone for human tyrosinase that maps at the mouse c–albino locus,* Proc. Natl. Acad. Sci. USA, vol. 84, pp. 7473–7477, Nov. 1987.
Madden, et al., *The Antigenic Identity of Peptide–MHC Complexes: A Comparison of the Conformations of Five Viral Peptides Presented by HLA–A2,* Cell, vol. 75, pp. 693–708, Nov. 19, 1993.
Mandelbolm, et al., *CTL induction by a tumour–associated antigen octapeptide derived from a murine lund carcinoma,* NATURE, vol. 369, pp. 67–71, May 5, 1994.
Oetting, et al., *Molecular Analysis of an Extended Family with Type IA (Tyrosinase–Negative) Oculocutaneous Albinism,* The Journal of Investigative Dermatology, vol. 97, pp. 15–19, Jul. 1991.
Ohkura, et al., *Purification of Hamster Melanoma Tyrosinases and Structural Studies of Their Asparagine–Linked Sugar Chains,* Archives of Biochemistry and Biophysics, vol. 235, No. 1, pp. 63–77, 1984.

Ruppert, et al., *Prominent Role of Secondary Anchor Residues in Peptide Binding to HLA–A2.1 Molecules,* CELL, vol. 74, pp. 929–937, Sep. 10, 1993.

Traversari, et al, *A Nonapeptide Encoded by Human Gene MAGE–1 is Recognized on HLA–A1 by Cytolytic T Lymphocytes Directed against Tumor Antigen MZ2–E,* J. Exp. Med., vol. 176, pp. 1453–1457, Nov. 1992.

Udaka, et al., *A Naturally Occurring Peptide Recognized by Alloreactive CD8+ Cytotoxic T Lymphocytes in Association with a Class I MHC Protein,* CELL, vol. 69, pp. 989–998, Jun. 12, 1992.

Van Bleek, et al., *Isolation of an endogenously processed immunodominant viral peptide from the class I $H–2K^b$ molecule,* NATURE, vol. 348, pp. 213–216, Nov. 15, 1990.

Wolfel, et al., *Two tyrosinase nonapeptides recognized on HLA–A2 melanomas by autologous cytolytic T lymphocytes,* Eur. J. Immunol., vol. 24, pp. 759–763, 1994.

Wolfel, et al., *Lysis of Human Melanoma Cells by Autologous Cytolytic T Cell Clones,* J. Exp. Med., vol. 170, pp. 797–810, Sep. 1989.

Geysen, et al., *Strategies for epitope analysis using peptide synthesis,* Journal of Immunological Methods, vol. 102, pp. 259–274, 1987.

Geysen, et al., *Chemistry of Antibody Binding to a Protein,* SCIENCE, vol. 235, pp. 1184–1190, Mar. 6, 1987.

Geysen, et al., *Use of peptide synthesis to probe viral antigens for epitopes to a resolution of a single amino acid,* Proc. Natl. Acad. Sci. USA, vol. 81, pp. 3998–4002, Jul. 1984.

Houghten, Richard, *General method for the rapid solid-–phase synthesis of large numbers of peptides: Specificity of antigen–antibody interaction at the level of individual amino acids,* Proc. Natl. Acad. Sci. USA., vol. 82, pp. 5131–5135, Aug. 1985.

Slingluff, et al., *Human Cytotoxic T Cells Specific for Autologous Melanoma Cells: Successful Generation From Lymph Node Cells in Seven Consecutive Cases,* Journal of National Cancer Institute, vol. 80, No. 13, pp. 1016–1026, Sep. 7, 1988.

Slingluff, et al., *Human T Cells Specifically Activated Against Autologous Malignant Melanoma,* Arch. Surg., vol. 122, pp. 1407–1411, Dec. 1987.

Slingluff, et al., *Melanoma–Specific Cytotoxic T Cells Generated from Peripheral Blood Lymphocytes,* Ann. Sur., vol. 210, No. 2, pp. 194–202, Aug. 1989.

Townsend, et al., *Antigen Recognition by Class I–Restricted T Lymphocytes,* Ann. Rev. Immunol., vol. 7, pp. 601–624, 1989.

\* cited by examiner

PEPTIDES RECOGNIZED BY MELANOMA-SPECIFIC CYTOTOXIC LYMPHOCYTES, AND USES THEREFOR

This application is a continuation-in-part of Ser. No. 08/197,399 filed Feb. 16, 1994, now abandoned, hereby incorporated by reference in its entirety.

BACKGROUND OF THE INVENTION

1. Field of the Invention

The present invention is directed to peptides that, in association with Class I MHC molecules, form epitopes recognized by cytotoxic T-cells specific for human melanoma.

2. Description of the Background Art

Melanoma affects 30,000 new patients per year in the United States. It is a cancer manifested by the unabated proliferation of melanocytes. Eighty percent of melanoma patients are diagnosed during their productive years between the ages of 25 and 65. The incidence of melanoma is rapidly increasing, in 1935 the lifetime risk of developing melanoma was 1:1,500 individuals, at present, the risk has risen to 1:105. It is believed that by the year 2000 the risk of developing melanoma will increase to about 1:70 to 1:90. Early diagnosis and treatment of this disease is crucial. Once a primary tumor becomes metastatic the disease is almost uniformly fatal.

Cytotoxic lymphocyte (CTL) response has been shown to be an important host defense against malignant cells, Rock et al. J. Immunol., (1993), 150:1244. Several studies have shown the presence of shared epitopes located on melanoma cells. CTLs respond to these epitopes, however, until now the epitopes were structurally undefined. Anti-tumor CTL may be generated in vitro by the restimulation of lymphocytes isolated from melanoma patients using autologous tumor cells, Slingluff et al., Arch. Surg., (1987), 122:1407. Adoptive transfer of tumor stimulated CTL has been associated with some tumor regressions, Rosenberg et al., N. Eng. J. Med., (1988), 319:1676. However, cure is rarely mediated by this approach. Alternate approaches to augmenting the T-cell response to melanoma have been the use of tumor vaccines, also known as specific active immunotherapy.

Attempts to maintain competent levels of immunity against emergent tumor cell clones using melanoma antigen have done little to affect the natural course of the disease. This may be due, in part, to the non-specific nature of antigen used. Thus, there is a need to provide specific tumor antigens or haptens for the purpose of enhancing the immune response to tumors cells in order to effectively vaccinate against tumor cell growth.

It is believed that understanding the cellular immune response to melanoma may be important in defining new therapies; however, optimizing those therapies will depend on identification of the specific epitopes recognized by those CTL.

Lymphocytes isolated from patients having melanoma, when stimulated in vitro with recombinant interleukin-2 (rIL-2) and autologous melanoma cells, develop a melanoma specific cytotoxic response, Vose et al., Nature, (1982), 296:359; Knuth et al., Proc. Natl. Acad. USA, (1984), 81:3511; Slingluff et al., Arch. Surg., (1987), 122:1407; Darrow et al., Cancer, (1988), 62:84; Slingluff et al., J. Natl. Cancer Inst., (1988), 80:1016; Slingluff et al., Ann. Surg., (1989), 210:194; Muul et al., J. Immunol., (1987), 138:989; Anichini et al., Int. J. Cancer, (1985), 35:683. Melanoma specific effector lymphocytes are, by the majority, $CD8^+$ cytotoxic T lymphocytes (CTL) that are restricted by class I Major Histocompatibility Complex (MHC) molecules, Vose et al; Slingluff et al (1988), supra, Hersey et al., Cancer Immunol. Immunother., (1986), 22:15. These characteristics are present whether CTL have been generated from peripheral blood lymphocytes (PBL), Vose et al.; Slingluff et al. (1989), supra; Van den Eynde et al., Int. J. Cancer, (1989), 44:634, lymph node cells, or tumor infiltrating lymphocytes. Evidence that the CTL response to human melanoma is restricted by class I MHC molecules includes demonstration of cross-reactivity for allogenic melanoma cells that share a restricting class I MHC molecule with the autologous tumor. The HLA-A2 molecule and its variants, of which HLA-A2.1 is by far the most common, is an effective restricting element for the melanoma-specific CTL response. Additionally, melanoma-specific HLA-restricted CTL lyse the majority of $A2^+$ melanomas tested, Darrow et al., J. Immunol., (1989), 142:3329; Wolfel et al., J. Exp. Med., (1989), 170:797; Hom et al., J. Immunother., (1991), 3:153. By demonstrating lysis of A2-melanomas transfected with the A2.1 gene, it has been shown that these transfected melanomas can present the epitopes recognized by A2-restricted melanoma-specific CTL, Kawakami et al., J. Immunol., (1992), 148:638. These results suggest that these CTL recognize A2-restricted epitopes that are shared by the majority of melanomas, although very little is known about the number and identity of their epitopes.

Epitopes for $CD8^+$ CTL are believed to be short, usually 9-residue peptides that bind to a cleft on the surface of the class I MHC molecule, Udaka et al., Cell, (1992), 69:989; VanBleek et al., Nature, (1990), 348:213; Falk et al., J. Exp. Med., (1991), 174:425. These peptides, generated from proteolysis of endogenous proteins in the cytosol, are transported to the endoplasmic reticulum, where they become associated with newly synthesized class I MHC molecules. They are then transported to the cell surface, Elliott et al., Nature, (1990), 3348:195. Because of the complexity of the peptide mixture associated with class I MHC molecules, Hunt et al., Science, (1992), 255:1261, the definition of individual peptides that comprise specific CTL epitopes has proved extremely difficult. One approach has been to identify the genomic sequence coding for a CTL epitope using Ag loss variants of a melanoma line. The gene encoding a single HLA-A1-restricted melanoma epitope has been isolated by this method, Van der Bruggen et al., Science, (1991), 254:1643. However, only a subset of HLA-A1$^+$ melanomas express this gene. Thus peptides identified using this method would not provide an effective therapy for a majority of melanoma patients.

Tyrosinase (monophenol, 3,4-dihydroxyphenylalanine: oxidoreductase, E.C. 1.14.18.1) has been shown to be specifically expressed by melanocytes and melanoma cells, Brichard et al., supra. The enzyme catalyses the synthesis of dihydroxyphenylalanine (DOPA) in the first two steps of melanin biosynthesis. Autologous CTL recognize an antigen on tumors apparently derived from the tyrosinase molecule. However, this antigen is not recognized by most CTL lines tested.

An alternate approach toward characterization of CTL epitopes is to identify them directly. CTL epitopes have been reconstituted in vitro by allowing exogenous peptides to bind to MHC molecules on the cell surface of target cells, Townsend et al., Annu. Rev. Immunol., (1989), 7:601. To use this approach for the identification of clinically important melanoma-specific epitopes, it is necessary first to demonstrate that peptides comprising these epitopes can be extracted from melanoma cells and that these epitopes are shared by different melanoma lines.

In the present invention, HLA associated peptides have been extracted, isolated and identified from different melanoma lines. These peptides can be used to reconstitute epitopes for HLA-A2.1-restricted melanoma-specific CTL. These peptides and the resulting CTL may be useful for the in vivo immunotherapeutic treatment of melanoma.

SUMMARY OF THE INVENTION

The present invention relates to immunogens which are capable of eliciting a melanoma-specific cytotoxic lymphocyte response in at least some individuals, which response is directed to peptide epitopes carried by those immunogens, and to the use of those immunogens in active specific immunotherapy and immunoprophylaxis against melanoma.

The instant disclosure identifies and synthesizes peptide residues initially isolated from a melanoma cell line. The peptides are capable of reconstituting an epitope recognized by tumor specific CTL. Some of the sequences are homologous with proteins identified as pMEL17, tyrosinase and cofilin. The most active of these sequences have been recognized from 5 out of 5 melanoma patients tested. Fundamentally, the present invention provides for the treatment of melanoma patients using synthetic peptides that reconstitute epitopes for melanoma specific CTL. In another embodiment the peptides are used as vaccines for imparting immunity. Alternatively, in one embodiment the peptides may be used to bind to antigen presenting cells in a method for providing specific antigenic stimulation of CTL. The instant invention provides CTL cell lines capable of recognizing reconstituted HLA-A2.1 epitopes and their use in methods of adoptive immunotherapy. The invention additionally provides for genes encoding for peptides capable of reconstituting epitopes recognized by tumor specific CTL and their use as vaccines in the prevention and management of melanoma.

To identify the active peptides a splitter was devised.

In addition to the potential application of antigenic peptides as the basis of a tumor vaccine in man, there are at least three other utilities: (1) adoptive transfer of tumor-specific CTL generated by stimulation of CTL with antigenic peptides in vitro, and (2) use of peptide bound to target cells (eg T2) for evaluation of the immune response of patients, and (3) use, especially of peptides 946L, and 946I as laboratory reagents for evaluation of peptide/MHC binding affinity.

DETAILED DESCRIPTION OF THE PREFERRED EMBODIMENTS OF THE INVENTION

Figure 1:
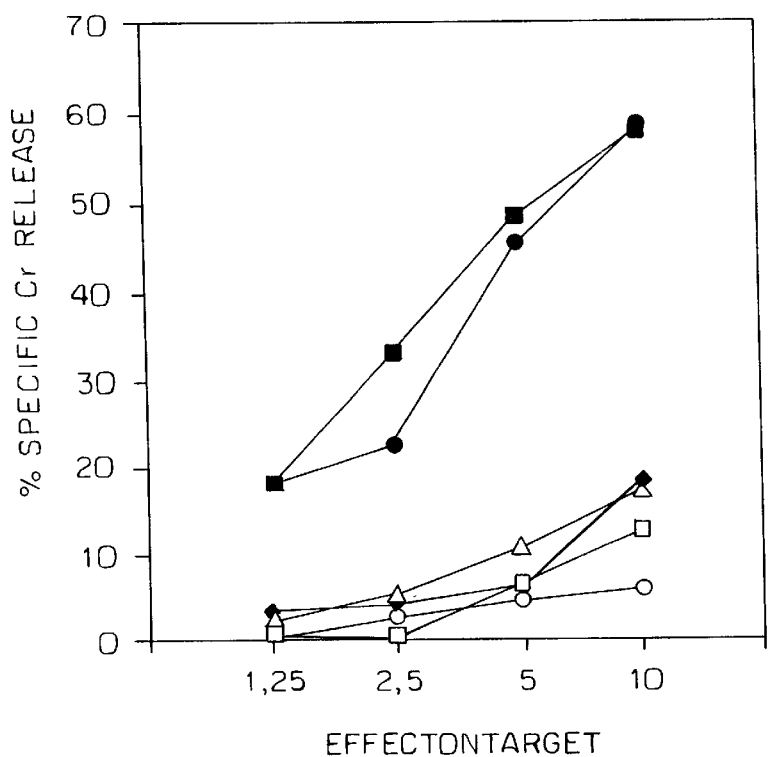
FIG. 1 is a graph of the specificity of VMM5 CTL on day 39.

The present invention relates to certain melanoma-specific CTL epitopes, and their incorporation into immunogens for immunoprophylactic and immunotherapeutic purposes. For the purpose of the present invention, a melanoma-specific CTL epitope is an epitope which is recognized by a T-cell receptor of at least some cytotoxic lymphocytes of at least some individuals in the population of interest, and which is more frequently or strongly associated with melanoma cells than with at least some other cancer and/or normal cells. Absolute specificity is not required, provided that a useful prophylactic or therapeutic effect is still obtained.

Melanoma-Specific CTL Epitopes

The melanoma-specific CTL epitopes of the present invention are peptides, typically 9–11 amino acids in length, which are identical to or otherwise substantially homologous with melanoma-specific peptide epitopes recognized by melanoma-specific CTLs. The family of melanoma epitopes which are recoverable from an individual is dependent on the nature of the binding site of the Class I MHC (HLA) molecules expressed by the individual, and, as a result of the polymorphism of the Class I MHC (HLA) molecules, can vary considerably from one individual to another. For the purpose of the present invention, the melanoma cell line used as a source of melanoma-specific CTL epitopes may be any melanoma cell line; similarly, the Class I MHC (HLA) molecule may be any such molecule borne by a melanoma which is capable of binding to and presenting a melanoma-specific epitope, including, but not limited to, the various allelic forms of Class I MHC molecules enumerated in Table I. Epitopes presentable by HLA-A2.1 are of particular interest, as it is a common form of HLA-A.

The 946 peptide, although recognized by melanoma-specific CTL, may not be optimal at present. It is known that some residues on the nonamer peptide are particularly important for binding of the peptide to the MHC molecule (residues 2,9), while others are particularly important for Tc recognition (residues 4–8). The other residues may be important for either or both. It is proposed that amino acid substitutions for the 946 peptide may be useful at increasing immunogenicity, particularly by attempting to change residues that may increase binding to the MHC such as changing residue 9 to a valine or residue 3 to anything other than glutamic acid (E). Using existing knowledge about which of these residues may be more likely to affect binding either to the MHC or to the TcR, a rational approach to this process may be employed. The resulting peptides, if more effective, could be used for any of the purposes described in this proposal. (refs: E. L. Huczko et al. J. Immunol. 151:2572, 1993; J. Ruppert et al. Cell 754: 929, 1993; Madden Dr et al. Cell 75:693–708, 1994.)

Therefore, in addition to epitopes which are identical to the naturally occurring melanoma-specific epitopes, the present invention embraces epitopes which are substantially homologous with such epitopes, and therefore melanoma-specific in their own right.

The term "substantially homologous", when used in connection with amino acid sequences, refers to sequences which are substantially identical to or similar in sequence with each other, giving rise to a homology in conformation and thus to similar (or improved) biological activity. The term is not intended to imply a common evolution of the sequences.

Substantially homologous peptide epitopes may be identified by a variety of techniques. It is known in the art that one may synthesize all possible single substitution mutants of a known peptide epitope. For a nonapeptide, there are (20×9−1=179) such mutants. Geysen, et al., Proc Nat. Acad. Sci. (USA), 81:3998–4002 (1984). While the effects of different substitutions are not always additive, it is reasonable to expect that two favorable or neutral single substitutions at different residue positions in the epitope can safely be combined in most cases.

One may also synthesize a family of related single or multiple substitution mutants, present the mixture to the HLA-A2.1 positive lymphoblastoid cell line T2 (or other cell line capable of presenting melanoma-specific CTL epitopes), and expose the T2 cells to melanoma-specific CTLs. If the T2 cells are lysed, the effective epitopes may be identified either by direct recovery from the T2 cells or by a progressive process of testing subsets of the effective peptide mixtures. Methods for the preparation of degenerate peptides are described in Rutter, U.S. Pat. No. 5,010,175, Haughten, et al., Proc. Nat. Acad. Sci. (USA), 82:5131–35 (1985), Geysen, et al., Proc. Nat. Acad. Sci. (USA), 81:3998–4002 (1984); WO861/06487; WO86/00991.

In the case of the peptide 946L (SEQ. ID. No.:14), a possible multiple mutageneis strategy would be as follows:

| Parental | Tyr | Leu | Glu | Pro | Gly | Pro | Val | Thr | Ala |
|---|---|---|---|---|---|---|---|---|---|
| Possible Mutations | Phe Trp | Ile Val Met | Asp | Ala Ser Thr Gly | Pro Ala Ser Thr | Ala Ser Thr Gly | Ile Leu Met | Ala Ser Pro Gly | Thr Ser Pro Gly |

There would be about 300,000 different peptides in this family.

The person of ordinary skill in the art, in determining which residues to vary, may also make comparisons of the sequences of the naturally processed MHC associated peptides, and may obtain 3D structures of the MHC: peptide: TCR complexes, in order to identify residues involved in MHC or TCR binding. Such residues may either be left alone, or judiciously mutated in an attempt to enhance MHC or TCR binding.

It is also possible to predict substantially homologous epitopes by taken into account studies of sequence variations in families of naturally occurring homologous proteins. Certain amino acid substitutions are more often tolerated than others, and these are often correlatable with similarities in size, charge, etc. between the original amino acid and its replacement. Insertions or deletions of amino acids may also be made.

Conservative substitutions are herein defined as exchanges within one of the following five groups:

I. Small aliphatic, nonpolar or slightly polar residues:
  Ala, Ser, Thr, Pro, Gly
II. Polar, negatively charged residues: and their amides
  Asp, Asn, Glu, Gln
III. Polar, positively charged residues:
  His, Arg, Lys
IV. Large, aliphatic, nonpolar residues:
  Met, Leu, Ile, Val, Cys
V. Large, aromatic residues:
  Phe, Tyr, Trp Within the foregoing groups, the following substitutions are considered "highly conservative":
  Asp/Glu
  His/Arg/Lys
  Phe/Tyr/Trp
  Met/Leu/Ile/Val Semi-conservative substitutions are defined to be exchanges between two of groups (I)–(V) above which are limited to supergroup (A), comprising (I), (II) and (III) above, or to supergroup (B), comprising (IV) and (V) above.

Substitutions are not limited to the genetically encoded, or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole-(alkyl)alanines, and D- or L-alkylainines where alkyl may be substituted or unsubstituted methyl, ethyl, propyl, hexyl, butyl, pentyl, iso-propyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., —$SO_3H$) threonine, serine, tyrosine.

Other substitutions may include unnatural hyroxylated amino acids made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage can be replaced by a ketomethylene moiety, e.g. (—C(=O)—CH$_2$—) for (—(C=O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid can be replaced by the same amino acid but of the opposite chirality. Thus, any amino acid naturally occurring in the L-configuration (which may also be referred to as the R or S configuration, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be readily deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *Proteins: Structure and Molecule Properties*, W. H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps. Glycosylation is also possible.

Derivatized moieties may improve the solubility, absorption, biological half life, and the like, or eliminate or attenuate any possible undesirable side effect of the molecule. Moieties capable of mediating such effects are disclosed, for example, in *Remington's Pharmaceutical Sciences*, 16th ed., Mack Publishing Co., Easton, Pa. (1980).

The Melanoma-Specific Immunogen

The melanoma-specific immunogen of the present invention is a molecule corresponding to or otherwise comprising a melanoma-specific CTL epitope as previously described. The immunogen may comprise one or more melanoma-specific CTL epitopes, which may be the same or different. If it comprises a plurality of such epitopes, they may be linked directly, or through a spacer of some kind. The immunogen may take any form that is capable of eliciting a melanoma-specific cytotoxic immune response. By way of example and not of limitation, the immunogen may be a fusion of a plurality of CTL epitopes which is sufficiently large to be immunogenic, a conjugate of one or more epitopes to a soluble immunogenic macromolecular carrier, such as serum albumin, keyhole limpet hemocyanin, or dextran, a recombinant virus engineeered to display the epitope on its surface, or a conjugate of a plurality of epitopes to a branched lysine core structure, a so-called "multiple antigenic peptide" (see Posnett,.et al., J. Biol. Chem., 263:1719–25, 1988). The immunogenic conjugate may also comprise moieties intended to enhance the immune response, such as a cytokine.

Mode of Production

The peptide portion of the immunogens of the present invention may be produced by any conventional technique, including (a) nonbiological synthesis by sequential coupling of component amino acids, (b) production by recombinant DNA techniques in a suitable host cell, and (c) chemical or enzymatic modification of a sequence made by (a) or (b) above.

Gene Expression. The peptides disclosed herein may be produced, recombinantly, in a suitable host, such as bacteria from the genera Bacillus, Escherichia, Salmonella, Erwinia, and yeasts from the genera Hansenula, Kluyveromyces, Pichia, Rhinosporidium, Saccharomyces, and Schizosaccharomyces, or cultured mammalian cells such as COS-1. The more preferred hosts are microorganisms of the species *Pichia pastoris, Bacillus subtilis, Bacillus brevis, Saccharomyces cerevisiae, Escherichia coli* and *Yarrowia lipolytica*. Any promoter, regulatable or constitutive, which is functional in the host may be used to control gene expression.

It has been found that a peptide fragment from the protein pMEL17 reconstitutes an HLA epitope. The pMEL17 gene is a single-stranded cDNA reading 5' to 3'. The gene encoding for pMEL17, SEQ. ID. NO. 91 is:

GGAAGAACAC AATGGATCTG GTGCTAAAAA
GATGCCTTCT TCATTTGGCT GTGATAGGTG
CTTTGCTGGC TGTGGGGGCT ACAAAAGTAC
CCAGAAACCA GGACTGGCTT GGTGTCTCAA
GGCAACTCAG AACCAAAGCC TGGAACAGGC
AGCTGTATCC AGAGTGGACA GAAGCCCAGA
GACTTGACTG CTGGAGAGGT GGTCAAGTGT
CCCTCAAGGT CAGTAATGAT GGGCCTACAC
TGATTGGTGC AAATGCCTCC TTCTCTATTG
CCTTGAACTT CCCTGGAAGC CAAAAGGTAT
TGCCAGATGG GCAGGTTATC TGGGTCAACA
ATACCATCAT CAATGGGAGC CAGGTGTGGG
GAGGACAGCC AGTGTATCCC CAGGAAACTG
ACGATGCCTG CATCTTCCCT GATGGTGGAC
CTTGCCCATC TGGCTCTTGG TCTCAGAAGA
GAAGCTTTGT TTATGTCTGG AAGACCTGGG
GCCAATACTG GCAAGTTCTA GGGGGCCCAG
TGTCTGGGCT GAGCATTGGG ACAGGCAGGG
CAATGCTGGG CACACACACC ATGGAAGTGA
CTGTCTACCA TCGCCGGGGA TCCCGGAGCT
ATGTGCCTCT TGCTCATTCC AGCTCAGCCT
TCACCATTAC TGACCAGGTG CCTTTCTCCG
TGAGCGTGTC CCAGTTGCGG GCCTTGGATG
GAGGGAACAA GCACTTCCTG AGAAATCAGC
CTCTGACCTT TGCCCTCCAG CTCCATGACC
CTAGTGGCTA TCTGGCTGAA GCTGACCTCT
CCTACACCTG GGACTTTGGA GACAGTAGTG
GAACCCTGAT CTCTCGGGCA CCTGTGGTCA
CTCATACTTA CCTGGAGCCT GGCCCAGTCA
CTGCCCAGGT GGTCCTGCAG GCTGCCATTC
CTCTCACCTC CTGTGGCTCC TCCCCAGTTC
CAGGCACCAC AGATGGGCAC AGGCCAACTG
CAGAGGCCCC TAACACCACA GCTGGCCAAG
TGCCTACTAC AGAAGTTGTG GGTACTACAC
CTGGTCAGGC GCCAACTGCA GAGCCCTCTG
GAACCACATC TGTGCAGGTG CCAACCACTG
AAGTCATAAG CACTGCACCT GTGCAGATGC
CAACTGCAGA GAGCACAGGT ATGACACCTG
AGAAGGTGCC AGTTTCAGAG GTCATGGGTA
CCACACTGGC AGAGATGTCA ACTCCAGAGG
CTACAGGTAT GACACCTGCA GAGGTATCAA
TTGTGGTGCT TTCTGGAACC ACAGCTGCAC
AGGTAACAAC TACAGAGTGG GTGGAGACCA
CAGCTAGAGA GCTACCTATC CCTGAGCCTG
AAGGTCCAGA TGCCAGCTCA ATCATGTCTA
CGGAAAGTAT TACAGGTTCC CTGGGCCCCC
TGCTGGATGG TACAGCCACC TTAAGGCTGG
TGAAGAGACA AGTCCCCCTG GATTGTGTTC
TGTATCGATA TGGTTCCTTT TCCGTCACCC
TGGACATTGT CCAGGGTATT GAAAGTGCCG
AGATCCTGCA GGCTGTGCCG TCCGGTGAGG
GGGATGCATT TGAGCTGACT GTGTCCTGCC
AAGGCGGGCT GCCCAAGGAA GCCTGCATGG
AGATCTCATC GCCAGGGTGC CAGCCCCCTG
CCCAGCGGCT GTGCCAGCCT GTGCTACCCA
GCCCAGCCTG CCAGCTGGTT CTGCACCAGA
TACTGAAGGG TGGCTCGGGG ACATACTGCC
TCAATGTGTC TCTGGCTGAT ACCAACAGCC
TGGCAGTGGT CAGCACCCAG CTTATCATGC
CTGTGCCTGG GATTCTTCTC ACAGGTCAAG
AAGCAGGCCT TGGGCAGGTT CGGCTGATCG
TGGGCATCTT GCTGGTGTTG ATGGCTGTGG
TCCTTGCATC TCTGATATAT AGGCGCAGAC
TTATGAAGCA AGACTTCTCC GTACCCCAGT
TGCCACATAG CAGCAGTCAC TGGCTGCGTC
TACCCCGCAT CTTCTGCTCT TGTCCCATTG
GTGAGAATAG CCCCCTCCTC AGTGGGCAGC
AGGTCTGAGT ACTCTCATAT GATGCTGTGA
TTTTCCTGGA GTTGACAGAA ACACCTATAT
TTCCCCCAGT CTTCCCTGGG AGACTACTAT
TAACTGAAAT AAATACTCAG AGCCTGAAAA A

Of particular importance within the context of the present invention is the peptide Tyr Xaa Glu Pro Gly Pro Val Thr Alaa (SEQ ID NO:93) and its encoding gene sequence, (SEQ. ID. No. 90) TAC CTG GAG CCT GGC CAA GTC ACT GCC. Because this peptide has proven immunologic activity, it is ideal for specific immunization. Such immunization may be accomplished either directly, or by use of a vaccine consisting of virus (e.g., Vaccinia) encoding or HLA-A2 cells expressing a genetic sequence encoding this peptide. Also promising is the gene sequence encoding Tyr Met Asp Gly Thr Met Ser Gln Val (SEQ ID NO:9) TAT ATG GAT GGA ACA ATG TCC GAG GTA (SEQ ID NO: 92), because of its homology to the tyrosinase protein and its existence in association with HLA-A2.1 molecules or melanoma cells.

These sequences may be constructed in such a manner, including the appropriate expression systems for use in gene therapy procedures. Because several different nucleotide sequences may encode a single amino acid, alternate DNA sequences may also encode these peptides.

Standard reference works setting forth the general principles of recombinant DNA technology include Watson, J.

D., et al., *Molecular Biology of the Gene*, Volumes I and II, The Benjamin/Cummings Publishing Company, Inc., publisher, Menlo Park, Calif. (1987); Darnell, J. E., et al., *Molecular Cell Biology*, Scientific American Books, Inc., lo publisher, New York, N.Y. (1986); Lewin, B. M., Genes II, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); Sambrook, J., et al., *Molecular Cloning: A Laboratory Manual*, Cold Spring Harbor Laboratory, Cold Spring Harbor, N.Y. (1989); and Ausubel, et al., *Current Protocols in Molecular Biology*, Wiley Interscience, N.Y., (1987, 1992). These references are herein entirely incorporated by reference.

Chemical Peptide Synthesis. Chemical peptide synthesis is a rapidly evolving area in the art, and methods of solid phase peptide synthesis are well-described in the following references, hereby entirely incorporated by reference: (Merrifield, B., *J. Amer. Chem. Soc.* 85:2149–2154 (1963); Merrifield, B., *Science* 232:341–347 (1986); Wade, J. D., et al., *Biopolymers* 25:S21–S37 (1986); Fields, G.B., *Int. J. Polypeptide Prot. Res.* 35:161 (1990); MilliGen Report Nos. 2 and 2a, Millipore Corporation, Bedford, Mass., 1987) Ausubel, et al, supra, and Sambrook, et al, supra.

In general, as is known in the art, such methods involve blocking or protecting reactive functional groups, such as free amino, carboxyl and thio groups. After polypeptide bond formation, the protective groups are removed (or de-protected). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

In the more classical method, known as the "tBoc method," the amino group of the amino acid being added to the resin-bound C-terminal amino acid is blocked with tert-butyloxycarbonyl chloride (tBoc). This protected-amino acid is reacted with the bound amino acid in the presence of the condensing agent dicyclohexylcarbodiimide, allowing its carboxyl group to form a polypeptide bond the free amino group of the bound amino acid. The amino-blocking group is then removed by acidification with trifluoroacetic acid (TFA); it subsequently decomposes into gaseous carbon dioxide and isobutylene. These steps are repeated cyclically for each additional amino acid residue. A more vigorous treatment with hydrogen fluoride (HF) or trifluoromethane-sulfonyl derivatives is common at the end of the synthesis to cleave the benzyl-derived side chain protecting groups and the polypeptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the α-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethylformamide (DMF), and the final HF cleavage treatment is eliminated. A TFA solution is used instead to cleave side chain protecting groups and the peptide resin linkage simultaneously.

At least three different peptide-resin linkage agents can be used: substituted benzyl alcohol derivatives that can be cleaved with 95% TFA to produce a peptide acid, methanolic ammonia to produce a peptide amide, or 1% TFA to produce a protected peptide which can then be used in fragment condensation procedures, as described by Atherton, E., et al., *J. Chem. Soc. Perkin Trans.* 1:538–546 (1981) and Sheppard, R. C., et al., *Int. J. Polypeptide Prot. Res.* 20:451–454 (1982). Furthermore, highly reactive Fmoc amino acids are available as pentafluorophenyl esters or dihydro-oxobenzotriazine esters derivatives, saving the step of activation used in the tBoc method.

Pharmaceutical Methods and Preparations

The preferred animal subject of the present invention is a primate mammal. By the term "mammal" is meant an individual belonging to the class Mammalia, which, of course, includes humans. The invention is particularly useful in the treatment of human subjects, although it is intended for veterinary uses as well. By the term "non-human primate" is intended any member of the suborder Anthropoidea except for the family Hominidae. Such non-human primates include the superfamily Ceboidea, family Cebidae (the New World monkeys including the capuchins, howlers, spider monkeys and squirrel monkeys) and family Callithricidae (including the marmosets); the superfamily Cercopithecoidea, family Cercopithecidae (including the macaques, mandrills, baboons, proboscis monkeys, mona monkeys, and the sacred hunaman monkeys of India); and superfamily Hominoidea, family Pongidae (including gibbons, orangutans, gorillas, and chimpanzees). The rhesus monkey is one member of the macaques.

The term "protection", as used herein, is intended to include "prevention," "suppression" and "treatment." "Prevention" involves administration of the protein prior to the induction of the disease. "Suppression" involves administration of the composition prior to the clinical appearance of the disease. "Treatment" involves administration of the protective composition after the appearance of the disease.

It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." It should also be understood that to be useful, the protection provided need not be absolute, provided that it is sufficient to carry clinical value. An agent which provides protection to a lesser degree than do competitive agents may still be of value if the other agents are ineffective for a particular individual, if it can be used in combination with other agents to enhance the level of protection, or if it is safer than competitive agents.

The form of administration may be systemic or topical. For example, administration of such a composition may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

A typical regimen comprises administration of an effective amount of the immunogen, administered over a period ranging from a single dose, to dosing over a period of hours, days, weeks, months, or years.

It is understood that the suitable dosage of a immunogen of the present invention will be dependent upon the age, sex, health, and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This will typically involve adjustment of a standard dose, e.g., reduction of the dose if the patient has a low body weight.

Prior to use in humans, a drug will first be evaluated for safety and efficacy in laboratory animals. In human clinical studies, one would begin with a dose expected to be safe in humans, based on the preclinical data for the drug in question, and on customary doses for analogous drugs (if any). If this dose is effective, the dosage may be decreased, to determine the minimum effective dose, if desired. If this dose is ineffective, it will be cautiously increased, with the patients monitored for signs of side effects. See, e.g., Berkow, et al., eds., *The Merck Manual*, 15th edition, Merck and Co., Rahway, N.J., 1987; Goodman, et al., eds., *Goodman and Gilman's The Pharmacological Basis of Therapeutics*, 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985), which references and references cited therein, are entirely incorporated herein by reference.

The total dose required for each treatment may be administered by multiple doses or in a single dose. The immunogen may be administered alone or in conjunction with other therapeutics directed to the disease or directed to other symptoms thereof.

The appropriate dosage form will depend on the disease, the immunogen, and the mode of administration; possibilities include tablets, capsules, lozenges, dental pastes, suppositories, inhalants, solutions, ointments and parenteral depots. See, e.g., Berker, supra, Goodman, supra, Avery, supra and Ebadi, supra, which are entirely incorporated herein by reference, including all references cited therein. However, it is expected that each vaccine preparation will include 1–100 ug of the peptide epitope.

In addition to at least one immunogen as described herein, a pharmaceutical composition may contain suitable pharmaceutically acceptable carriers, such as excipients, carriers and/or auxiliaries which facilitate processing of the active compounds into preparations which can be used pharmaceutically. See, e.g., Berker, supra, Goodman, supra, Avery, supra and Ebadi, supra, which are entirely incorporated herein by reference.

The composition may also include an adjuvant, such as DETOX (Ribi Immunochemicals)(muramyl dipeptide and cell wall fragments from Mycobacterium phlei). If desired, the adjuvant may be conjugated to the epitope and not simply a part of a mixture. See Deres, et al, Nature, 342:561–4 (1989).

The composition may also include an immunomodulator, especially cytokines such as IL-1, IL-2, IL-4, IL-6, IL-7, IL-12, Interferon-alpha, Interferon-gamma, Granulocyte Macrophage Colony Stimulating Factor (GMCSF), Tumor Necrosis Factor (TNF)-alpha, and TNF-beta.

A pharmaceutical composition according to the present invention may further comprise at least one cancer chemotherapeutic compound, such as one selected from the group consisting of an anti-metabolite, a bleomycin peptide antibiotic, a podophyllin alkaloid, a Vinca alkaloid, an alkylating agent, an antibiotic, cisplatin, or a nitrosourea. A pharmaceutical composition according to the present invention may further or additionally comprise at least one viral chemotherapeutic compound selected from gamma globulin, amantadine, guanidine, hydroxybenzimidazole, interferon-$\alpha$, interferon-$\beta$, interferon-$\gamma$, thiosemicarbarzones, methisazone, rifampin, ribvirin, a pyrimidine analog, a purine analog, foscarnet, phosphonoacetic acid, acyclovir, dideoxynucleosides, or ganciclovir. See, e.g., Katzung, supra, and the references cited therein on pages 798–800 and 680–681, respectively, which references are herein entirely incorporated by reference.

As an alternative to a pharmaceutical composition comprising the immunogen of the present invention, per se, the pharmaceutical composition may instead comprise a vector comprising an expressible gene encoding such an immunogen. The pharmaceutical composition and method would then be chosen so that the vector was delivered to suitable cells of the subject, so that the gene would be expressed and the immunogen produced in such a manner as to elicit an immune response. A preferred vector would be a Vaccinia virus, such as a construct containing a minigene encoding the peptide 946L (Tyr Leu Glu Pro Gly Pro Val Thr Ala (SEQ ID NO:14)) or 946I (Tyr Ile Glu Pro Gly Pro Val Thr Ala (SEQ ID NO:39)). A preferred route for immunization would be scarification. A preferred immunization protocol would be 10E6 to 10E8 pfu/dose in the initial injection, followed up with boosters at 1,3 and 12 months.

Recombinant vaccinia virus constructs have been used for immunization against hepatitis B (Moss, et al., *Nature*, 311, 67, 1984), herpes simplex virus (Wacchsman, et al., *Biosci. Rep.* 8, 323; 334, 1988), parainfluenza type 3 (Spriggs, et al., *J. Virol.*, 62, 1293, 1988), and Lassa fever virus (Fisher-Hoch, et al., *Proc. Natl. Acad. Sci. USA*, 86, 317, 1989). Vaccinia virus constructs comprising gene for cancer-associated antigens have also been prepared (Lathe, et al., *Nature*, 326, 878, 1987; Bernards, et al., *Proc. Natl. Acad. Sci. USA*, 84, 6854, 1987; Estin, et al., *Proc. Natl. Acad. Sci. USA*, 85, 1052, 1988).

Adoptive transfer of melanoma-specific CTL has been accompanied by tumor shrinkage in a large minority of patients with advanced melanoma and by disappearance of all detectable tumor in a smaller proportion of patients. (Rosenberg et al, NEM 319: 1676–1680, 19888) and in animal studies appears to be particularly promising for the treatment of solid tumors (Rosenberg SA et al. Science 233:1318–1321). One of the problems with existing methods for CTL generation is that they require the resection of large metastic tumor deposits to initiate the process. If the requirement for available autologous tumor could be circumvented, then patients with no measurable disease but a high risk of recurrence (eg, melanoma patients with primary tumors greater than 4 mm thick or with tumor metastatic to regional nodes) could be treated with adoptive therapy even if their tumor were removed and fixed in formalin and no other gross tumor was evident. These patients have a very high likelihood of harboring micrometastic disease for which no other effective therapy is now available; so most will die of the melanoma. It is possible that the presence of bulky tumor suppresses the autologous immune response; so treatment of patients without bulky disease would be an attractive goal. Especially in murine systems, CTL have been generated and maintained by stimulation with cells to which the peptide epitope has been bound. We propose that HLA-A2.1+ cells (autologous B cells, macrophages, or dendritic cells, ideally) would be pulsed in vitro with peptide (e.g., peptide 946, Tyr Xaa Glu Pro Gly Pro Val Thr Ala (SEQ ID NO:93) and used as in vitro simulators for autologous lymph node cells or peripheral blood lymphocytes. The patients could be pre-stimulated with a peptide vaccine prior lymphocyte harvest if the existing response was inadequate. Lymphocytes stimulated with peptide in vitro could then be expanded to $10^{10}$ or $10^{11}$ cells, then re-infused into the patients in a manner analogous to that used for LAK cell therapy. It is expected that the adoptively transferred CTL would survive best with IL-2 infusion at low to intermediate doses, and that putative inhibitors of Tc suppression (eg: cyclophosphamide) may be employed also, prior to the infusions of CTL.

Nontherapeutic Uses and Compositions

The relationship between the host's immune response and his or her tumor is poorly understood. Better understanding of that response depends on evaluation of the specific responses against individual epitopes, such as the 946 peptide. If patients do have an immune response to 946 naturally, then evaluation and quantitation of that by precursor frequency analysis of the CTL in the patient's blood pool may permit some assessment of the protection that person's immune system is providing. As new therapies become available for melanoma, it may be useful to screen patients for the presence of the 946 peptide on their tumor and the presence of CTL in their blood pool with specificity for the 946 peptide on HLA-A2. These findings may determine whether further augmentation of the immune response is indicated or whether other, non-immunologic, therapy should be employed. A parallel to this is the determination on breast cancers of the presence of estrogen and progesterone receptors before considering hormonal therapy or chemotherapy.

Thus, the peptides of the present invention may be used to screen a sample for the presence of an antigen with the same epitope, or with a different but cross-reactive epitope, or for the presence of CTLs which specifically recognize the corresponding epitopes. The sample will normally be a biological fluid, such as blood, urine, lymphatic fluid, amniotic fluid, semen, saliva, tears, milk, or cerebrospinal fluid, or a fraction or derivative thereof, or a biological tissue, in the form of, e.g., a tissue section or homogenate. The preferred sample is blood, or a fraction or derivative thereof.

Assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

Assays may also be divided into competitive and noncompetitive formats. In the competitive format, the analyte competes with a labeled analyte analogue for binding to a binding partner. In a common noncompetive format called a sandwich assay, the analyte is first bound by a capture reagent, and then by a tag reagent.

In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^3$H, $^{125}$I, $^{131}$I, $^{35}$S, $^{14}$c, and, preferably, $^{125}$I.

It is also possible to label a compound with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}$Eu, or others of the lanthanide series, may be attached to the binding protein using such metal chelating groups as diethylenetriaminepentaacetic acid (DTPA) and ethylenediamine-tetraacetic acid (EDTA).

The peptides also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase, alkaline phosphatase, malate dehydrogenase, staphylococcal nuclease, δ-V-steroid isomerase, yeast alcohol dehydrogenase, α-glycero phosphate dehydrogenase, triose phosphate isomerase, asparaginase, glucose oxidase, β-galactosidase, ribonuclease, glucose-6-phosphate dehydrogenase, glucoamylase and acetylcholine esterase, are preferred. When an enzyme label is used, the signal producing system must also include a substrate for the enzyme. If the enzymatic reaction product is not itself detectable, the SPS will include one or more additional reactants so that a detectable product appears.

A label may be conjugated, directly or indirectly (e.g., through a labeled antibody), covalently (e.g., with SPDP) or noncovalently, to the peptide, to produce a diagnostic reagent. Similarly, the peptide may be conjugated to a solid phase support to form a solid phase ("capture") diagnostic reagent. Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Additionally, the peptides may be used as a diagnostic tool to evaluate whether other immunotherapeutic treatments (tumor vaccines of any kind, adoptive transfer of CTL, etc) are having a beneficial effect.

Figure 11:
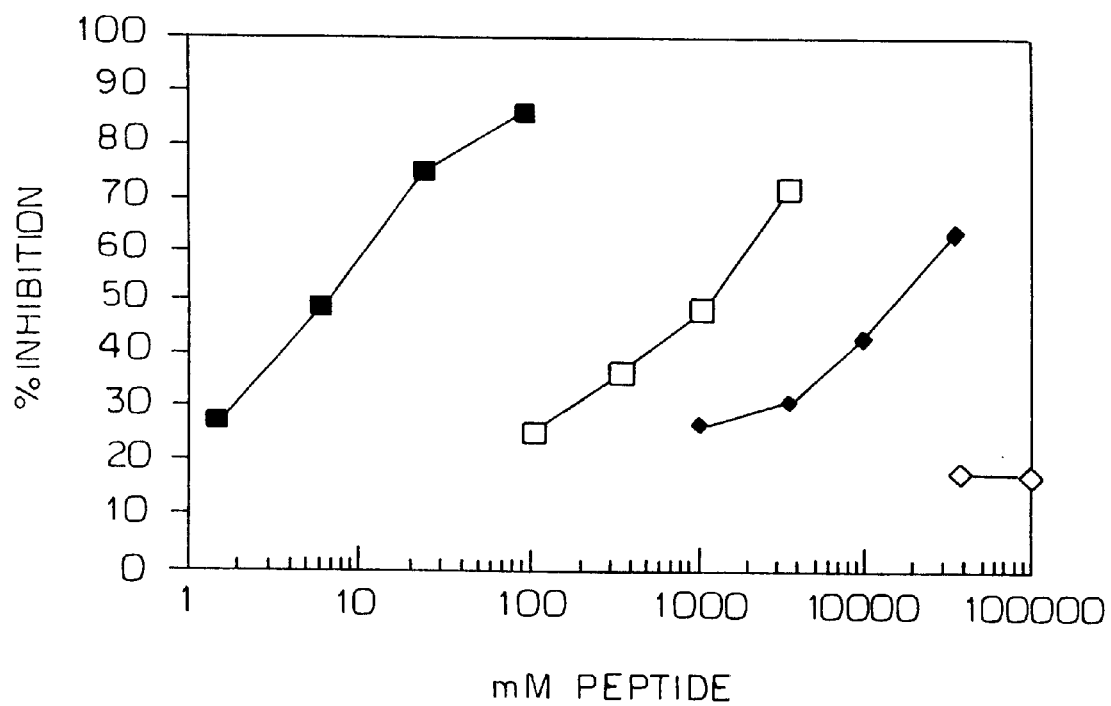
FIG. 11 illustrates the binding of synthetic 946 peptides to HLA-A2.1.

Also the peptides 946L Tyr Leu Glu Pro Gly Pro Val Thr Ala (SEQ ID NO:14) and 946I Tyr Ile Glu Pro Gly Pro Val Thr Ala (SEQ ID NO:39) have very low affinity for the HLA-A2.1 molecule. This is illustrated in FIG. 11. For this reason, they will be useful as control peptides for the evaluation of binding affinity. Because they represent a low affinity range, they can be used in laboratory studies on binding affinity of other peptides. This methodology, in a preferred embodiment, would likely include: binding the peptide to T2 cells, then evaluating lysis of the T2 cells by any of various standard methods, such as a proliferative response of the CTL, or cytokine release by the CTL exposed to the T2 cells+ peptide.

EXAMPLES

Materials and Methods
Cell Lines and HLA Typing

All tumor cell lines were of human origin. Melanoma cell lines HT144 and Sk-Mel-24, osteosarcoma 143b, colon cancer CCL-228 (SW480), and breast cancer MDA-MB-468 were obtained from the American Type Culture Collection (Bethesda, Md.). Fibroblasts GM126 were obtained from the National Institute of General Medical Sciences Human Genetic Mutant Cell Repository, Bethesda, Md. Melanoma lines DM6, DM13, DM14, and DM93 were the gift of Drs. Hilliard F. Siegler and Timothy L. Darrow. VMM1 and VMM5 are melanoma cell lines established from metastatic melanoma resected from patients at the University of Virginia (Charlottesville, Va.). VBT2 (squamous cell lung carcinoma), VAO1 (adenocarcinoma of the ovary), and VAB5 (adenocarcinoma of the breast) are cell lines also established at this institution. JY, MICH, MWF, 23.1, RPMI 1788, and Herluff are EBV-transformed B lymphoblastoid lines. K562 is a NK-sensitive human erythroleukemia line. The cell line T2 is derived from the fusion of a T cell line, CEM, and a human B cell mutant, LCL 721.174. This cell line expresses HLA-A2.1 molecules but has an Ag-processing defect that is associated with enhanced presentation of exogenous peptides.

HLA types of the specimens used in this study are summarized in Table 1.

TABLE 1

Human cell lines used in this study: HLA types and susceptibility to lysis by VMM5 CTL[1a]

| Cell Line (Ref.) | Cell Type[b] | HLA-A | HLA-B | HLA-C | HLA-DR | HLA-DQ | Lysis by VMM5 CTL[a] |
|---|---|---|---|---|---|---|---|
| DM6 (11) | Melanoma | 2.1[c] | 12, 13 or 35 | 1, 2 | 6.10. (7)[d] | ---[c] | ++ |
| DM135 (11) | Melanoma | 2.1, 31 | 13, 18 | ND | ND | ND | +++ |
| DM14 (11) | Melanoma | 11, 28 | 5, 8 | 2, 4 | --- | --- | -- |
| DM93 (11) | Melanoma | 2.1, 33 | 8, 49, w6 | ND | 2, 4, 6[d] | 3 | ++ |
| SkMe124 (26) | Melanoma | 1, 2.1 | 12, 14 | --- | --- | --- | -- |
| HT144 (26) | Melanoma | 1, 24 | 13, 15 | 3 | 4, 7 | --- | -- |
| HT14140 A2--03 | Melanoma | 1, 2.1, 24 | 13, 15 | 3 | 4, 7 | --- | + |
| VMM1 | Melanoma | 3, 26 | 51, w4, w6 | ND | --- | --- | -- |
| VMM5 | Melanoma | 2.1 | 39 | ND | 7, 11, 52, 53 | 2, 7 | +++ |
| VBT2 | Lung CA | 34, 68 | 35, (53?) | 4? | --- | --- | -- |
| VA01 | Ovarian CA | 2 | --- | --- | --- | --- | -- |
| VAB515 | Breast CA | 2, 25 | 60, 62 | 3 | --- | --- | -- |
| MDAMB468 (26) | Breast CA | 23, 30 | 27, 35 | 2, 4 | --- | --- | -- |
| CCL228 (26) | Colon CA | 2.1 | 8, 17 | --- | --- | --- | -- |
| 143b (29) | Osteosarcoma | 2.1 | --- | --- | --- | --- | -- |
| GM126 (29) | Fibroblasts | 2.1 | --- | --- | --- | --- | -- |
| K56220 | Erythroleukemia | --- | --- | --- | --- | --- | -- |
| MICH (28) | EBV-6[g] | 2.1, 32 | 15, 27 | --- | 5, 5 | --- | -- |
| RPMI-1788 (26) | EBV-6 | 2.1, 33 | 7, 14 | --- | --- | --- | -- |
| JY (28) | EBV-6 | 2.1, 2.1 | 7, 7 | --- | 4, 6 | --- | -- |
| Herluff (27) | EBV-6 | 2.1, 2.1 | 12, 35 | --- | --- | --- | -- |
| 23.125 (28) | EBV-6 | 2, 2 | 27, 27 | --- | 8, 8 | --- | -- |

Expression of HLA-A2 on tumor cells was assessed by staining with BB7.2. Expression of the A2 subtype HLA-A2.1 was confirmed by susceptibility to lysis by HLA-A2.1-specific murine CTL clones AT1-15 and AX21-9, and by staining with HLA-A2.1/A2.2-specific mAb CR11.351.
Generation of Tumor-specific Cytotoxic T Cells Detailed methods of CTL generation have been previously reported. Malignant melanoma metastatic to cervical lymph nodes was resected from an 80-yr old patient designated VMM5. The nodes were mechanically dissociated and then enzymatically digested in Eagle's MEM (GIBCO, Grand Island, N.Y.) containing 2.5% FCS (GIBCO, or Whittaker, Walkersville, Md.), 0.1% collagenase B (Boehringer-Mannheim, Indianapolis, Ind.), 0.002% DNase (Sigma, St. Louis, Mo.), penicillin 100 U/ml, streptomycin 100 microg/ml (Pen-Strept, GIBCO) at room temperature. After 4 h, dissociated cells were collected and cryopreserved. Remaining tumor fragments were returned to the digestion media overnight. The digests were harvested in a similar fashion daily for 3 days, with viable tumor cells and lymphocytes obtained each day. These cells were cryopreserved in FCS+10% DMSO in liquid nitrogen. Initial cultures were established with the mixture of lymphocytes and tumor from the tumor-involved node. The ratio of tumor cells to lymphocytes placed in culture were approximately 1:1. The cells were cultured in 24-well tissue culture plates (Linbro, Hamden, Conn.) in RPMI 1640 (Sigma) containing 10% FCS, Pen-Strept, and 20 U/ml rIL-2 (Cetus, Emeryville, Calif.). The CTL were restimulated with irradiated (100 Gy) fresh cryopreserved autologous tumor (VMM5) at a TLR (tumor:lymphocyte ratio) of 1:10 on day 16. Beginning with the third in vitro stimulation (day 32), and thereafter every 10 to 15 days, the CTL were restimulated with the allogeneic HLA-A2.1$^+$ melanoma cell line DM6. A TLR of 1:5 was used until the cells were 70 days old, after which a TLR between 1:2 and 2:1 was used. Several VMM5 CTL lines were generated following this protocol closely and with consistent results from each. Similar methods were enployed for generation of other CTL lines studied.

Cytotoxicity Assays

Cell-mediated killing was determined in vitro using a 4-h chromium release assay. 51Cr-labeled target cells were plated at $2 \times 10^3$ cells/well in triplicate on 96-well V-bottom plates (Costar, Cambridge, Mass.) with varying numbers of effector cells in a final volume of 250 microl. Wells containing either culture medium and target cells only or 1 M HCl and target cells served as background 51Cr release controls and total release controls, respectively. The plates were centrifuged at 100×g for 3 min and incubated at 37° C. in 5% CO2 for 4 h. The plates were again centrifuged, and 0.20 ml of medium from each well was removed for counting in a gamma counter. The cytotoxic index was calculated as:

$$\frac{Cpm \text{ (experimental)} - cpm \text{ (background)}}{Cpm \text{ (total release)} - cpm \text{ (background)}} \times 100\%$$

Lytic units were calculated for several of the cytotoxicity assays, using a software package prepared by the National Cancer Institute (Bethesda, Md.), which solves for the equation $y=A \times [1-\exp(-kx)]$, where x is the E:T ratio, y is the cytotoxic index, A is the curve maximum, and k is a constant used to calculate the slope of the best fit line. For the purposes of this study, a lytic unit was defined as the number of effector cells needed to mediate 30% lysis of target cells. The number of lytic units was calculated per $10^5$ effector cells (LU30 per $10^5$ cells).

Example I

Extraction of HLA-A2.1-associated Peptides From Melanoma Cells

The human melanoma cells DM6 and DM93 were cultured in 10-chamber cell factories (Nunc, Thousand Oaks, Calif.) in MEM supplemented with 1% FCS and Pen-Strept. In initial experiments, the cells were harvested with 0.03% EDTA in PBS, whereas in later experiments 0.025% trypsin was also included. Trypsinization resulted in more complete harvests and in higher cell viability without any evident change in reconstitution of epitopes or in the peptide profile (data not shown). Peptides bound to the A2 molecules were acid eluted and isolated by centrifuge filtration using a modification of the protocol described by Hunt et al. Cells were washed three times in cold PBS and solubilized in 20 ml, per $10^9$ cells, of 1% NP-40, 0.25% sodium deoxycholate, 174 microg/ml PMSF, 5 microg/ml aprotinin, 10 microg/ml leupeptin, 16 microg/mi pepstatin A, 33 microg/ml iodoacetamide, 0.2% sodium azide, and 0.03 microg/ml EDTA. The mixture was incubated at 4° C. for 1 h, then centrifuged for 1 h at 100,000×g at 4° C. The supernatant was passed through a 0.22-microm filter, then was passed slowly over two protein A-Sepharose (Sigma) columns in series. The first contained GAP-A3 antibody, specific for HLA-A3, as a negative control, whereas the second column contained BB7.2, specific for HLA-A2. The columns were separately washed and eluted with 0.2N acetic acid, pH 2.7. The HLA molecules and peptides were dissociated at pH 2.1 by bringing the solution to 10% acetic acid and boiling 5 min. Peptides were separated from masses of >5 kDa (antibody, class I H chain, beta-2 microglobulin) by centrifugation through an Ultrafree-CL filter (5000 NMWL, Millipore, Bedford, Mass.). Yields of the peptide were estimated from the quantitation of HLA-A2.1 H chain obtained, using SDS-PAGE. The average estimated yield of HLA-A2.1 molecules was 125 microg per $5 \times 10^9$ cells. The quantity of peptide eluted from 1 microg of HLA-A2.1 will hereafter be referred to as 1 U of peptide.

Example II

HPLC Fractionation of Peptide Extracts

The peptide extracts were fractionated by reversed phase high performance liquid chromatography (HPLC) on an Applied Biosystems model 130A (Foster City, Calif.) separation system. Peptide extracts were concentrated to 100 microl on a Speed Vac, injected onto a Brownlee narrow-bore C-18 Aquapore column (2.1 mm×3 cm, A, 7 microm) and eluted with a 40-min gradient of 0 to 60% (v/v) acetonitrile/ 0.085% trifluoracetic acid (TFA) in 0.1% TFA. Fractions were collected at 1-min intervals. Cytotoxicity assays were performed to identify fractions that reconstituted CTL epitopes. For some experiments, reconstituting fractions were divided into two equal parts. The first was injected onto a Brownlee narrow-bore C-18 Aqua-pore column (2.1 mm×3 cm, 300 A, 7 microm) and eluted with a 40-min gradient of 0 to 60% (v/v) acetonitrile in 0.1% HFA that had been adjusted to pH 8.1 with 14.8 M ammonium hydroxide. The second half was injected onto the same type of column and eluted with a 40-min gradient of 0 to 60% (v/v) acetonitrile/0.1% heptafluorobutyric acid (HFBA) in 0.1% HFBA. Fractions for both second dimension separation methods were collected at 1-min intervals. Cytotoxicity assays were again performed to identify fractions that reconstitute CTL epitopes.

Example III

Reconstitution Experiments

Soluble peptide fractions were partially dehydrated on a Speed Vac, reconstituted in assay media (RPMI 1640, 10% FCS, antibiotics), then incubated for 2 h with $2 \times 10^3$ 51Cr-labeled T2 cells in 150 microl/well in 96-well plates. Effector cells were added in 100 microl assay medium to give an E:T ratio of 10:1, and were incubated at 37° C. The remainder of the assay is performed as in standard chromium release assays described above. Wells containing peptide and target cells but no CTL were used as controls to rule out toxicity of the peptides themselves. Except with very acidic fractions 1 to 3, no cytotoxicity was observed with peptide alone; after the first two assays, the pH in these early fractions was adjusted to pH 7 using 1 M NaOH.

Example IV

Generation of Melanoma-specific A2.1-restricted Human CTL

Figure 2A:
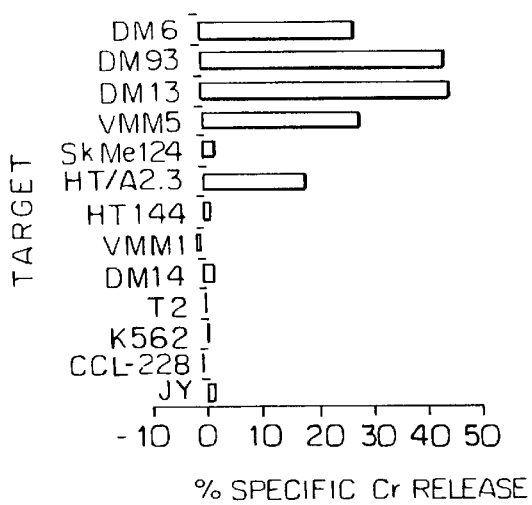
FIGS. 2A and B is a graph illustrating the specificity of VMM5 CTL against a panel of 13 targets.
Figure 2B:
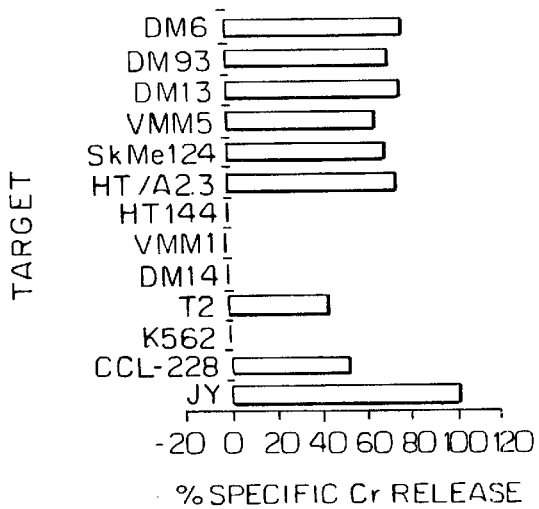

Lymphocytes and melanoma cells harvested from tumor-involved lymph nodes of a patient with metastatic melanoma (VMM5) were cocultured in the presence of rIL-2 and were restimulated biweekly, first with autologous and then with allogenic HLA-A2.1+melanoma. In FIG. 1, the specificity of VMM5 CTL is shown. The CTL were generated as described heretofore in Materials and Methods. Cytotoxic activity was evaluated in a 4-h chromium release assay on the HLA-A2$^+$ melanomas DM6 (solid squares) and DM93 (solid circles), the HLA-A2-melanomas DM14 (open squares) and HT144 (open circles), K562 (solid triangles) and T2 (triangles). Specific lysis of the HLA-A2.1$^+$ melanomas DM6 and DM93 was observed by day 39 of culture, whereas the HLA-A2 negative melanomas DM14 and HT144, the NK target K562, and the HLA-A2.1$^+$ lymphoblastoid Ag-processing-mutant T2 were lysed minimally. This specificity was maintained for at least 4 mo. in culture, during which time the minimal lysis of K562 and T2 diminished further. In assays against a panel of 13 targets, the specific lysis of HLA-A2.1$^+$ melanomas was confirmed, whereas HLA-A2-melanomas and A2$^+$ tumors of other cell types were not lysed. In FIG. 2A, melanoma-specific CTL line VMM5 was assayed in a 4-h chromium release assay on day 94 of culture. In FIG. 2B, the murine CTL clone AX21-9, specific for HLA-A2.1 molecules, was assayed. In both panels, an E:T ratio of 10:1 is represented. The name of the HLA-A2.1 transfectant of HT144 is abbreviated as HT/A2.3. Murine CTL clone AX21-9, which is specific for HLA-A2 expressed on a variety of cell types, did lyse all of the A2$^+$ targets well. These results verify that failure of VMM5 CTL to lyse the A2$^+$ nonmelanomas is not caused by inherent resistance of the targets to CTL lysis. In separate experiments, lysis of additional HLA-A2$^+$ nonmelanomas was minimal as set forth in TABLE I. As illustrated in TABLE II, the CTL lysed both fresh and cultured autologous tumor, but failed to lyse autologous PHA blasts or autologous LPS blasts.

TABLE II

Lysis of autologous targets by VMM5 CTL and murine HLA-A2-specific CTL

| % Specific Effector Cell | Target Cell | Cr-51 Release |
|---|---|---|
| VMM5 CTL | Fresh VMM5 melanoma | 79 |
| | Cultured VMM5 melanoma | 75 |
| | VMM5 PHA blasts | −1 |
| | VMM5 LPS blasts | −3 |
| AT 1-15 CTL | Fresh VMM5 melanoma | 62 |
| | Cultured VMM5 melanoma | 22 |
| | VMM5 PHA blasts | 21 |
| | VMM5 LPS blasts | 20 |

Lysis of the blasts by AT1-15 clones in one experiment is shown in the above table. In additional experiments, lysis of PHA blasts by AX21-9CTL and AT-15 CTL was 80% and 25%, respectively, at an E:T ratio of 20:1, whereas lysis by the VMM5 CTL was 1%. One HLA-A2$^+$ melanoma, SkMel24, was not lysed by VMM5 CTL. The HLA-A2 negative melanoma HT144 was transfected with the A2.1 gene: the resulting transfectant, HT144 A2.03, expressed HLA-A2.1 and was susceptible to lysis by VMM5 CTL, whereas the parent line was not lysed. Thus, VMM5 CTL are a population of melanoma-specific human CTL, restricted by HLA-A2.1 molecules, that resemble other class I-MHC-restricted, human melanoma-specific CTL lines reported in the literature in that they lyse the majority of HLA-A2.1$^+$ melanomas but fail to lyse autologous nonmelanoma cells, HLA-A2$^+$ nonmelanomas, or HLA-A2-melanomas. Similar specifity for HLA-A2$^+$ melanomas has been observed with the other CTL lines studied.

Example V

Identification of Peptide Fractions That Reconstitute Melanoma-specific Epitopes T2 cells were employed in the present invention to test reconstitution of melanoma-specific epitopes by soluble exogenous melanoma-derived peptides. These cells as well as ther cells expressing appropriate HLA molecules and with or without an enhanced presentation of exogenous peptides may be used as functionally equivalent in the context of the invention. In particular, these cells may be used for stimulating lymphocytes in vitro for the purpose of activating CTL for the subsequent administration to a melanoma patient.

Figure 3:
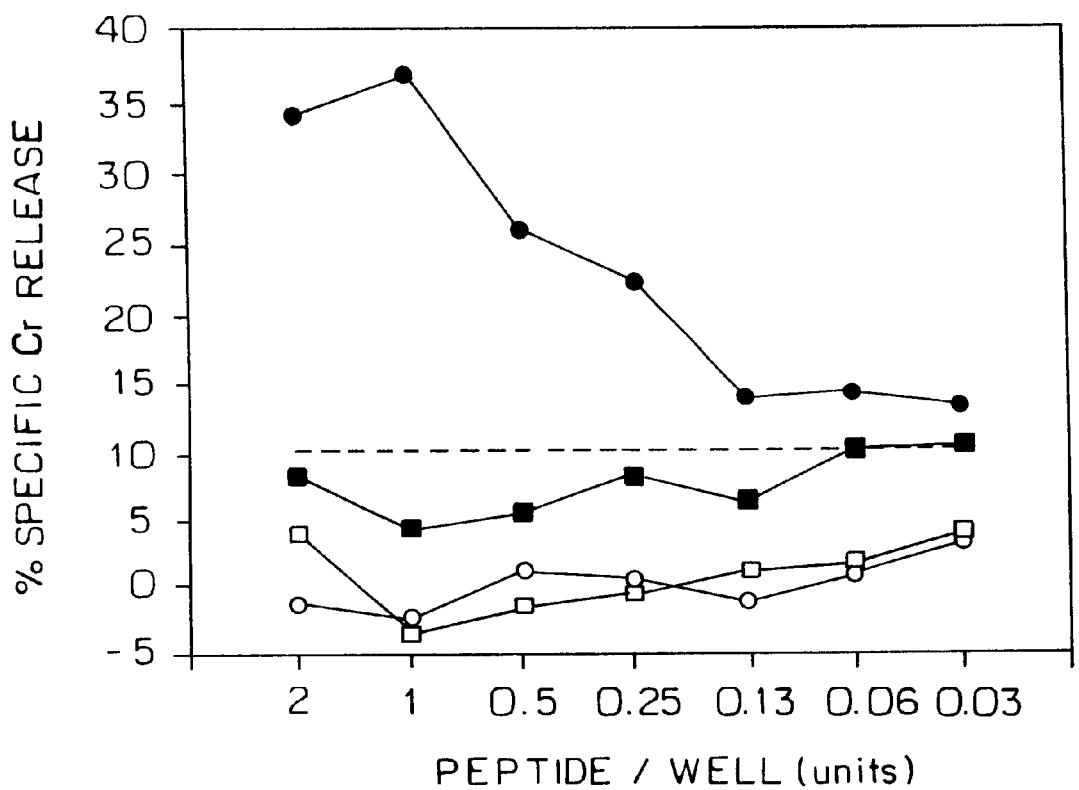
FIG. 3 is a graph of the reconstitution of HLA-A2.1-restricted melanoma-specific epitopes for CTL using peptides eluted from A2.1 molecules on DM93.

Peptides were acid-eluted from affinity-purified HLA-A2.1 molecules isolated from detergent solubilized human melanoma cells. As graphed in FIG. 3, extracts eluted from A2.1 specific (circles) or negative control immunoaffinity columns (squares) were added to 2×10$^3$ 51Cr-labeled T2 cells. The solid symbols represent extracts plus CTL and the open symbols represent extracts alone. One unit of peptide equals that amount of peptide derived from 1 microg of HLA-A2.1 molecules. The dose of negative control extracts is based on cell equivalents, matched to the A2.1 peptide extracts. Lysis of DM93 cells (positive control) was 68%. Unfractionated peptide extract from DM93 cells did reconstitute melanoma-specific epitopes on T2 cells. Maximal lysis of 37% was achieved with 1 U of peptide. Reconstitution of CTL epitopes with unfractionated peptides, but not with negative control extracts, verified the presence in the extract of one or more peptides that reconstitute melanoma-specific epitopes.

Figure 4A:
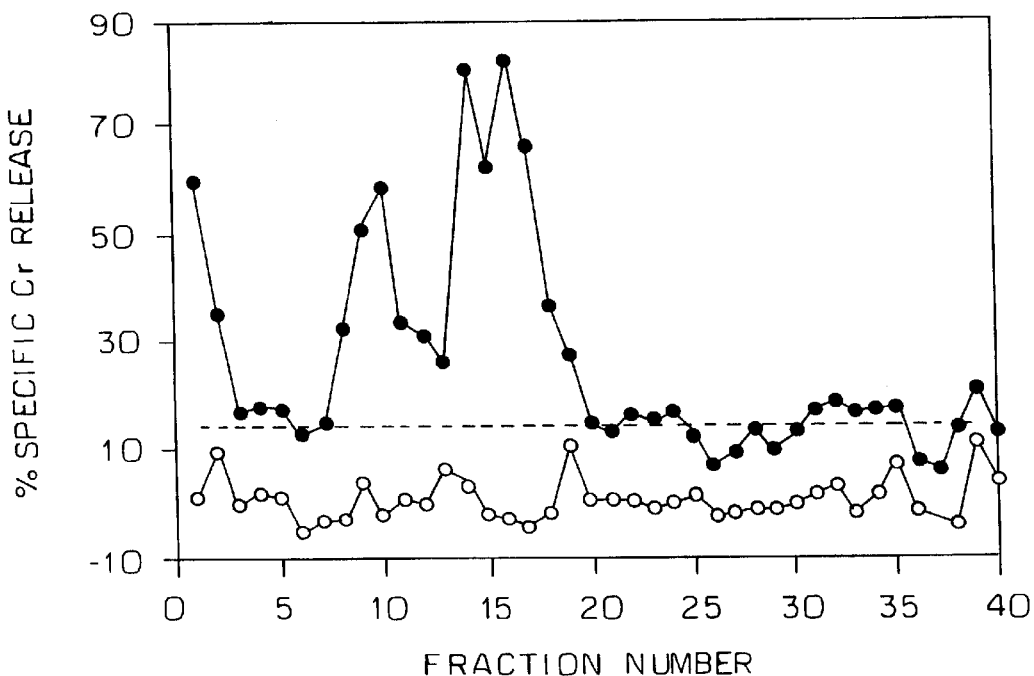
FIGS. 4A and B is a graph of the reconstitution of melanoma-specific epitopes using reversed phase HPLC fractionated peptide extracted from HLA-A2.1 molecules expressed on DM6 cells.
Figure 4B:
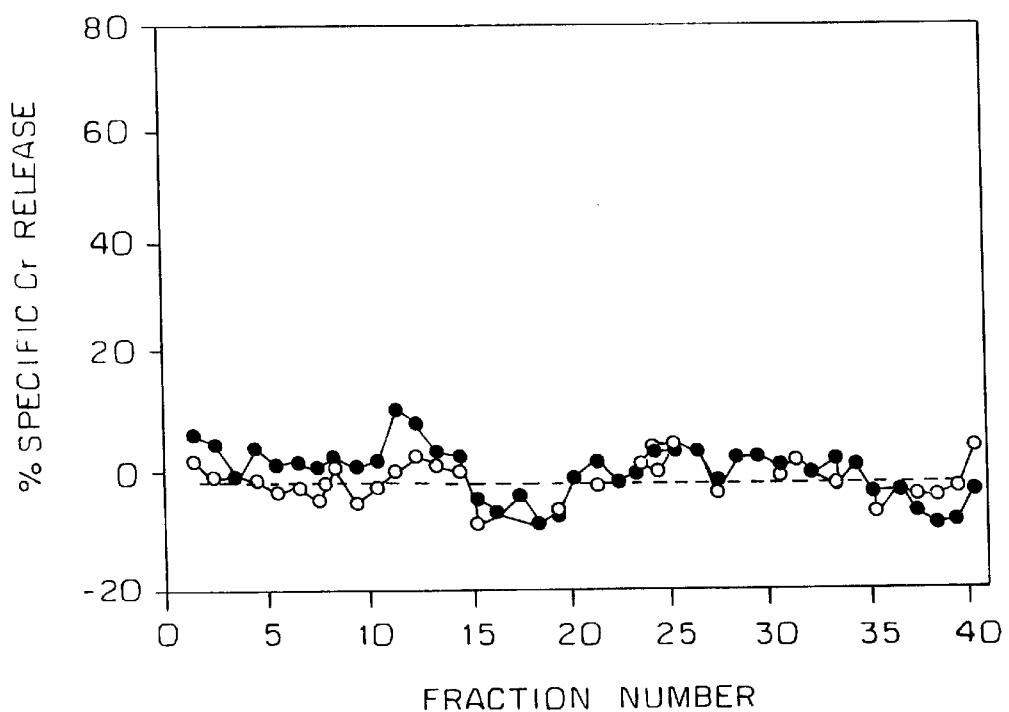
Figure 5A:
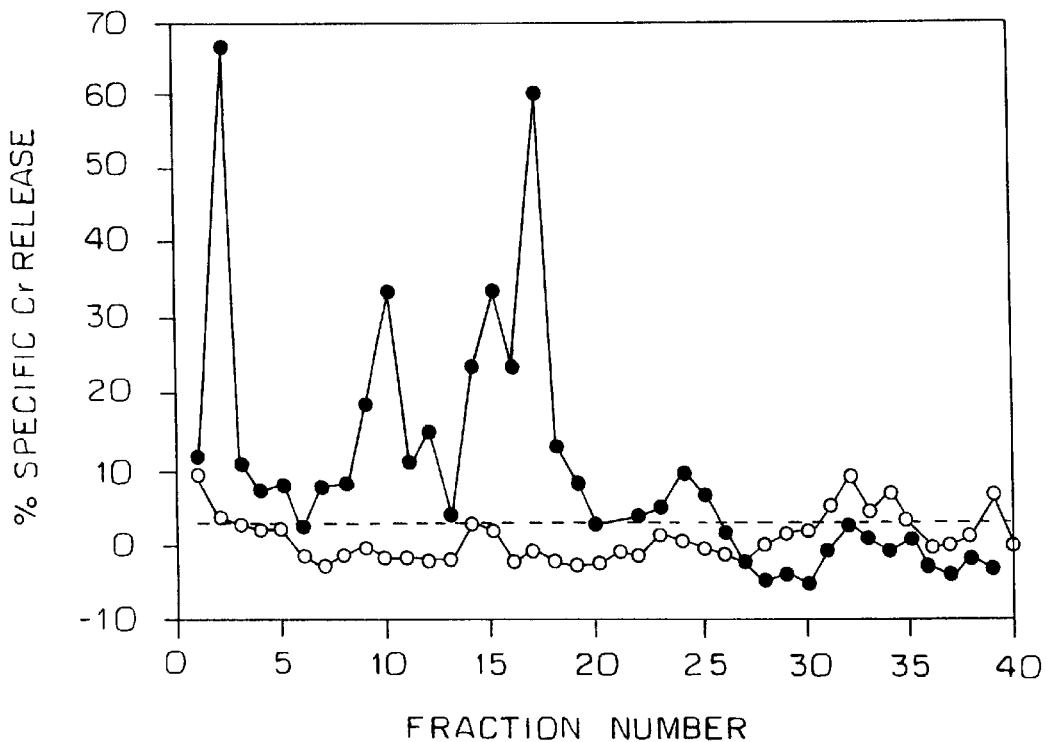
FIGS. 5A and B illustrates in a graph the reconstitution of melanoma-specific epitopes using reversed phase HPLC-fractionated peptide extracted from HLA-A2.1 molecules expressed on DM93 cells.
Figure 5B:
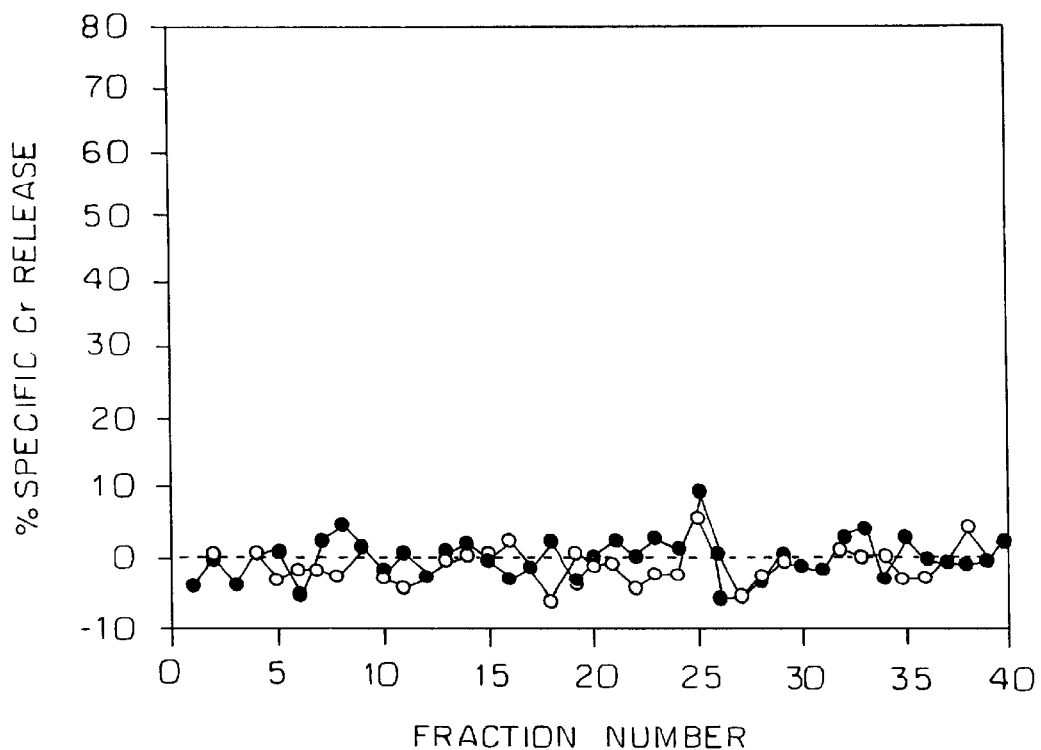

To define further the components responsible for reconstituting CTL epitopes, the mixture of peptides extracted from the A2.1 molecules on DM6 cells was fractionated by reversed phase HPLC, and individual fractions were added to T2 cells, as shown in FIG. 4. Individual HPLC fractions were added to 2×10$^3$ 51Cr-labeled T2 cells and then incubated in the presence (solid circles) or absence (open circles) of melanoma-specific CTL. FIG. 4A illustrates peptides extracted from DM6 cells; FIG. 4B, peptides extracted from lymphoblastoid cells J4; background lyse of T2 cells without peptide is plotted as a horizontal dotted line. Lysis of DM93 cells was 65% in A and 31% in B. Four prominent peaks of reconstitution, A, B, C, and D, located at fractions 1, 10, 14, and 16, respectively are shown in FIG. 4A. A fifth, smaller, peak Bl at fraction 12 was also observed. The specificity of reconstitution with these fractions from DM6 melanoma cells was established by the inability to reconstitute CTL epitopes using HPLC-fractionated peptide extracts from the A2.1 molecules expressed on the EBV-transformed lymphoblastosis cell line, JY shown in FIG. 4B. This pattern of reconstitution observed with DM6-derived peptides was compared to that of another HLA-A2.1$^+$ melanoma cell line, DM93, which had not been used to restimulate these CTL is illustrated in FIG. 5. DM93-derived peptides of FIG. 5A produced the same pattern of multiple peaks of reconstitution that was observed as with DM6 of FIG. 4A. Individual HPLC fractions were added to 2×10$^3$ 51Cr-labeled T2 cells and then incubated in the presence (closed circles) or absence (open circles) of melanoma-specific CTL. A, peptides extracted from an A2.1 specific immunoaffinity column; B, peptides extracted from a negative control immunoaffinity column. Background lysis of T2 is plotted as a horizontal dotted line. Lysis of DM93 cells was 68% in A and 45% in B. From left to right peaks A, B, B1, C, and D are observed in FIG. 5A. The specificity of reconstitution with the A2 extract from DM93 was confirmed by the inability to reconstitute CTL epitopes with HPLC fractions of the negative control extracts, using doses comparable with those used for reconstitution with A2.1-associated peptides from the melanoma cells, as illustrated in FIG. 5B.

Figure 6:
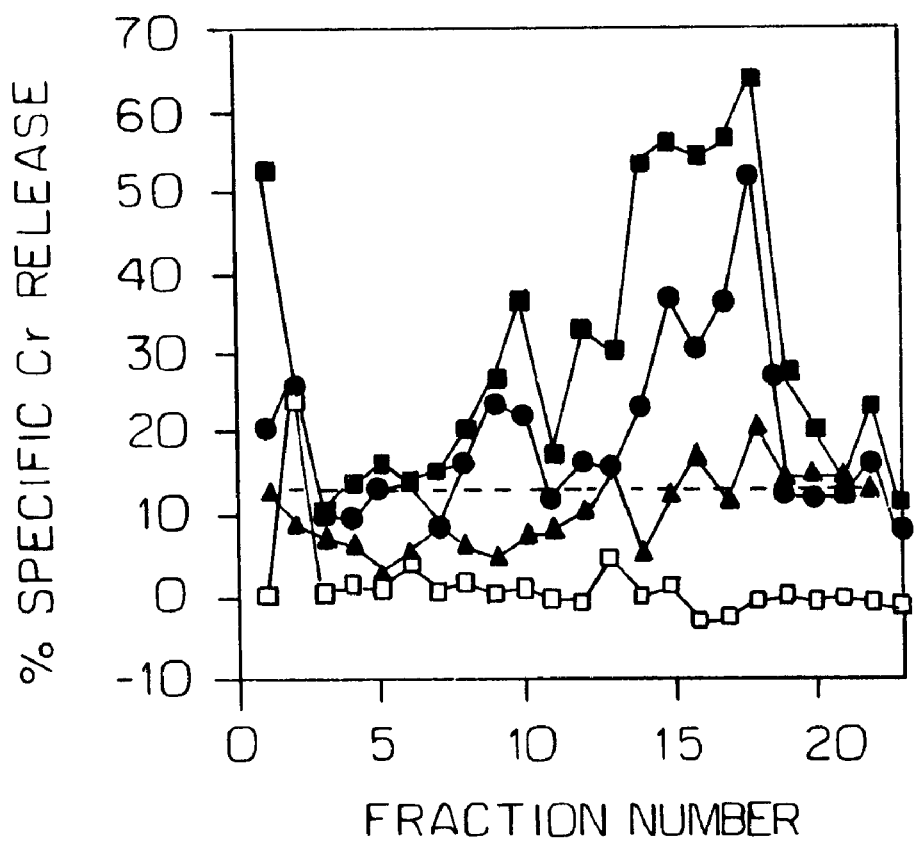
FIG. 6 illustrates graphically the titration of peptide dose for reconstitution.
Figure 7A:
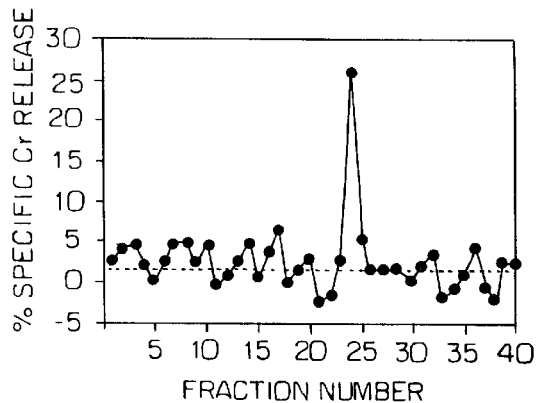
FIGS. 7A–E graphs the second dimension separations of peptide extracts.
Figure 7B:
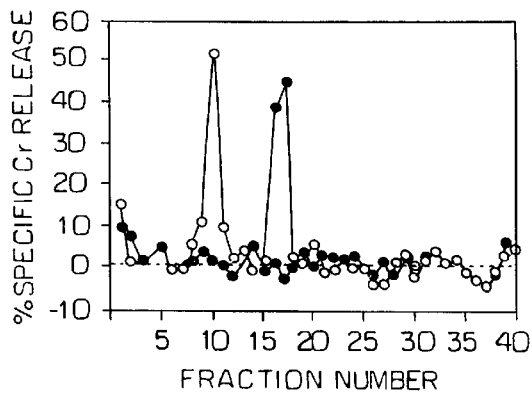
Figure 7C:
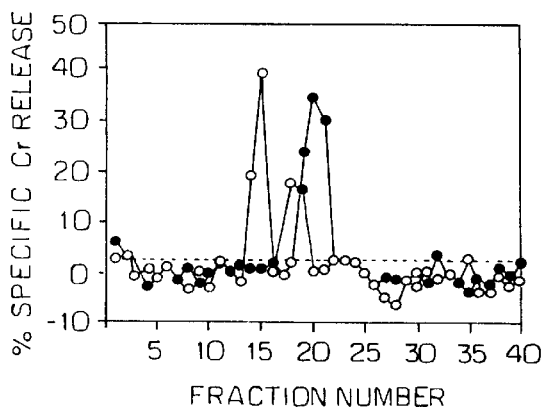
Figure 7D:
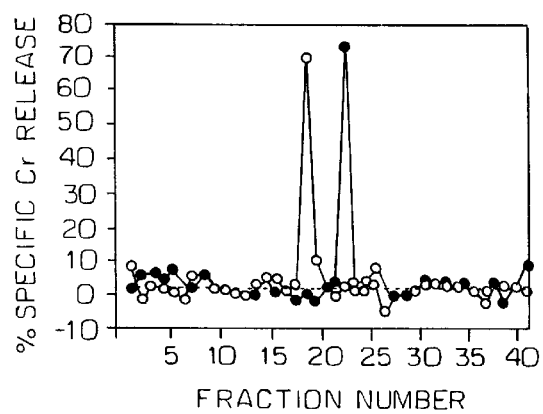
Figure 7E:
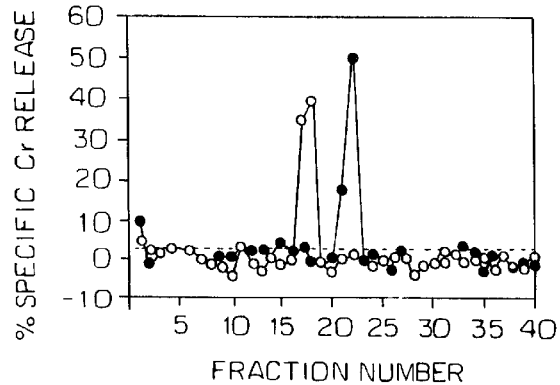

Peptide fractions were used to evaluate reconstitution of CTL epitopes as described in Materials and Methods and illustrated in the graph of FIG. 6. The doses of peptide used were eight (solid squares), 1.25 (solid circles), and 0.25 (solid triangles) units per well. Background lysis of T2 is plotted as a horizontal dotted line. Cells were also incubated with 8 U of peptide without CTL (open squares). Reconstitution for each peak was dose dependent within the range 0.25 to 8 U/well. The pattern of five peaks of reconstitution was observed in six different experiments with five different peptide extracts, using 1 to 10 U of peptide/well. With three additional extracts, all except peak A were present. These data demonstrate that peptides present in multiple HPLC fractions common to two melanoma lines reconstitute epitopes for melanoma-specific CTL.

First dimension HPLC fractions that reconstituted melanoma-specific epitopes on T2 cells were fractionated a second time using either HFA (open squares) or HFBA (solid circles) as an organic modifier, and fractions were evaluated for reconstitution of CTL epitopes by addition to T2 cells, as shown in FIG. 7, A to E,. In each graph, a dotted horizontal line represents the background lysis of T2 cells by CTL only. FIG. 7A shows HFBA separation of 31 U of Peak A peptides from DM93 cells; FIG. 7B HFA and HFBA separations of 22 U of peak B peptides from DM93; FIG. 7C HFA and HFBA separations of 24 U of peak C peptides from DM93; FIG. 7D HFA and HFBA separations of 22 U of peak D peptides from DM93; and FIG. 7E HFA and HFBA separations of 7 U of peak D peptides from DM6. Because of its highly polar nature, peak A was separated using HFBA only. A single reconstituting peak was identified in FIG. 7A. Second dimension separations of peaks B and D revealed a single peak of activity in both HFA and HFBA (FIGS. 7B, 7D, 7E). The activity from peak D appears at identical fractions in HFA and in HFBA for both DM6 and DM93 (FIGS. 7D, 7E). Separation of the peak C HFA resulted in two peaks of reconstitution whereas HFBA gave one broad peak (FIG. 7C). With the resolution of peak C into two peaks, and including peak B1, a total of at least six shared CTL epitopes are demonstrated. These epitopes are labeled A2Mel-A, A2Mel-B, A2Mel-B1, A2Mel-C1, A2Mel-C2, and A2Mel-D.

In the peptide mixture responsible peak B, one peptide was identified as Sequence Tyr Met Asp Gly Thr Met Ser Gin Val, listed hereinafter as SQ. ID No. 9. The peptide is homologous to a portion of the tyroisinase protein except at Position 3 where an Asp(D) is found instead of Asn(N).

Example VI

Peptides Recognized by Melanoma-Specific CTL

HLA-A2.1 molecules were immunoaffinity purified from detergent lysates of the human melanoma cell line DM6. The associated peptides were released by acid extraction, separated from HLA-A2.1 and antibody by filtration, and fractionated by multiple stages of HPLC. At each stage, HPLC fractions containing relevant peptides were identified by testing their ability to reconstitute epitopes for two melanoma-specific CTL lines, VMM5 and DM204-13, after incubation with the HLA-A2.1 positive lymphoblastoid cell line T2 In FIG. 8A peptides bound to A2.1 molecules were extracted and fractionated by reversed-phase HPLC, C. L. Slingluff Jr., et al, J. Immunol. (1993) 50, 2955, by using a gradient of acetonitrile/0.085% trifluoroacetic acid (TFA) in 0.1% TFA with acetonitrile increasing from 0 to 9% (0-5 min), 9 to 36%(5–55min), 36 to 60% (55–62min) (v/v), collecting one-minute fractions. In FIG. 8B Fractions 2 and 3 from the separation shown in panel A were pooled and rechromatographed with a 55 minute gradient of 0 to 30% acetonitrile/0.1% heptafluorobutyric acid (HFBA) in 0.1% HFBA, collecting one-minute fractions. For both panels, peptide fractions were incubated for 2–3 h with $2 \times 10^3$ 51Cr-labelled T2 cells in 150 ll assay media per well in 96-well plates. CTL were added to give an effector:target ratio of 10:1, and a standard chromium release assay was conducted. The panels show lysis of target cells plus peptide by VMM5 CTL (open circles), DM204-13 CTL (closed circles) and media only (solid line without symbols). Lysis of T2 cells without peptide by VMM5 CTL was 0.3% in (A) and 0.8% in (B) and by DM204-13 CTL was 0.7% in (A) and −0.2% in (B), while positive control lysis of HLA-A2$^+$ melanoma cells by VMM5 CTL was 41% in FIG. 8A and 67% in FIG. 8B and by DM204-13 CTL was 28% in FIG. 8A and 78% in FIG. 8B.

Figure 8A:
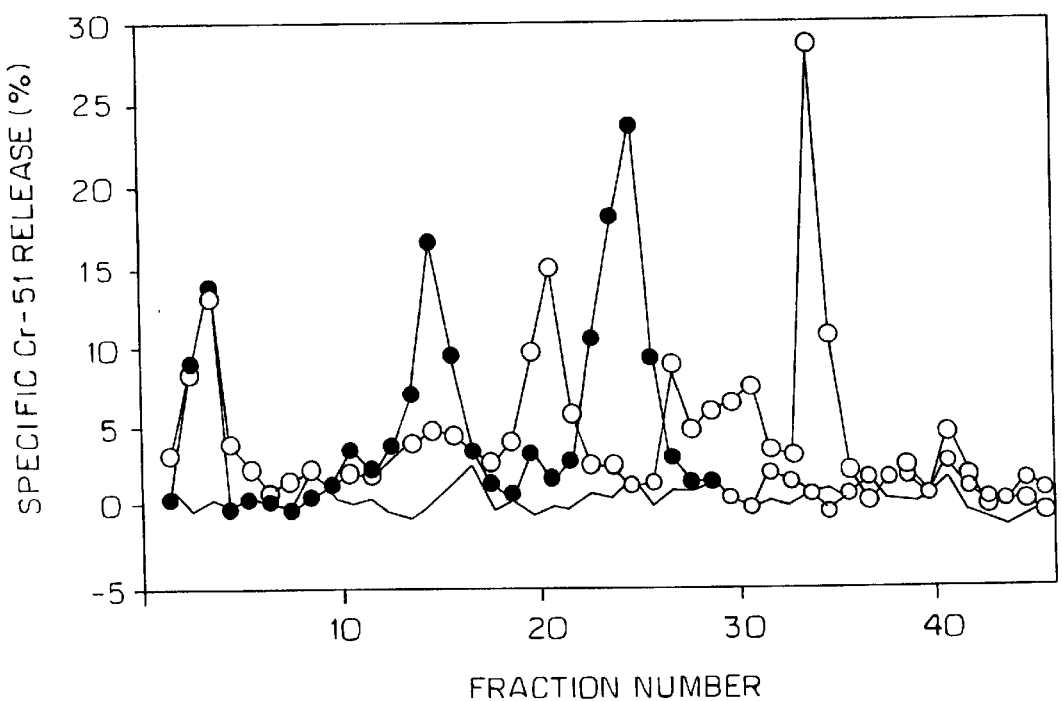
FIGS. 8A and B illustrates the reconstitution of epitopes for two melanoma-specific CTL lines with HPLC fractions derived from naturally processed peptides extracted from HLA-A2.1 molecules.
Figure 8B:
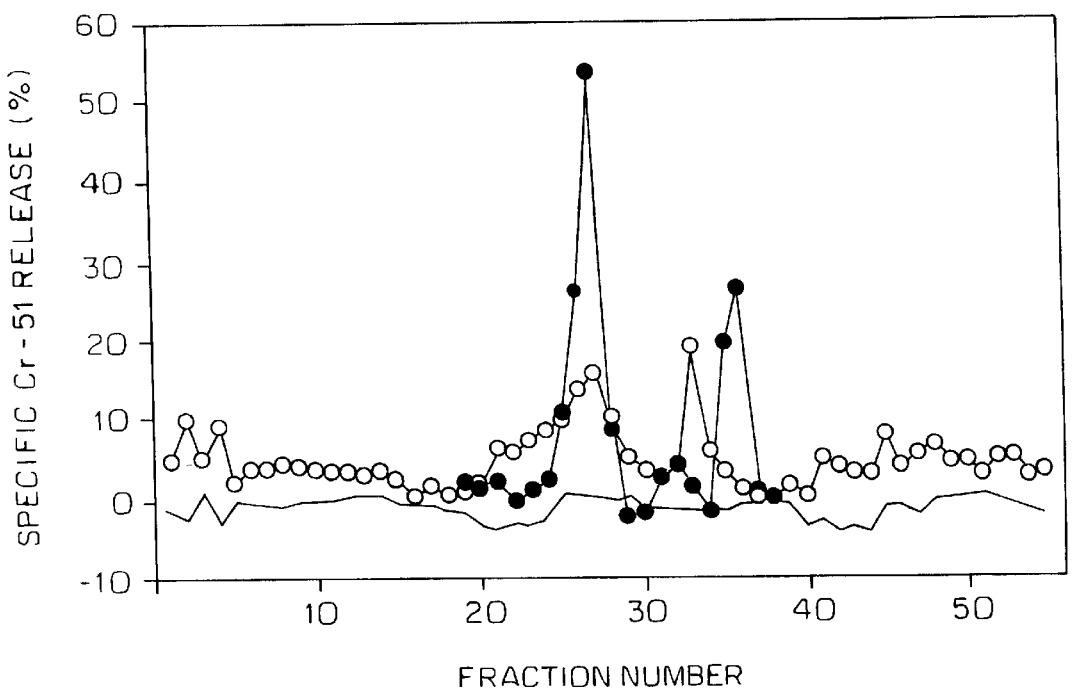

After first dimension HPLC separation, six peaks of activity were identified for VMM5 and three for DM204-13 as shown in FIG. 8A. Fractions 2–3 and 14–15 appeared to contain peptides recognized by both CTL lines. However, several hundred peptides were detected by mass spectrometry in each of the active fractions in this chromatograph. Consequently, fractions 2 and 3 were pooled and submitted to a second separation using HFBA instead of TFA as the organic modifier, FIG. 8B. Two peaks of activity were found for each CTL line, one of which contained peptides recognized by both. The most active fractions in the peak recognized by both CTL lines still contained over 50 peptides. The m/z values for a number of peptides that reconstituted epitopes for each CTL line were determined based on their presence in active fractions and absence in adjacent inactive fractions. The number of candidate peptides exceed the number that could be sequenced with available material.

Figure 9A:
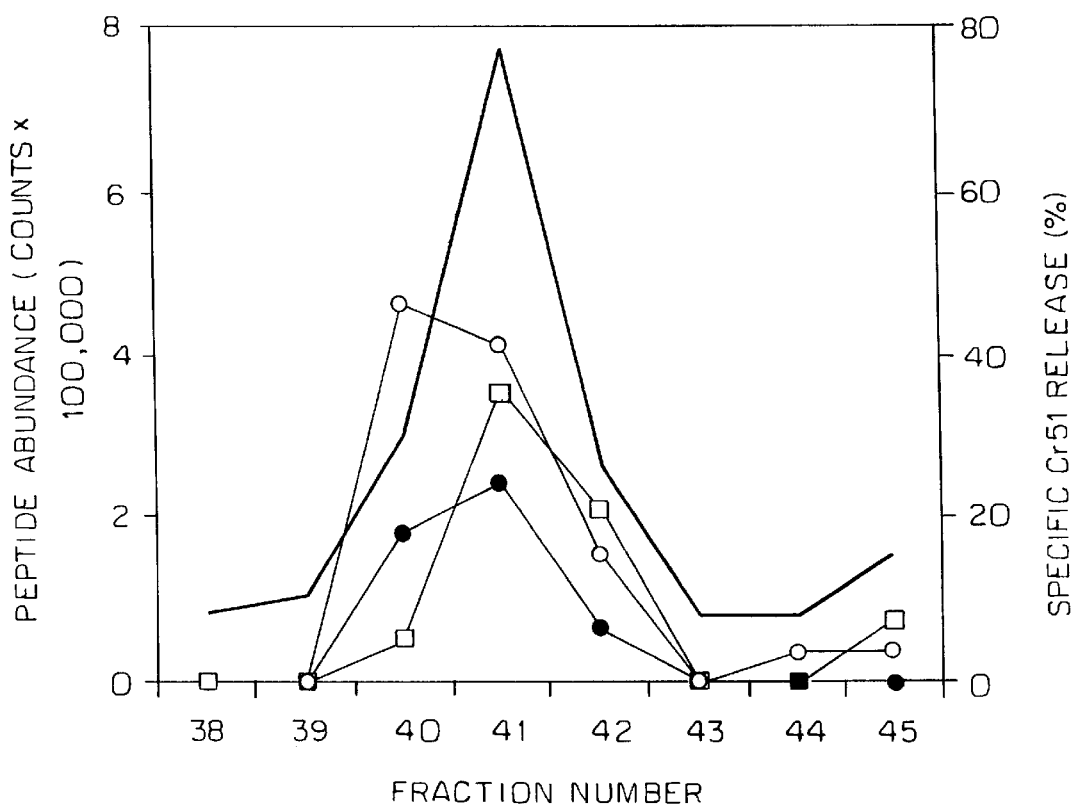
FIGS. 9A and B graphs the identification of candidate peptides by mass spectrometry.
Figure 9B:
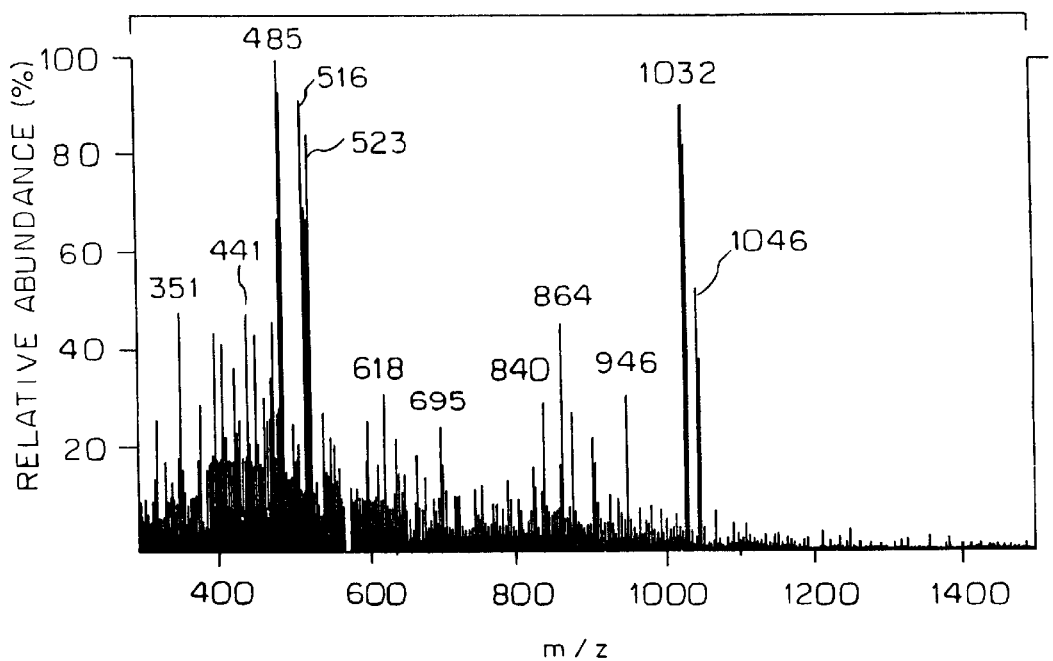

Second dimension HPLC fractions 26 and 27 from FIG. 8B were injected into an electrospray ionization tandem mass spectrometer using a novel online microcapillary column effluent splitter which directs the effluent simultaneously to the mass spectrometer and to the wells of a microtiter plate. Because third dimension separations using standard HPLC methods resulted in large losses of material and failed to reduce significantly the number of candidate peptides, a specific apparatus was constructed. A PRP-1-(Hamilton) microcapillary HPLC column (100 μm by 22 cm) was butt-connected using a zero dead volume union (Valco) to two small capillaries of different lengths and interior diameters (25 μm and 40 μm ID, Polymicro Technologies). The column was eluted into the union with a 34 minute gradient of 0 to 60% acetonitrile. The 20 Am capillary deposited ⅙ of the material into 50 μl of culture media in microtiter plate wells. The larger of the two capillaries directed the remaining ⅚ of the material into the electrospray ionization source, and mass spectra of the peptides deposited in each well were recorded on a Finnigan-MAT (San Jose, Calif.) triple quadrupole mass spectrometer, R. A. Henderson et al., Proc. Natl. Acad. Sci. USA 90, 10275 (1993). A subsequent chromium release assay identified the wells containing peptide epitopes. Second dimension HPLC fractions 26 and 27 were pooled and analyzed using this apparatus. Both CTL lines showed a single peak of activity. Mass spectra showed that these fractions contained approximately 50 peptides (FIG. 9A), but the relative abundances of only three of these (with m/z values of 1046, 946 and 864) matched the activity profile for DM204-13 (FIG. 9B). In FIG. 9A, the summation of mass spectra recorded on peptides deposited in well 41 are illustrated. Many of these were eliminated as candidates because their relative abundance failed to correlate with the observed lysis. In FIG. 9B the bold solid line indicates percent lysis as determined by chromium release assay. Peptide amount, as indicated by ion abundance, is plotted for m/z 1046 (open circles), m/z 946 (solid circles), and m/z 864 (open squares)

Figure 10A:
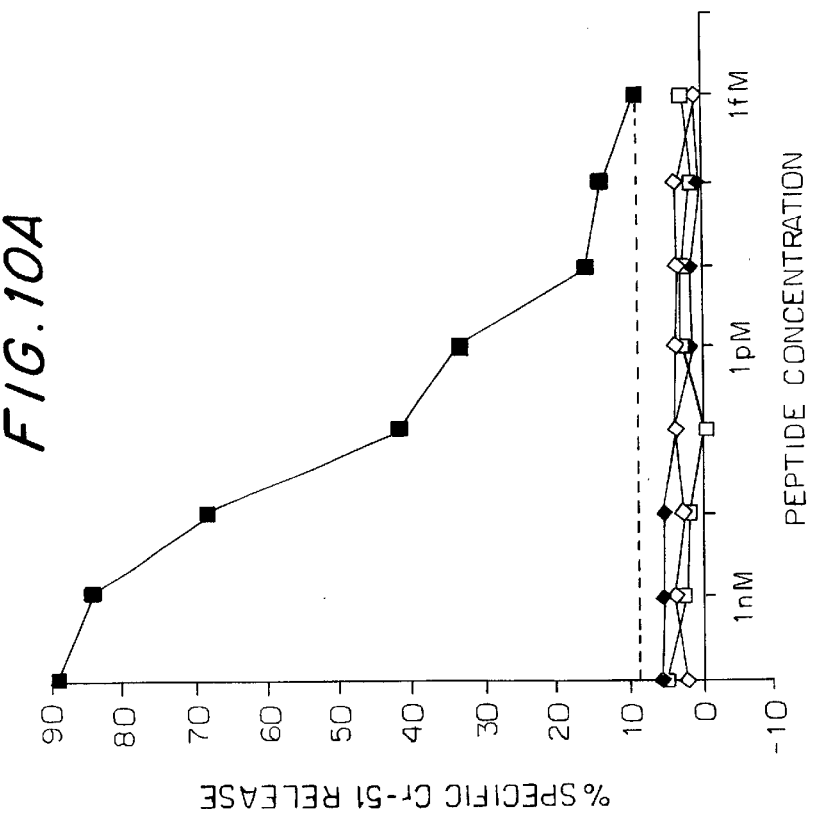
FIGS. 10A and B illustrates the dose-titration curves for synthetic peptides.
Figure 10B:
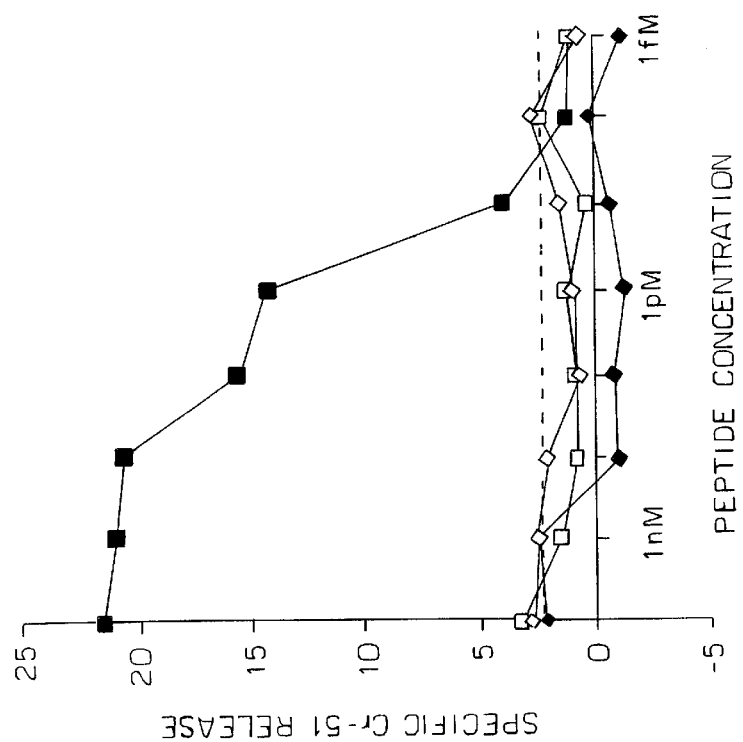

Collision-activated dissociation analyses performed on the $(M+H)^+$ ions for each of these three peptides defined their amino acid sequences as: m/z 864, Ser Met Ala Pro Gly Asn Thr Ser Val (SEQ ID NO:88); 946 Tyr Xaa Glu Pro Gly Pro Val Thr Ala (SEQ ID NO:93); and 1046, Ala Xaa Tyr Asp Ala Thr Tyr Glu Thr (SEQ ID NO:89); where X=L or I; The sequenced peptides were synthesized, using an equimolar mixture of Leu and Ile in place of X. The ability to reconstitute an epitope for melanoma specific CTL VMM5, and DM204-13, illustrated in FIGS. 10A and 10B, is shown for peptides 946 (closed squares), 864 (open squares), and 1046 (open circles). Lysis of T2 without peptide is represented by a horizontal dotted line. As shown in FIG. 10, peptide 946 reconstituted the epitopes for both VMM5 and DM204-13, with half-maximal reconstitution achieved between 1 and 10 pM. When tested independently, both Tyr Leu Glu Pro Gly Pro Val Thr Ala (SEQ ID NO:14) and Tyr Ile Glu Pro Gly Pro Val Thr Ala (SEQ ID NO:39) effectively reconstituted the epitope for VMM5 at similar concentrations. Peptides 864 and 1046 had no effect at concentrations up to 10 nM. The amount of peptide 946 present in well 41 in the experiment shown in FIG. 9B corresponded to a concentration of 8 pM, indicating that the synthetic 946 peptide sensitized at doses comparable to that of the naturally occurring species.

Peptide 946 reconstitutes T cell recognition at concentrations that are at least two orders of magnitude lower than those of several optimized HLA-A2.1 restricted epitopes of viral or cellular origin. The antigenicity of this peptide could be explained by high affinity for the MHC or high affinity of the TcR. The ability of the test peptides to compete with the radiolabeled standard peptide Phe Leu Pro Ser Asp Tyr Phe Pro Ser Val (SEQ ID NO:97) for binding to purified HLA-A2.1 molecules was measured using an equilibrium binding assay, J. Ruppert et al., Cell 74, 929 (1993) and Y. Chen et al., J. Immunol. in press (1994) with (Open Squares) Try Leu Glu Pro Gly Pro Val Thr Ala (SEQ ID NO:14) (peptide 946L); (solid diamonds) Tyr Ile Glu Pro Gly Pro Val Thr Ala (SEQ ID NO:39) (peptide 946I); (solid squares) Ala Leu Trp Gly Phe Phe Pro Val Leu (SEQ ID NO:94) another endogenous peptide isolated from HLA-A2.1, R. A. Henderson et al., Proc. Natl. Acad. Sci. USA 90, 10275 (1993); (open diamonds), Ala Pro Arg Thr Val Ala Leu Thr Ala (SEQ ID NO:95), an endogenous peptide isolated from HLA-B7, E. L. Huczko et al., J. Immunol. 151, 2572 (1993). The concentrations giving 50% inhibition of binding of a standard peptide to purified HLA-A2.1 molecules were 1.06 microM and 13.7 microM for the Leu and Ile version of the 946 peptide, respectively as illustrated in the graph of FIG. 11. While the Leu version of 946 contains the predicted motif residues at positions 2 and 9 that support peptide binding to HLA-A2.1, the substitution of Ile at position 2 is expected to lower affinity by about a factor of 10. However, both of these values lie well outside the 5–30 nM range observed for several other naturally processed peptides, and indicate the 946 isomers have considerably lower affinities. This may be due in part to the presence of a negatively charged residue at position 3, which is predicted to have a detrimental effect on binding. In keeping with the low affinity of peptide 946 for HLA-A2.1, this molecule is not present in high copy number on the cell surface. The sequence of 946 was obtained from 15 fmol of peptide present in a second dimension HPLC fraction representative of $4 \times 10^{10}$ DM6 cells. Assuming a 5% overall yield through purification and extraction and 3 HPLC separations, it is calculated that 946-HLA-A2.1 complexes are present at only 5 copies per melanoma cell. This number is well below the 50–200 copies/cell estimated to be necessary for T cell recognition. It is conceivable that, due to the low affinity of 946 for the HLA-A2.1 molecule, the peptide may have been disproportionately lost during the washes that accompany the affinity purification procedure. Regardless, the ability of this peptide to sensitize for CTL-mediated lysis at concentrations that are $10^4$–$10^5$ lower than the $IC_{50}$ value indicates that CTL lines VMM5 and DM204-13 have an extremely high affinity for this epitope.

Figure 12:
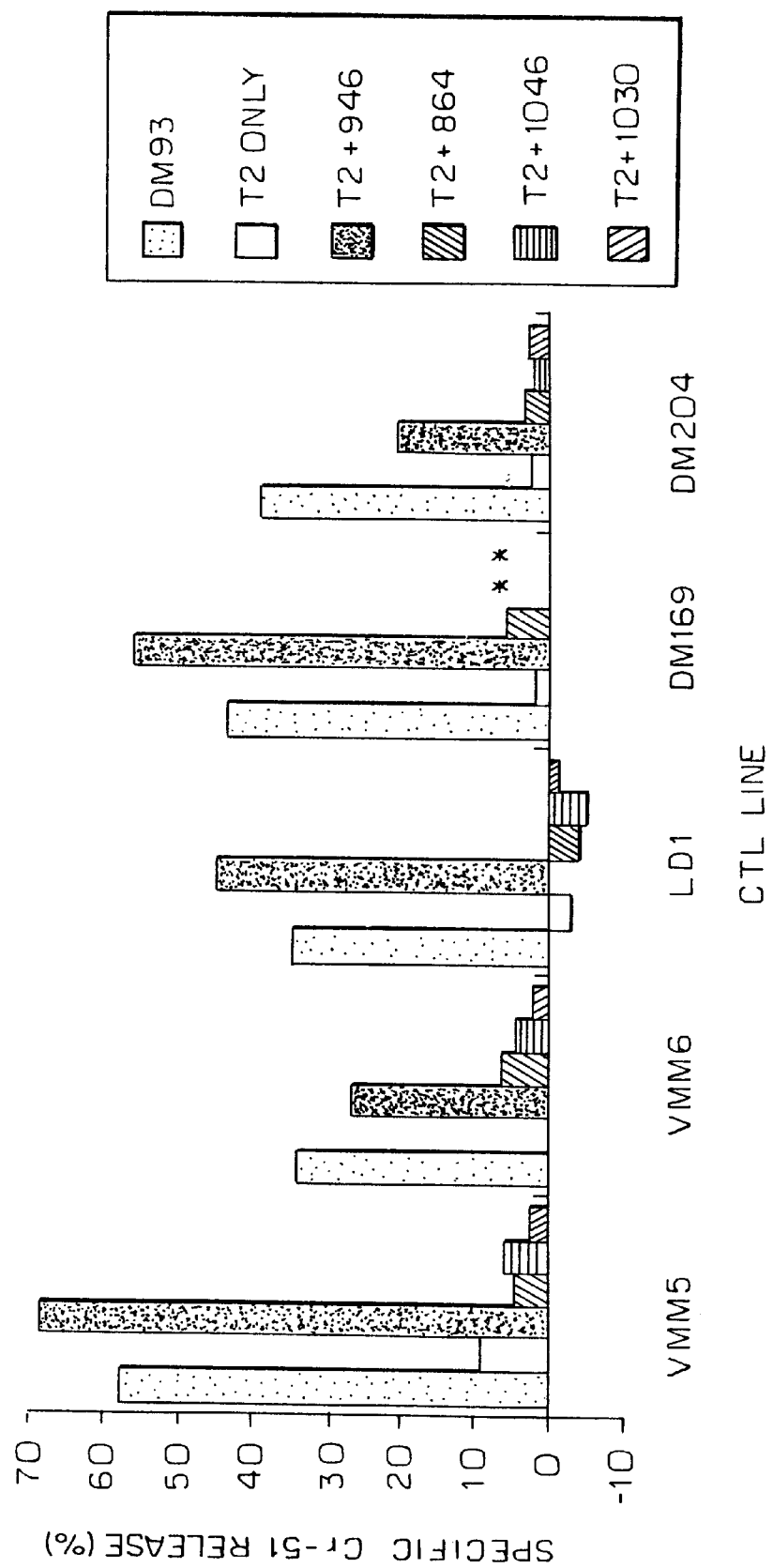
FIG. 12 illustrates the peptide 946 reconstitutes epitope for 5 melanoma-specific CTL lines in a standard chromium release assay.

To determine whether peptide 946 was a generally relevant epitope for HLA-A2.1 restricted melanoma specific CTL, lines from 3 additional patients were tested. CTL lines VMM5 and VMM6 were generated by stimulation with autologous tumor. VMM5 CTL were maintained on allogeneic A2.1+ melanoma DM6 after specificity was obtained, C. L. Slingluff Jr. et al., J. Immunol. 150, 2955 (1993). DM169-13 and DM204-13 CTL were generated by stimulation with allogeneic A2.1+ melanoma DM13, N. J. Crowley et al., J. Immunol. 146, 1692 (1991), then maintained with DM6. LD1 CTL were stimulated on a rotating schedule of stimulating logeneic A2.1+ melanomas DM6, DM13, and DM93. DM93 is an HLA-A2.1+ melanoma used as a positive control. Peptides were synthesized by solid phase Fmoc chemistry on Wang resins with a Gilson (Middleton, Wis.) Model AMS 422 multiple peptide synthesizer. T2 cells were preincubated with the peptides whose $(M+H)^+$ values are indicated in the legend, FIG. 12. Peptide 946 was used at a concentration of 0.1 nM, except 1 nM for DM169. All other peptides were used at a concentration of 10 nM except 250 nM for DM169 and 0.1 nM for LD1. Asterisks (*) mark peptides not evaluated. The sequences of the peptides 864 (Seq. ID No. 88), 946 (Seq. ID No. 39), 1046 (Seq. ID No. 89) are described in the text. Peptide 1030 has the sequence Tyr Met Asp Gly Thr Met Ser Gln Val (SEQ ID NO:90), (related to peptide from tyrosinase. molecule). The 946 peptide, at concentrations of 0.1–1 nM, shown in FIG. 12, reconstituted recognition by each of these 3 lines, while neither 864 nor 1046 had any detectable activity at equal or higher concentrations. Dose response curves obtained for two of these lines showed half-maximal lysis in the 1–10 pM range. These results establish that 5 out of 5 patients examined had high affinity t-cells that recognized the HLA-A2.1-associated peptide 946. An additional peptide Try Met Asn Gly Thr Met Ser Gln Val (SEQ ID NO 96), which originates from tyrosinase and had been identified by Boon and colleagues as an HLA-A2.1 restricted melanoma specific T cell epitope, was also evaluated. None of 4 CTL lines recognized cells incubated with this peptide.

These five CTL lines were established in two different laboratories using varied stimulation protocols and several different stimulating tumors. Most were stimulated initially with autologous tumor (VMM6, VMM5) or allogeneic A2.1+ melanoma DM13 (DM169-13, DM204-13), although many were maintained on DM6 after specificity was obtained. None of the CTL lines was stimulated exclusively with DM6, the line from which the 946 peptide was identified. The VMM6 CTL line was stimulated exclusively with autologous fresh cryopreserved tumor. Its recognition of 946 is evidence that the T-cell response to that peptide does not require stimulation with DM6, and that fresh VMM6 melanoma cells must is present the 946 peptide in a manner that induces a CTL response. The fact that all five lines recognize this 946 peptide despite their varied origins is strong evidence that this peptide may be capable of stimulating a CTL response in a large number of HLA-A2.1+ individuals.

A search of DNA and protein sequence data banks failed to identify a likely precursor protein for peptide 864. Peptide 1046 was found in cofilin, an actin-modulating protein that is ubiquitously expressed in mammalian cells, K. Ogawa et al., Nucleic Acids Research 18, 7169 (1990). The Leu containing version of peptide 946 (Seq. ID No. 14) was found in a protein identified as Pmel-17, B. S. Kwon et al., Proc. Natl. Acad. Sci. USA 88, 9228 (1991; B. S. Kwon et al., Molecular Biology and Medicine 4, 339 (1987). Pmel-17 is a 645 amino acid protein expressed in melanocytes and melanoma and has not been detected in nonpigmented cells, B. S. Kwon et al., Proc. Natl. Acad. Sci. USA 88, 9228 (1991; B. S. Kwon et al., Molecular Biology and Medicine 4, 339 (1987). Although its function is unknown, it has been postulated to be a component of the melanin biosynthetic pathway, B. S. Kwon et al., Proc. Natl. Acad. Sci. USA 88, 9228 (1991); B. S. Kwon et al., Molecular Biology and Medicine 4, 339 (1987). Its presence in melanocytes as well as melanoma is consistent with the observation that some melanoma specific CTL clones recognize melanocytes, A. Anichini et al, J. Exp. Med. 177, 989 (1993). This observation, coupled with the fact that spontaneous remissions of human melanoma have been observed in conjunction with the simultaneous development of vitiligo, T. C. Everson and W. H. Cole, Eds., Spontaneous Regression of Cancer (W. B. Saunders Company, Philadelphia, 1966), suggests that an autoimmune response directed against melanocytes may be a natural accompaniment to the development of immunity to melanoma. Although we do not yet have evidence that 946-specific CTL recognize normal melanocytes, the possibility that 946 is one of the epitopes responsible for cross-reactivity of melanoma-specific CTL with normal melanocytes raises questions about the relationship between tumor immunity and autoimmunity.

Example VII

After identification of a melanoma specific CTL epitope from the protein PMEL17 (Tyr-Xaa-Glu-Pro-Gly-Pro-Val-Thr-Ala(SEQ ID NO: 93), wherein Xaa is Ile or Leu) (PEPTIDE 946I or 946L), other possible epitopes consisting of 9, 10, or 11 amino acids from PMEL17 were synthesized. To select possible epitopes, A2.1 motif information previously generated previously was used. A Gilson AMS 422 Multiple Peptide Synthesizer was used to make the synthetic peptides, which permits synthesis of only 48 peptides at one time. Due to the need to synthesize other peptides, the first set of peptides derived from PMEL17 was synthesized and contained 38 nonamers with Leu, Ile, or Met at position 2 and Leu, Ile, Val, or Ala at position 9. The sequences of these nonamers are shown below. They include the two versions of the biologically active peptide Tyr-Xaa-Glu-Pro-Gly-Pro-Val-Thr-Ala, wherein Xaa=Leu or Ile, one version with Leu at Position 2 (Seq. Id. No. 14) and one version with Ile at Position 2 (Seq. Id. No. 39). The second batch synthesized included nonamers with Thr at the ninth position, as well as 10 and 11 mers with Leu or Met at position 2 and Leu, Ile, Val, Ala, or Thr at position 9. Not all of the 11 mers with this motif were synthesized. The list of these peptides is also shown below.

Example VIII

Peptides synthesized 9-mers

SEQ. ID. NO. 1  Asp—Leu—Val—Leu—Lys—Arg—Cys—Leu—Leu

SEQ. ID. NO. 2  Leu—Leu—His—Leu—Ala—Val—Ile—Gly—Ala

SEQ. ID. NO. 3  His—Leu—Ala—Val—Ile—Gly—Ala—Leu—Leu

SEQ. ID. NO. 4  Leu—Leu—Ala—Val—Gly—Ala—Thr—Lys—Val

SEQ. ID. NO. 5  Gln—Leu—Tyr—Pro—Glu—Trp—Thr—Glu—Ala

SEQ. ID. NO. 6  Val—Ile—Trp—Val—Asn—Asn—Thr—Ile—Ile

SEQ. ID. NO. 7  Val—Leu—Gly—Gly—Pro—Val—Ser—Gly—Leu

SEQ. ID. NO. 8  Gly—Leu—Ser—Ile—Gly—Thr—Gly—Arg—Ala

SEQ. ID. NO. 9  Tyr—Met—Asp—Gly—Thr—Met—Ser—Gln—Val

SEQ. ID. NO. 10  Ser—Ile—Gly—Thr—Gly—Arg—Ala—Met—Leu

SEQ. ID. NO. 11  Met—Leu—Gly—Thr—His—Thr—Met—Glu—Val

SEQ. ID. NO. 12  Gln—Leu—His—Asp—Pro—Ser—Gly—Tyr—Leu

SEQ. ID. NO. 13  Thr—Leu—Ile—Ser—Arg—Ala—Pro—Val—Val

SEQ. ID. NO. 14  Tyr—Leu—Glu—Pro—Gly—Pro—Val—Thr—Ala

SEQ. ID. NO. 15  Gly—Met—Thr—Pro—Glu—Lys—Val—Pro—Val

SEQ. ID. NO. 16  Gly—Met—Thr—Pro—Ala—Glu—Val—Ser—Ile

SEQ. ID. NO. 17  Ser—Ile—Thr—Gly—Ser—Leu—Gly—Pro—Leu

SEQ. ID. NO. 18  Pro—Leu—Leu—Asp—Gly—Thr—Ala—Thr—Leu

Peptides synthesized

SEQ. ID. NO. 19: Thr—Leu—Arg—Leu—Val—Lys—Arg—Gln—Val

SEQ. ID. NO. 20: Arg—Leu—Val—Lys—Arg—Gln—Val—Pro—Leu

SEQ. ID. NO. 21: Asp—Ile—Val—Gln—Gly—Ile—Glu—Ser—Ala

SEQ. ID. NO. 22: Val—Leu—Pro—Ser—Pro—Ala—Cys—Gln—Leu

SEQ. ID. NO. 23: Ser—Leu—Ala—Asp—Thr—Asn—Ser—Leu—Ala

SEQ. ID. NO. 24: Ser—Leu—Ala—Val—Val—Ser—Thr—Gln—Leu

SEQ. ID. NO. 25: Gln—Leu—Ile—Met—Pro—Val—Pro—Gly—Ile

SEQ. ID. NO. 26: Leu—Ile—Met—Pro—Val—Pro—Gly—Ile—Leu

SEQ. ID. NO. 27: Ile—Met—Pro—Val—Pro—Gly—Ile—Leu—Leu

SEQ. ID. NO. 28: Gly—Ile—Leu—Leu—Thr—Gly—Gln—Glu—Ala

SEQ. ID. NO. 29: Leu—Leu—Thr—Gly—Gln—Glu—Ala—Gly—Leu

SEQ. ID. NO. 30: Gly—Leu—Gly—Gln—Val—Pro—Leu—Ile—Val

SEQ. ID. NO. 31: Pro—Leu—Ile—Val—Gly—Ile—Leu—Leu—Val

SEQ. ID. NO. 32: Leu—Ile—Val—Gly—Ile—Leu—Leu—Val—Leu

SEQ. ID. NO. 33: Gly—Ile—Leu—Leu—Val—Leu—Met—Ala—Val

SEQ. ID. NO. 34: Ile—Leu—Leu—Val—Leu—Met—Ala—Val—Val

SEQ. ID. NO. 35: Leu—Leu—Val—Leu—Met—Ala—Val—Val—Leu

SEQ. ID. NO. 36: Leu—Met—Ala—Val—Val—Leu—Ala—Ser—Leu

SEQ. ID. NO. 37: Arg—Leu—Met—lys—Gln—Asp—Phe—Ser—Val

SEQ. ID. NO. 38: Pro—Ile—Gly—Glu—Asn—Ser—Pro—Leu—Leu

SEQ. ID. NO. 39: Tyr—Ile—Glu—Pro—Gly—Pro—Val—Thr—Ala

10 mers

SEQ. ID. NO. 40: Val—Leu—Lys—Arg—Cys—Leu—Leu—His—Leu—Ala

SEQ. ID. NO. 41: Cys—Leu—Leu—His—Leu—Ala—Val—Ile—Gly—Ala

SEQ. ID. NO. 42: Leu—Leu—His—Leu—Ala—Val—Ile—Gly—Ala—Leu

SEQ. ID. NO. 43: His—Leu—Ala—Val—Ile—Gly—Ala—Leu—Leu—Ala

SEQ. ID. NO. 44: Ala—Leu—Leu—Ala—Val—Gly—Ala—Thr—Lys—Val

SEQ. ID. NO. 45: Trp—Leu—Gly—Val—Ser—Arg—Gln—Leu—Arg—Thr

SEQ. ID. NO. 46: Arg—Leu—Asp—Cys—Trp—Arg—Gly—Gly—Gln—Val

SEQ. ID. NO. 47: Ser—Leu—Lys—Val—Ser—Asn—Asp—Gly—Pro—Thr

SEQ. ID. NO. 48: Ala—Leu—Asn—Phe—Pro—Gly—Ser—Gln—Lys—Val

SEQ. ID. NO. 49: Ala—Met—Leu—Gly—Thr—His—Thr—Met—Glu—Val

SEQ. ID. NO. 50: Met—Leu—Gly—Thr—His—Thr—Met—Glu—Val—Thr

SEQ. ID. NO. 51: Pro—Leu—Ala—His—Ser—Ser—Ser—Ala—Phe—Thr

SEQ. ID. NO. 52: Ala—Leu—Asp—Gly—Gly—Asn—Lys—His—Phe—Leu

SEQ. ID. NO. 53: Phe—Leu—Arg—Asn—Gln—Pro—Leu—Thr—Phe—Ala

SEQ. ID. NO. 54: Gln—Leu—His—Asp—Pro—Ser—Gly—Tyr—Leu—Ala

SEQ. ID. NO. 55: Tyr—Leu—Ala—Glu—Ala—Asp—Leu—Ser—Tyr—Thr

| | Peptides synthesized |
|---|---|
| SEQ. ID. NO. 56 | Thr—Leu—Ile—Ser—Arg—Ala—Pro—Val—Val—Thr |
| SEQ. ID. NO. 57 | Pro—Leu—Thr—Ser—Cys—Gly—Ser—Ser—Pro—Val |
| SEQ. ID. NO. 58 | Thr—Leu—Ala—Glu—Met—Ser—Thr—Pro—Glu—Ala |
| SEQ. ID. NO. 59 | Gly—Met—Thr—Pro—Ala—Glu—Val—Ser—Ile—Val |
| SEQ. ID. NO. 60 | Val—Leu—Ser—Gly—Thr—Thr—Ala—Ala—Gln—Val |
| SEQ. ID. NO. 61 | Ser—Leu—Gly—Pro—Leu—Leu—Asp—Gly—Thr—Ala |
| SEQ. ID. NO. 62 | Leu—Leu—Asp—Gly—Thr—Ala—THr—Leu—Arg—Leu |
| SEQ. ID. NO. 63 | Val—Leu—Tyr—Arg—Tyr—Gly—Ser—Phe—Ser—Val |
| SEQ. ID. NO. 64 | Glu—Leu—Thr—Val—Ser—Cys—Gln—Gly—Gly—Leu |
| SEQ. ID. NO. 65 | Gly—Leu—Pro—Lys—Glu—Ala—Cys—Met—Glu—Ile |
| SEQ. ID. NO. 66 | Val—Leu—Pro—Ser—Pro—Ala—Cys—Gln—Leu—Val |
| SEQ. ID. NO. 67 | Ser—Leu—Ala—Asp—Thr—Asn—Ser—Leu—Ala—Val |
| SEQ. ID. NO. 68 | Ser—Leu—Ala—Val—Val—Ser—Thr—Gln—Leu—Ile |
| SEQ. ID. NO. 69 | Gln—Leu—Ile—Met—Pro—Val—Pro—Gly—Ile—Leu |
| SEQ. ID. NO. 70 | Ile—Leu—Leu—Val—Leu—Met—Ala—Val—Val—Leu |
| SEQ. ID. NO. 71 | Ile—Leu—Leu—Thr—Gly—Gln—Glu—Ala—Gly—Leu |
| SEQ. ID. NO. 72 | Pro—Leu—Ile—Val—Gly—Ile—Leu—Leu—Val—Leu |
| SEQ. ID. NO. 73 | Leu—Leu—Val—Leu—Met—Ala—Val—Val—Leu—Ala |
| SEQ. ID. NO. 74 | Val—Leu—Met—Ala—Val—Val—Leu—Ala—Ser—Leu |
| SEQ. ID. NO. 75 | Leu—Met—Ala—Val—Val—Leu—Ala—Ser—Leu—Ile |
| SEQ. ID. NO. 76 | Gln—Leu—Pro—His—Ser—Ser—His—Trp—Leu |
| SEQ. ID. NO. 77 | Val—Leu—Pro—Asp—Gly—Gln—Val—Ile—Trp—Val |

9 mers with Thr in position 9

| | |
|---|---|
| SEQ. ID. NO. 78 | Leu—Ile—Ser—Arg—Ala—Pro—Val—Val—Thr |
| SEQ. ID. NO. 79 | Val—Leu—Gln—Ala—Ala—Ile—Pro—Leu—Thr |
| SEQ. ID. NO. 80 | Ser—Ile—Val—Val—Leu—Ser—Gly—Thr—Thr |
| SEQ. ID. NO. 81 | Ser—Ile—Met—Ser—Thr—Glu—Ser—Ile—Thr |
| SEQ. ID. NO. 82 | Ser—Leu—Gly—Pro—Leu—Leu—Asp—Gly—Thr |

11 mers

| | |
|---|---|
| SEQ. ID. NO. 83 | Leu—Leu—His—Leu—Ala—Val—Ile—Gly—Ala—Leu—Leu |
| SEQ. ID. NO. 84 | Cys—Leu—Leu—His—Leu—Ala—Val—Ile—Gly—Ala—Leu |
| SEQ. ID. NO. 85 | His—Leu—Ala—Val—Ile—Gly—Ala—Leu—Leu—Ala—Val |
| SEQ. ID. NO. 86 | Asp—Leu—Val—Leu—Lys—Arg—Cys—Leu—Leu—His—Leu |
| SEQ. ID. NO. 87 | Val—Leu—Lys—Arg—Cys—Leu—Leu—His—Leu—Ala—Val |

Additional sequences

| | |
|---|---|
| SEQ. ID. NO. 88 | Ser—Met—Ala—Pro—Gly—Asn—Thr—Ser—Val |
| SEQ. ID. NO. 89 | Ala—Xaa—Tyr—Asp—Ala—Thr—Tyr—Glu—Thr, wherein Xaa = Leu or Ile. |

Figure 13:
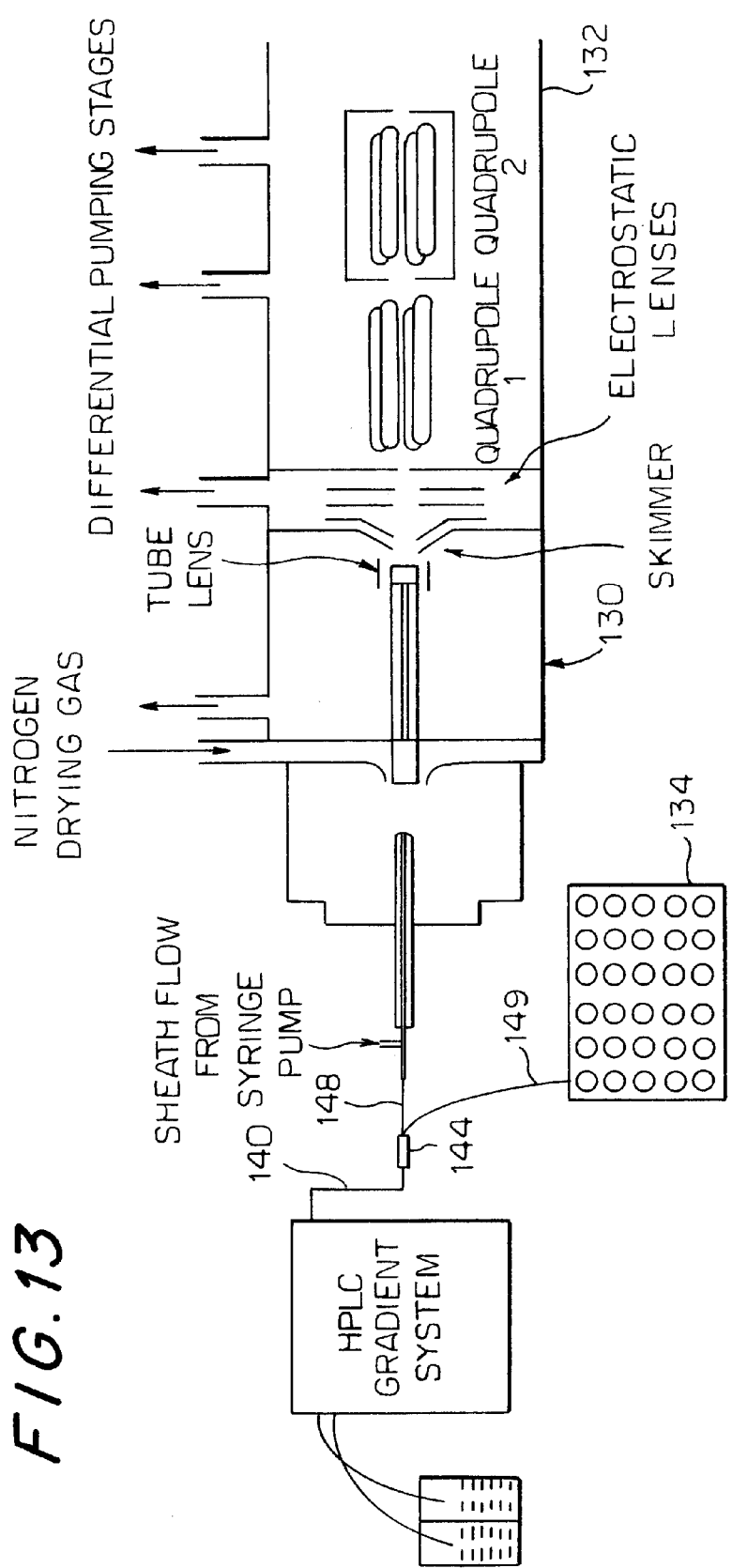
FIG. 13 is a side view of the splitter.
Figure 14:
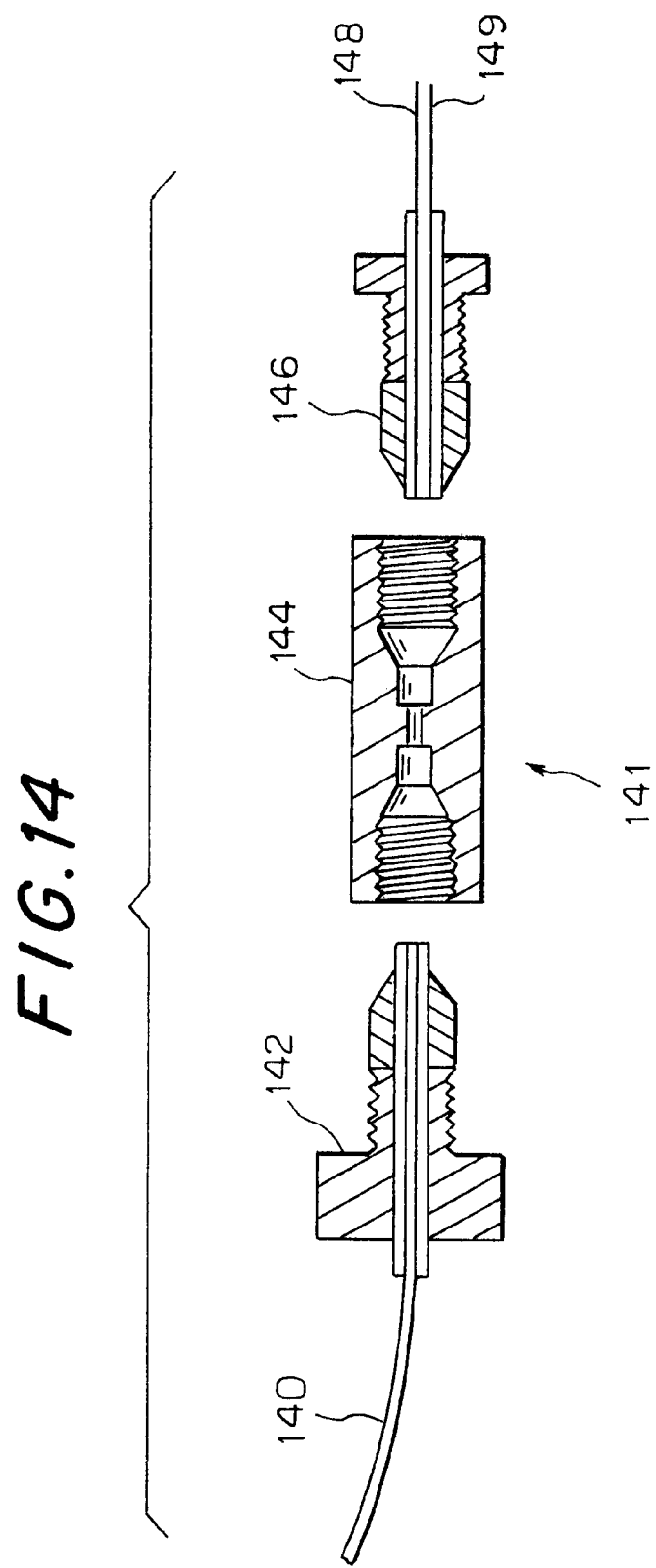
FIG. 14 is a side view of peptide sequencing by microcapillary liquid chromatography/electrospray ionization tandem mass spectromety.

In order to identify active peptides in the complex mixture obtained from the melanoma cells described above, it was necessary to find a way to split a column of liquid flowing at a rate of 840 nl/min into two equal parts without introducing turbulence (dead volume) that would destroy the chromatographic separatino achieved in the microcapillary column. Commercially available low-dead volume connections were evaluated and found to be totally unsatisfactory in the above regard. Fortunately, the system shown in FIG. 13 worked beautifully. Chromatographic resolution was found to be the same with or without the splitter in the system. The splitter is rapid to assemble and are extremely dependable. The splitter consists of a 250 microm bore SS union. Inserted into one side is a PEEK ferrule and nut containing a 350 microm o.d.×100 microm i.d. fused silica column packed with POROS beads and stuffed into Teflon tubing (1/16 inch×3 mm). Inserted into the other side is a second PEEK ferrule with SS nut containing two equal lenghts of 140 uicrom o.d.×25 microm i.d. silylated fused silica tubing also stuffed into Teflon tubing (1/16 inch×0.3 mm). Compression of the teflon tubing creat4es the zero dead volume union. The system is illustrated in FIGS. 13 and 14.

Electrospray ionization tandem mass spectrometry system 130 with online microcapillary column effluent splitter 141 to direct the effluent simultaneously to the mass spectrometer 132 and to the wells of a microtiter plate 134. A microcapillary HPLC column 140 (typically 100 $\mu$m by 22 cm) was butt connected using a zero dead volume union 144 (Valco) to two small capillaries 148 and 149 of different lengths and interior diamters (typically 25 $\mu$m and 40 $\mu$m ID, Polymicro Technologies). Typically the column was eluted with an appoximate flow rate of 500 nl/min into the union with a 34 minute gradient of 0 to 60% acetonitrile. The larger of the two capillaries directed 5/6 of the material into the electrospray ionization source (Analytica) and mass spectra were recorded on the material using a Finnigan-MAT TSQ-700 (San Jose, Calif.) triple quadrupole mass spectrometer. The 20 $\mu$m capillary deposited the remaining 1/6 of the material into 50 $\mu$l of media in microtiter plate wells. This allows deposition of a few nanoliters of eluent into a well without loss of chromatographic resolution. Timing of the splitter is adjusted so that m/z values of the peptides are recorded at the instant in which they are deposited into the well, providing a record of the peptides present in each well. The chromium release assay described in FIG. 1 was used to determine which well contained the peptide portion of the epitope.

The above peptides were tested for activity in 51Cr release assay using the procedures set forth supra, and there was preliminary evidence that several had biologic activity as CTL epitopes. However, when confirmatory experiments were performed, the only peptides with substantial VMM6 (HLA-A2.1-restricted melanoma-specific) CTL stimulatory activity were peptides 946I (SEQ ID NO: 39) and 946L (SEQ ID NO: 14). This demonstrates the significance and serendipity of the discovery of the activity of the latter two peptides.

Remarks

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

For immunological techniques generally, see Coligan, et al, *Current Protocols in Immunology* (NIH: 994); Harlow and Lane, *Antibodies:A laboratory Manual* (Cold Spring Harbor Lab.: 1988).

SEQUENCE LISTING (1) GENERAL INFORMATION:

(iii) NUMBER OF SEQUENCES: 97

(2) INFORMATION FOR SEQ ID NO: 1:

(i) SEQUENCE CHARACTERISTICS:
      (A) LENGTH: 9
      (B) TYPE: amino acids
      (C) STRANDEDNESS: Not Relevant
      (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable

```
        (vii) IMMEDIATE SOURCE: not applicable (viii) POSITION IN GENOME:
                (A) CHROMOSOME/SEGMENT: 12
                (B) MAP POSITION: unknown
                (C) UNITS: unknown (ix) FEATURE:
                (A) NAME/KEY: SEQ ID NO: 1
                (B) LOCATION: Precursor protein Pmel-17 (PIR database,
                    accession number A41234), residues 2-10.
                (C) IDENTIFICATION METHOD: This peptide was identified, from
                    the Pmel-17 molecule, as fitting the consensus sequence
                    for peptides binding to human HLA-A2.1. Pmel-17 was
                    identified because of its homology to the Seq ID No. 14
                    which has biologic activity.
                (D) OTHER INFORMATION:

(x) PUBLICATION INFORMATION: Unpublished.

(xi) SEQUENCE DESCRIPTION: SEQ ID NO: 1:

Asp Leu Val Leu Lys Arg Cys Leu Leu
                  5

(2) INFORMATION FOR SEQ ID NO: 2:

(i) SEQUENCE CHARACTERISTICS:
                (A) LENGTH: 9
                (B) TYPE: amino acids
                (C) STRANDEDNESS: Not Relevant
                (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
                (A) CHROMOSOME/SEGMENT: 12
                (B) MAP POSITION: unknown
                (C) UNITS: unknown (ix) FEATURE:
                (A) NAME/KEY: SEQ ID NO: 2
                (B) LOCATION: Precursor protein Pmel-17 (PIR database,
                    accession number A41234), residues 9-17.
                (C) IDENTIFICATION METHOD: This peptide was identified, from
                    the Pmel-17 molecule, as fitting the consensus sequence
                    for peptides binding to human HLA-A2.1. Pmel-17 was
                    identified because of its homology to the Seq ID No. 14
                    which has biologic activity.
                (D) OTHER INFORMATION:

(x) PUBLICATION INFORMATION: Unpublished.

(xi) SEQUENCE DESCRIPTION: SEQ ID NO: 2:

Leu Leu His Leu Ala Val Ile Gly Ala
1                 5

(2) INFORMATION FOR SEQ ID NO: 3:

(i) SEQUENCE CHARACTERISTICS:
                (A) LENGTH: 9
                (B) TYPE: amino acids
                (C) STRANDEDNESS: Not Relevant
                (D) TOPOLOGY: linear
```

```
        (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
              (A) CHROMOSOME/SEGMENT: 12
              (B) MAP POSITION:  unknown
              (C) UNITS:  unknown (ix) FEATURE:
              (A) NAME/KEY: SEQ ID NO: 3
              (B) LOCATION: Precursor protein Pmel-17 (PIR database,
                  accession number A41234), residues 11-19.
              (C) IDENTIFICATION METHOD:  This peptide was identified, from
                  the Pmel-17 molecule, as fitting the consensus sequence
                  for peptides binding to human HLA-A2.1. Pmel-17 was
                  identified because of its homology to the Seq ID No. 14
                  which has biologic activity.
              (D) OTHER INFORMATION:  There is evidence for biologic
                  activity as an epitope for melanoma-specific cytotoxic
                  T lymphocytes.

(x) PUBLICATION INFORMATION:  Unpublished.

(xi) SEQUENCE DESCRIPTION: SEQ ID NO: 3:

His Leu Ala Val Ile Gly Ala Leu Leu
1               5

(2) INFORMATION FOR SEQ ID NO: 4:

(i) SEQUENCE CHARACTERISTICS:
              (A) LENGTH: 9
              (B) TYPE: amino acids
              (C) STRANDEDNESS: Not Relevant
              (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
              (A) CHROMOSOME/SEGMENT: 12
              (B) MAP POSITION:  unknown
              (C) UNITS:  unknown (ix) FEATURE:
              (A) NAME/KEY: SEQ ID NO: 4
              (B) LOCATION: Precursor protein Pmel-17 (PIR database,
                  accession number A41234), residues 18-26.
              (C) IDENTIFICATION METHOD:  This peptide was identified, from
                  the Pmel-17 molecule, as fitting the consensus sequence
                  for peptides binding to human HLA-A2.1. Pmel-17 was
                  identified because of its homology to the Seq ID No. 14
                  which has biologic activity.
              (D) OTHER INFORMATION:

(x) PUBLICATION INFORMATION:  Unpublished.

(xi) SEQUENCE DESCRIPTION: SEQ ID NO:4:

Leu Leu Ala Val Gly Ala Thr Lys Val
```

1          5

(2) INFORMATION FOR SEQ ID NO: 5:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO: 5
        (B) LOCATION: Precursor protein Pmel-17 (PIR database,
            accession number A41234), residues 47-55.
        (C) IDENTIFICATION METHOD: This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:

(x) PUBLICATION INFORMATION: Unpublished.

(xi) SEQUENCE DESCRIPTION: SEQ ID NO: 5:

Gln Leu Tyr Pro Glu Trp Thr Glu Ala
1                5

(2) INFORMATION FOR SEQ ID NO: 6:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO: 6
        (B) LOCATION: Precursor protein Pmel-17 (PIR database,
            accession number A41234), residues 102-110.
        (C) IDENTIFICATION METHOD: This peptide was identified, from
            the Pmel-17 molecule, as fitting the consensus sequence
            for peptides binding to human HLA-A2.1. Pmel-17 was

```
                    identified because of its homology to the Seq ID No. 14
                    which has biologic activity.
              (D) OTHER INFORMATION:

(x) PUBLICATION INFORMATION:  Unpublished.

(xi) SEQUENCE DESCRIPTION: SEQ ID NO:6:

Val Ile Trp Val Asn Asn Thr Ile Ile
1               5

(2) INFORMATION FOR SEQ ID NO: 7:

(i) SEQUENCE CHARACTERISTICS:
              (A) LENGTH: 9
              (B) TYPE: amino acids
              (C) STRANDEDNESS: Not Relevant
              (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
              (A) CHROMOSOME/SEGMENT: 12
              (B) MAP POSITION:  unknown
              (C) UNITS:  unknown (ix) FEATURE:
              (A) NAME/KEY: SEQ ID NO: 7
              (B) LOCATION: Precursor protein Pmel-17 (PIR database,
                    accession number A41234), residues 162-170.
              (C) IDENTIFICATION METHOD:  This peptide was identified, from
                    the Pmel-17 molecule, as fitting the consensus sequence
                    for peptides binding to human HLA-A2.1. Pmel-17 was
                    identified because of its homology to the Seq ID No. 14
                    which has biologic activity.
              (D) OTHER INFORMATION:  There is evidence for biologic
                    activity as an epitope for melanoma-specific cytotoxic T
                    lymphocytes.

(x) PUBLICATION INFORMATION:  Unpublished.

(xi) SEQUENCE DESCRIPTION: SEQ ID NO: 7:

Val Leu Gly Gly Pro Val Ser Gly Leu
1               5

(2) INFORMATION FOR SEQ ID NO: 8:

(i) SEQUENCE CHARACTERISTICS:
              (A) LENGTH: 9
              (B) TYPE: amino acids
              (C) STRANDEDNESS: Not Relevant
              (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
```

```
              (A) CHROMOSOME/SEGMENT: 12
              (B) MAP POSITION: unknown
              (C) UNITS: unknown (ix) FEATURE:
              (A) NAME/KEY: SEQ ID NO: 8
              (B) LOCATION: Precursor protein Pmel-17 (PIR database,
                  accession number A41234), residues 169-177.
              (C) IDENTIFICATION METHOD: This peptide was identified, from
                  the Pmel-17 molecule, as fitting the consensus sequence
                  for peptides binding to human HLA-A2.1. Pmel-17 was
                  identified because of its homology to the Seq ID No. 14
                  which has biologic activity.
              (D) OTHER INFORMATION:

(x) PUBLICATION INFORMATION: Unpublished.

(xi) SEQUENCE DESCRIPTION: SEQ ID NO: 8:

Gly Leu Ser Ile Gly Thr Gly Arg Ala
 1               5

(2) INFORMATION FOR SEQ ID NO: 9:

(i) SEQUENCE CHARACTERISTICS:
              (A) LENGTH: 9
              (B) TYPE: amino acids
              (C) STRANDEDNESS: Not Relevant
              (D) TOPOLOGY: linear (ii) MOLECULE TYPE: peptide (iii) HYPOTHETICAL: no (iv) ANTI-SENSE: no (v) FRAGMENT TYPE: not applicable (vi) ORIGINAL SOURCE:
              (A) ORGANISM: human
              (B) STRAIN:
              (C) INDIVIDUAL ISOLATE:
              (D) DEVELOPMENTAL STAGE: adult
              (E) HAPLOTYPE:
              (F) TISSUE TYPE: melanoma
              (G) CELL TYPE:
              (H) CELL LINE: DM93 cultured melanoma line
              (I) ORGANELLE:

(vii) IMMEDIATE SOURCE: not applicable (viii) POSITION IN GENOME: unknown
              (A) CHROMOSOME/SEGMENT: unknown
              (B) MAP POSITION: unknown
              (C) UNITS: unknown (ix) FEATURE:
              (A) NAME/KEY: SEQ ID NO: 9 (YMDGTMSQV)
              (B) LOCATION: Homology is to amino acids 369-377 of the
                  tyrosinase protein (Entry A38444 in the PIR databank;
                  reference: Giebel LB, et al. Genomics (1991) 9:435-445.),
                  but there is one amino acid difference (D (aspartic
                  acid) at position 3, instead of N (asparagine)); so its
                  genetic source is not certain.
              (C) IDENTIFICATION METHOD: Direct identification and
                  sequence analysis by tandem mass spectrometry evaluation
                  of peptides eluted from HLA-A2.1 molecules of a human
                  melanoma cell line. It is present, and prevalent, among
                  the peptides eluted from HLA-A2.1 molecules of the
                  melanoma cell line, DM93.
              (D) OTHER INFORMATION: This sequence has homology with a
                  portion of the melanocyte/melanoma-specific protein,
                  tyrosinase (YMNGTMSQV is amino acids 369-377) and this
                  Seq No 9 has been identified for a Because it differs by
                  one amino acid from a self-peptide and because it is not
                  derived totally from any known protein, it may be a
                  useful target for cytotoxic T-cells.
```

(x) PUBLICATION INFORMATION: Unpublished.

(xi) SEQUENCE DESCRIPTION: SEQ ID NO: 9:

Tyr Met Asp Gly Thr Met Ser Gln Val
1               5

(2) INFORMATION FOR SEQ ID NO: 10:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown (ix) FEATURE:
            (A) NAME/KEY: SEQ ID NO: 10
            (B) LOCATION: Precursor protein Pmel-17 (PIR database,
                accession number A41234), residues 171-179.
            (C) IDENTIFICATION METHOD: This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 10:

Ser Ile Gly Thr Gly Arg Ala Met Leu
1               5

(2) INFORMATION FOR SEQ ID NO: 11:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown (ix) FEATURE:
            (A) NAME/KEY: SEQ ID NO: 11

(B) LOCATION: Precursor protein Pmel-17 (PIR database,
            accession number A41234), residues 178-186.
        (C) IDENTIFICATION METHOD:  This peptide was identified, from
            the Pmel-17 molecule, as fitting the consensus sequence
            for peptides binding to human HLA-A2.1. Pmel-17 was
            identified because of its homology to the sequence ID No.
            14 which has biologic activity.
        (D) OTHER INFORMATION:

(x) PUBLICATION INFORMATION: Unpublished.

(xi) SEQUENCE DESCRIPTION: SEQ ID NO: 11:

Met Leu Gly Thr His Thr Met Glu Val
1               5

(2) INFORMATION FOR SEQ ID NO: 12:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
         (A) CHROMOSOME/SEGMENT: 12
         (B) MAP POSITION:  unknown
         (C) UNITS:  unknown (ix) FEATURE:
         (A) NAME/KEY: SEQ ID NO: 12
         (B) LOCATION: Precursor protein Pmel-17 (PIR database,
             accession number A41234), residues 243-251.
         (C) IDENTIFICATION METHOD:  This peptide was identified, from
             the Pmel-17 molecule, as fitting the consensus sequence
             for peptides binding to human HLA-A2.1. Pmel-17 was
             identified because of its homology to the Seq ID No. 14
             which has biologic activity.
         (D) OTHER INFORMATION:

(x) PUBLICATION INFORMATION: Unpublished.

(xi) SEQUENCE DESCRIPTION: SEQ ID NO: 12:

Gln Leu His Asp Pro Ser Gly Tyr Leu
1               5

(2) INFORMATION FOR SEQ ID NO: 13:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable

```
           (vii) IMMEDIATE SOURCE:  not applicable (viii) POSITION IN GENOME:
                (A) CHROMOSOME/SEGMENT: 12
                (B) MAP POSITION:  unknown
                (C) UNITS:  unknown (ix) FEATURE:
                (A) NAME/KEY: SEQ ID NO: 13
                (B) LOCATION: Precursor protein Pmel-17 (PIR database,
                    accessio number A41234), residues 268-276.
                (C) IDENTIFICATION METHOD:  This peptide was identified, from
                    the Pmel-17 molecule, as fitting the consensus sequence
                    for peptides binding to human HLA-A2.1. Pmel-17 was
                    identified because of its homology to the Seq ID No. 14
                    which has biologic activity.
                (D) OTHER INFORMATION:

(x) PUBLICATION INFORMATION:  Unpublished.

(xi) SEQUENCE DESCRIPTION: SEQ ID NO: 13:

Thr Leu Ile Ser Arg Ala Pro Val Val
1               5

(2) INFORMATION FOR SEQ ID NO: 14:

(i) SEQUENCE CHARACTERISTICS:
                (A) LENGTH: 9
                (B) TYPE: amino acids
                (C) STRANDEDNESS: Not Relevant
                (D) TOPOLOGY: linear (ii) MOLECULE TYPE: peptide (iii) HYPOTHETICAL: no (iv) ANTI-SENSE: no (v) FRAGMENT TYPE: not applicable (vi) ORIGINAL SOURCE:
                (A) ORGANISM: human
                (B) STRAIN:
                (C) INDIVIDUAL ISOLATE:
                (D) DEVELOPMENTAL STAGE: adult
                (E) HAPLOTYPE:
                (F) TISSUE TYPE: melanoma
                (G) CELL TYPE:
                (H) CELL LINE: DM6, gift from Duke University
                (I) ORGANELLE:

(vii) IMMEDIATE SOURCE: not applicable (viii) POSITION IN GENOME:
                (A) CHROMOSOME/SEGMENT:  12
                (B) MAP POSITION:  unknown
                (C) UNITS:  unknown (ix) FEATURE:
                (A) NAME/KEY: SEQ ID NO: 14
                (B) LOCATION:  not applicable
                (C) IDENTIFICATION METHOD: Peptide was identified directly by
                    tandem mass spectrometric analysis of peptides eluted
                    from HLA-A2.1 molecules purified from the human melanoma
                    cell line,DM6,and by cytotoxicity assays using a human
                    cytotoxic T-lymphocyte line specific for HLA-A2.1+.
                    melanoma.
                (D) OTHER INFORMATION: This peptide was sythesized and was
                    found to reconstitute an epitope for multiple melanoma-
                    specific CTL lines. A database search identified 100%
                    homology with a portion of the Pmel 17 protein.

(x) PUBLICATION INFORMATION:  Unpublished.

(xi) SEQUENCE DESCRIPTION: SEQ ID NO: 14:

Tyr Leu Glu Pro Gly Pro Val Thr Ala
```

```
                         -continued
1           5

(2) INFORMATION FOR SEQ ID NO: 15:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 15
        (B) LOCATION: Precursor protein Pmel-17 (PIR database,
            accession number A41234), residues 373-381.
        (C) IDENTIFICATION METHOD:  This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:

(x) PUBLICATION INFORMATION:  Unpublished.

(xi) SEQUENCE DESCRIPTION: SEQ ID NO: 15:

Gly Met Thr Pro Glu Lys Val Pro Val
1               5

(2) INFORMATION FOR SEQ ID NO: 16:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 16
        (B) LOCATION: Precursor protein Pmel-17 (PIR database,
            accession number A41234), residues 399-407.
        (C) IDENTIFICATION METHOD:  This peptide was identified, from
            the Pmel-17 molecule, as fitting the consensus sequence
            for peptides binding to human HLA-A2.1. Pmel-17 was
``` identified because of its homology to the Seq ID No. 14 which has biologic activity.
            (D) OTHER INFORMATION:

(x) PUBLICATION INFORMATION: Unpublished.

(xi) SEQUENCE DESCRIPTION: SEQ ID NO: 16:

Gly Met Thr Pro Ala Glu Val Ser Ile
1               5

(2) INFORMATION FOR SEQ ID NO: 17:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 17
        (B) LOCATION: Precursor protein Pmel-17 (PIR database,
            accession number A41234), residues 449-457.
        (C) IDENTIFICATION METHOD:  This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:  There is evidence for biologic
            activity as an epitope for melanoma-specific cytotoxic T
            lymphocytes (x) PUBLICATION INFORMATION:  Unpublished.

(xi) SEQUENCE DESCRIPTION: SEQ ID NO: 17:

Ser Ile Thr Gly Ser Leu Gly Pro Leu
1               5

(2) INFORMATION FOR SEQ ID NO: 18:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:

```
        (A) CHROMOSOME/SEGMENT: 12
        (B) MAP POSITION:  unknown
        (C) UNITS:  unknown (ix) FEATURE:
        (A) NAME/KEY: SEQ ID NO: 18
        (B) LOCATION: Precursor protein Pmel-17 (PIR database,
            accession number A41234), residues 456-464.
        (C) IDENTIFICATION METHOD:  This peptide was identified,
            from the Pmel-17 molecule, as fitting the consensus
            sequence for peptides binding to human HLA-A2.1. Pmel-17
            was identified because of its homology to the Seq ID No.
            14 which has biologic activity.
        (D) OTHER INFORMATION:

(x) PUBLICATION INFORMATION:  Unpublished.

(xi) SEQUENCE DESCRIPTION: SEQ ID NO: 18:

Pro Leu Leu Asp Gly Thr Ala Thr Leu
1               5

(2) INFORMATION FOR SEQ ID NO: 19:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 19
        (B) LOCATION: Precursor protein Pmel-17 (PIR database,
            accession number A41234), residues 463-471.
        (C) IDENTIFICATION METHOD:  This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:

(x) PUBLICATION INFORMATION:  Unpublished.

(xi) SEQUENCE DESCRIPTION: SEQ ID NO: 19:

Thr Leu Arg Leu Val Lys Arg Gln Val
1               5

(2) INFORMATION FOR SEQ ID NO: 20:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no
```

(iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 20
            (B) LOCATION: Precursor protein Pmel-17 (PIR database,
                accession number A41234), residues 465-473.
            (C) IDENTIFICATION METHOD:  This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION:  Unpublished.

(xi) SEQUENCE DESCRIPTION: SEQ ID NO: 20:

Arg Leu Val Lys Arg Gln Val Pro Leu
1               5

(2) INFORMATION FOR SEQ ID NO: 21:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 21
            (B) LOCATION: Precursor protein Pmel-17 (PIR database,
                accession number A41234), residues 488-496.
            (C) IDENTIFICATION METHOD:  This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION: None (x) PUBLICATION INFORMATION:  Unpublished.

(xi) SEQUENCE DESCRIPTION: SEQ ID NO: 21:

Asp Ile Val Gln Gly Ile Glu Ser Ala
1               5

(2) INFORMATION FOR SEQ ID NO: 22:

(i) SEQUENCE CHARACTERISTICS:

```
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 22
            (B) LOCATION: Precursor protein Pmel-17 (PIR database,
                accession number A41234), residues 544-552.
            (C) IDENTIFICATION METHOD:  This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION: None (x) PUBLICATION INFORMATION:  Unpublished.

(xi) SEQUENCE DESCRIPTION: SEQ ID NO: 22:

Val Leu Pro Ser Pro Ala Cys Gln Leu
1               5

(2) INFORMATION FOR SEQ ID NO: 23:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 23
            (B) LOCATION: Precursor protein Pmel-17 (PIR database,
                accession number A41234), residues 570-578.
            (C) IDENTIFICATION METHOD:  This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION: None (x) PUBLICATION INFORMATION:  Unpublished.
```

```
        (xi) SEQUENCE DESCRIPTION: SEQ ID NO: 23:

Ser Leu Ala Asp Thr Asn Ser Leu Ala
1               5

(2) INFORMATION FOR SEQ ID NO: 24:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
         (A) CHROMOSOME/SEGMENT: 12
         (B) MAP POSITION:  unknown
         (C) UNITS:  unknown (ix) FEATURE:
         (A) NAME/KEY: SEQ ID NO: 24
         (B) LOCATION: Precursor protein Pmel-17 (PIR database,
             accession number A41234), residues 576-584.
         (C) IDENTIFICATION METHOD:  This peptide was identified, from
             the Pmel-17 molecule, as fitting the consensus sequence
             for peptides binding to human HLA-A2.1. Pmel-17 was
             identified because of its homology to the Seq ID No. 14
             which has biologic activity.
         (D) OTHER INFORMATION: None (x) PUBLICATION INFORMATION:  Unpublished.

(xi) SEQUENCE DESCRIPTION: SEQ ID NO: 24:

Ser Leu Ala Val Val Ser Thr Gln Leu
1               5

(2) INFORMATION FOR SEQ ID NO: 25:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
         (A) CHROMOSOME/SEGMENT: 12
         (B) MAP POSITION:  unknown
         (C) UNITS:  unknown (ix) FEATURE:
         (A) NAME/KEY: SEQ ID NO: 25
         (B) LOCATION: Precursor protein Pmel-17 (PIR database,
             accession number A41234), residues 583-591.
```

(C) IDENTIFICATION METHOD: This peptide was identified, from
    the Pmel-17 molecule, as fitting the consensus sequence
    for peptides binding to human HLA-A2.1. Pmel-17 was
    identified because of its homology to the Seq ID No. 14
    which has biologic activity.
(D) OTHER INFORMATION: There is evidence for biologic
    activity as an epitope for melanoma-specific cytotoxic T
    lymphocytes.

(x) PUBLICATION INFORMATION: Unpublished.

(xi) SEQUENCE DESCRIPTION: SEQ ID NO: 25:

Gln Leu Ile Met Pro Val Pro Gly Ile
1               5

(2) INFORMATION FOR SEQ ID NO: 26:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO: 26
        (B) LOCATION: Precursor protein Pmel-17 (PIR database,
            accession number A41234), residues 584-592.
        (C) IDENTIFICATION METHOD: This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION: None (x) PUBLICATION INFORMATION: Unpublished.

(xi) SEQUENCE DESCRIPTION: SEQ ID NO: 26:

Leu Ile Met Pro Val Pro Gly Ile Leu
1               5

(2) INFORMATION FOR SEQ ID NO: 27:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 27
             (B) LOCATION: Precursor protein Pmel-17 (PIR database,
                 accession number A41234), residues 585-593.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION: None (x) PUBLICATION INFORMATION: Unpublished.

(xi) SEQUENCE DESCRIPTION: SEQ ID NO: 27:

Ile Met Pro Val Pro Gly Ile Leu Leu
1               5

(2) INFORMATION FOR SEQ ID NO: 28:

(i) SEQUENCE CHARACTERISTICS:
             (A) LENGTH: 9
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 28
             (B) LOCATION: Precursor protein Pmel-17 (PIR database,
                 accession number A41234), residues 590-598.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION: None (x) PUBLICATION INFORMATION: Unpublished.

(xi) SEQUENCE DESCRIPTION: SEQ ID NO: 28:

Gly Ile Leu Leu Thr Gly Gln Glu Ala
1               5

(2) INFORMATION FOR SEQ ID NO: 29:

(i) SEQUENCE CHARACTERISTICS:
             (A) LENGTH: 9
             (B) TYPE: amino acids
             (C) STRANDEDNESS: Not Relevant
             (D) TOPOLOGY: linear (ii) MOLECULE TYPE: peptide

```
    (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 29
           (B) LOCATION: Precursor protein Pmel-17 (PIR database,
               accession number A41234), residues 592-600.
           (C) IDENTIFICATION METHOD:  This peptide was identified, from
               the Pmel-17 molecule, as fitting the consensus sequence
               for peptides binding to human HLA-A2.1.  Pmel-17 was
               identified because of its homology to the Seq ID No. 14
               which has biologic activity.
           (D) OTHER INFORMATION:  None (x) PUBLICATION INFORMATION:  Unpublished.

(xi) SEQUENCE DESCRIPTION: SEQ ID NO: 29:

Leu Leu Thr Gly Gln Glu Ala Gly Leu
1               5

(2) INFORMATION FOR SEQ ID NO: 30:

(i) SEQUENCE CHARACTERISTICS:
           (A) LENGTH: 9
           (B) TYPE: amino acids
           (C) STRANDEDNESS: Not Relevant
           (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 30
           (B) LOCATION: Precursor protein Pmel-17 (PIR database,
               accession number A41234), residues 599-607.
           (C) IDENTIFICATION METHOD: This peptide was identified, from
               the Pmel-17 molecule,  as fitting the consensus sequence
               for peptides binding to human HLA-A2.1.  Pmel-17 was
               identified because of its homology to the Seq ID No. 14
               which has biologic activity.
           (D) OTHER INFORMATION:  None (x) PUBLICATION INFORMATION:  Unpublished.

(xi) SEQUENCE DESCRIPTION: SEQ ID NO: 30:

Gly Leu Gly Gln Val Pro Leu Ile Val
1               5
```

```
(2) INFORMATION FOR SEQ ID NO: 31:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 31
        (B) LOCATION: Precursor protein Pmel-17 (PIR database,
            accession number A41234), residues 604-612.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION: None (x) PUBLICATION INFORMATION:  Unpublished.

(xi) SEQUENCE DESCRIPTION: SEQ ID NO: 31:

Pro Leu Ile Val Gly Ile Leu Leu Val
1               5

(2) INFORMATION FOR SEQ ID NO: 32:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 32
        (B) LOCATION: Precursor protein Pmel-17 (PIR database,
            accession number A41234), residues 605-613.
        (C) IDENTIFICATION METHOD: This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION: None
```

```
            (x) PUBLICATION INFORMATION:  Unpublished.

(xi) SEQUENCE DESCRIPTION: SEQ ID NO: 32:

Leu Ile Val Gly Ile Leu Leu Val Leu
1               5

(2) INFORMATION FOR SEQ ID NO: 33:

(i) SEQUENCE CHARACTERISTICS:
             (A) LENGTH: 9
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
             (A) CHROMOSOME/SEGMENT: 12
             (B) MAP POSITION:  unknown
             (C) UNITS:  unknown (ix) FEATURE:
             (A) NAME/KEY: SEQ ID NO: 33
             (B) LOCATION: Precursor protein Pmel-17 (PIR database,
                 accession number A41234), residues 608-616.
             (C) IDENTIFICATION METHOD:  This peptide was identified, from
                 the Pmel-17 molecule, as fitting the consensus sequence
                 for peptides binding to human HLA-A2.1.  Pmel-17 was
                 identified because of its homology to the Seq ID No. 14
                 which has biologic activity.
             (D) OTHER INFORMATION:  There is evidence for biologic
                 activity as an epitope for melanoma-specific cytotoxic T
                 lymphocytes.

(x) PUBLICATION INFORMATION:  Unpublished.

(xi) SEQUENCE DESCRIPTION: SEQ ID NO: 33:

Gly Ile Leu Leu Val Leu Met Ala Val
1               5

(2) INFORMATION FOR SEQ ID NO: 34:

(i) SEQUENCE CHARACTERISTICS:
             (A) LENGTH: 9
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
             (A) CHROMOSOME/SEGMENT: 12
             (B) MAP POSITION:  unknown
             (C) UNITS:  unknown
```

(ix) FEATURE:
        (A) NAME/KEY: SEQ ID NO: 34
        (B) LOCATION: Precursor protein Pmel-17 (PIR database,
            accession number A41234), residues 609-617.
        (C) IDENTIFICATION METHOD: This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION: There is evidence for biologic
            activity as an epitope for melanoma-specific cytotoxic T
            lymphocytes.

(x) PUBLICATION INFORMATION: Unpublished.

(xi) SEQUENCE DESCRIPTION: SEQ ID NO: 34:

Ile Leu Leu Val Leu Met Ala Val Val
1               5

(2) INFORMATION FOR SEQ ID NO: 35:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO: 35
        (B) LOCATION: Precursor protein Pmel-17 (PIR database,
            accession number A41234), residues 610-618.
        (C) IDENTIFICATION METHOD: This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION: None (x) PUBLICATION INFORMATION: Unpublished.

(xi) SEQUENCE DESCRIPTION: SEQ ID NO: 35:

Leu Leu Val Leu Met Ala Val Val Leu
1               5

(2) INFORMATION FOR SEQ ID NO: 36:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 36
            (B) LOCATION: Precursor protein Pmel-17 (PIR database,
                accession number A41234), residues 613-621.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:  None (x) PUBLICATION INFORMATION:  Unpublished.

(xi) SEQUENCE DESCRIPTION: SEQ ID NO: 36:

Leu Met Ala Val Val Leu Ala Ser Leu
1               5

(2) INFORMATION FOR SEQ ID NO: 37:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 37
            (B) LOCATION: Precursor protein Pmel-17 (PIR database,
                accession number A41234), residues 626-634.
            (C) IDENTIFICATION METHOD:  This peptide was identification, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION: None (x) PUBLICATION INFORMATION:  Unpublished.

(xi) SEQUENCE DESCRIPTION: SEQ ID NO: 37:

Arg Leu Met lys Gln Asp Phe Ser Val
1               5

(2) INFORMATION FOR SEQ ID NO: 38:

(i) SEQUENCE CHARACTERISTICS:
            (A) LENGTH: 9

```
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 38
            (B) LOCATION: Precursor protein Pmel-17 (PIR database,
                accession number A41234), residues 655-663.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:  None (x) PUBLICATION INFORMATION:  Unpublished.

(xi) SEQUENCE DESCRIPTION: SEQ ID NO: 38:

Pro Ile Gly Glu Asn Ser Pro Leu Leu
1               5

(2) INFORMATION FOR SEQ ID NO: 39:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: not applicable (vi) ORIGINAL SOURCE:
            (A) ORGANISM: human
            (B) STRAIN:
            (C) INDIVIDUAL ISOLATE:
            (D) DEVELOPMENTAL STAGE: adult
            (E) HAPLOTYPE:
            (F) TISSUE TYPE: melanoma
            (G) CELL TYPE:
            (H) CELL LINE: DM6, gift from Duke University
            (I) ORGANELLE:

(vii) IMMEDIATE SOURCE: not applicable (viii) POSITION IN GENOME:
            (A) CHROMOSOME/SEGMENT:  12
            (B) MAP POSITION:  unknown
            (C) UNITS:  unknown (ix) FEATURE:
            (A) NAME/KEY: SEQ ID NO: 39
            (B) LOCATION: not applicable
            (C) IDENTIFICATION METHOD: This peptide was identified
                directly by tandem mass spectrometric analysis of
``` peptides eluted from HLA-A2.1 molecules purified from the
                human melanoma cell line, DM6, and by cyto toxicity
                assays using a human cytotoxic T-lymphocyte line (CTL)
                specific for HLA-A2.1+ melanoma.
            (D) OTHER INFORMATION: This peptide was sythesized and was
                found to reconstitute an epitope for multiple melanoma-
                specific CTL lines. A database search identified 100%
                homology with a portion of the Pmel 17 protein.

(x) PUBLICATION INFORMATION: Unpublished.

(xi) SEQUENCE DESCRIPTION: SEQ ID NO: 39:

Tyr Ile Glu Pro Gly Pro Val Thr Ala
1               5

(2) INFORMATION FOR SEQ ID NO: 40:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT:
        (B) MAP POSITION:  unknown
        (C) UNITS:  unknown (ix) FEATURE:
        (A) NAME/KEY: SEQ ID NO: 40
        (B) LOCATION: Precursor protein Pmel-17 (PIR database,
            accession number A41234), residues 4-13.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION:  None (x) PUBLICATION INFORMATION: Unpublished.

(xi) SEQUENCE DESCRIPTION: SEQ ID NO: 40:

Val Leu Lys Arg Cys Leu Leu His Leu Ala
1               5                   10

(2) INFORMATION FOR SEQ ID NO: 41:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 41
             (B) LOCATION: Precursor protein Pmel-17 (PIR database,
                 accession number A41234), residues 8-17.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION: None (x) PUBLICATION INFORMATION: Unpublished.

(xi) SEQUENCE DESCRIPTION: SEQ ID NO: 41:

Cys Leu Leu His Leu Ala Val Ile Gly Ala
1               5                   10

(2) INFORMATION FOR SEQ ID NO: 42:

(i) SEQUENCE CHARACTERISTICS:
             (A) LENGTH: 10
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 42
             (B) LOCATION: Precursor protein Pmel-17 (PIR database,
                 accession number A41234), residues 9-18.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION: None (x) PUBLICATION INFORMATION: Unpublished.

(xi) SEQUENCE DESCRIPTION: SEQ ID NO: 42:

Leu Leu His Leu Ala Val Ile Gly Ala Leu
1               5                   10

(2) INFORMATION FOR SEQ ID NO: 43:

(i) SEQUENCE CHARACTERISTICS:
             (A) LENGTH: 10
             (B) TYPE: amino acids
             (C) STRANDEDNESS: Not Relevant
             (D) TOPOLOGY: linear (ii) MOLECULE TYPE: peptide

```
    (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
          (A) CHROMOSOME/SEGMENT: 12
          (B) MAP POSITION:  unknown
          (C) UNITS:  unknown (ix) FEATURE:
          (A) NAME/KEY: SEQ ID NO: 43
          (B) LOCATION: Precursor protein Pmel-17 (PIR database,
              accession number A41234), residues 11-20.
          (C) IDENTIFICATION METHOD:  This peptide was identified, from
              the Pmel-17 molecule, as fitting the consensus sequence
              for peptides binding to human HLA-A2.1.  Pmel-17 was
              identified because of its homology to the Seq ID No. 14
              which has biologic activity.
          (D) OTHER INFORMATION:  None (x) PUBLICATION INFORMATION:  Unpublished.

(xi) SEQUENCE DESCRIPTION: SEQ ID NO: 43:

His Leu Ala Val Ile Gly Ala Leu Leu Ala
1               5                   10

(2) INFORMATION FOR SEQ ID NO: 44:

(i) SEQUENCE CHARACTERISTICS:
          (A) LENGTH: 10
          (B) TYPE: amino acids
          (C) STRANDEDNESS: Not Relevant
          (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
          (A) CHROMOSOME/SEGMENT: 12
          (B) MAP POSITION:  unknown
          (C) UNITS:  unknown (ix) FEATURE:
          (A) NAME/KEY: SEQ ID NO: 44
          (B) LOCATION: Precursor protein Pmel-17 (PIR database,
              accession number A41234), residues 17-26.
          (C) IDENTIFICATION METHOD: This peptide was identified, from
              the Pmel-17 molecule, as fitting the consensus sequence
              for peptides binding to human HLA-A2.1. Pmel-17 was
              identified because of its homology to the Seq ID No. 14
              which has biologic activity.
          (D) OTHER INFORMATION:  None (x) PUBLICATION INFORMATION:  Unpublished.

(xi) SEQUENCE DESCRIPTION: SEQ ID NO:44:

Ala Leu Leu Ala Val Gly Ala Thr Lys Val
1               5                   10
```

```
(2) INFORMATION FOR SEQ ID NO: 45:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 45
        (B) LOCATION: Precursor protein Pmel-17 (PIR database,
            accession number A41234), residues 32-41.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION:  None (x) PUBLICATION INFORMATION:  Unpublished.

(xi) SEQUENCE DESCRIPTION: SEQ ID NO: 45:

Trp Leu Gly Val Ser Arg Gln Leu Arg Thr
1               5                   10

(2) INFORMATION FOR SEQ ID NO:46:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 46
        (B) LOCATION: Precursor protein Pmel-17 (PIR database,
            accession number A41234), residues 57-66.
        (C) IDENTIFICATION METHOD: This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION:  None
```

(x) PUBLICATION INFORMATION: Unpublished.

(xi) SEQUENCE DESCRIPTION: SEQ ID NO: 46:

Arg Leu Asp Cys Trp Arg Gly Gly Gln Val
1               5                   10

(2) INFORMATION FOR SEQ ID NO: 47:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 47
            (B) LOCATION: Precursor protein Pmel-17 (PIR database,
                accession number A41234), residues 67-76.
            (C) IDENTIFICATION METHOD:  This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 47:

Ser Leu Lys Val Ser Asn Asp Gly Pro Thr
1               5                   10

(2) INFORMATION FOR SEQ ID NO: 48:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:

(A) NAME/KEY: SEQ ID NO: 48
            (B) LOCATION: Precursor protein Pmel-17 (PIR database,
                accession number A41234), residues 87-96.
            (C) IDENTIFICATION METHOD: This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 48:

Ala Leu Asn Phe Pro Gly Ser Gln Lys Val
1               5                   10

(2) INFORMATION FOR SEQ ID NO: 49:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown (ix) FEATURE:
            (A) NAME/KEY: SEQ ID NO: 49
            (B) LOCATION: Precursor protein Pmel-17 (PIR database,
                accession number A41234), residues 177-186.
            (C) IDENTIFICATION METHOD: This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 49:

Ala Met Leu Gly Thr His Thr Met Glu Val
1               5                   10

(2) INFORMATION FOR SEQ ID NO: 50:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown (ix) FEATURE:
            (A) NAME/KEY: SEQ ID NO: 50
            (B) LOCATION: Precursor protein Pmel-17 (PIR database,
                accession number A41234), residues 178-187.
            (C) IDENTIFICATION METHOD: This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 50:

Met Leu Gly Thr His Thr Met Glu Val Thr
1               5                   10

(2) INFORMATION FOR SEQ ID NO: 51:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown (ix) FEATURE:
            (A) NAME/KEY: SEQ ID NO: 51
            (B) LOCATION: Precursor protein Pmel-17 (PIR database,
                accession number A41234), residues 199-208.
            (C) IDENTIFICATION METHOD: This peptide was identified, from
                the Pmel-17 molecule, as fitting the consensus sequence
                for peptides binding to human HLA-A2.1. Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 51:

Pro Leu Ala His Ser Ser Ser Ala Phe Thr
1               5                   10

(2) INFORMATION FOR SEQ ID NO: 52:

(i) SEQUENCE CHARACTERISTICS:
            (A) LENGTH: 10
            (B) TYPE: amino acids
            (C) STRANDEDNESS: Not Relevant
            (D) TOPOLOGY: linear

```
    (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 52
           (B) LOCATION: Precursor protein Pmel-17 (PIR database,
               accession number A41234), residues 224-233.
           (C) IDENTIFICATION METHOD:  This peptide was identified, from
               the Pmel-17 molecule, as fitting the consensus sequence
               for peptides binding to human HLA-A2.1. Pmel-17 was
               identified because of its homology to the Seq ID No. 14
               which has biologic activity.
           (D) OTHER INFORMATION:

(x) PUBLICATION INFORMATION:  Unpublished.

(xi) SEQUENCE DESCRIPTION: SEQ ID NO: 52:

Ala Leu Asp Gly Gly Asn Lys His Phe Leu
1               5                   10

(2) INFORMATION FOR SEQ ID NO: 53:

(i) SEQUENCE CHARACTERISTICS:
           (A) LENGTH: 10
           (B) TYPE: amino acids
           (C) STRANDEDNESS: Not Relevant
           (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 53
           (B) LOCATION: Precursor protein Pmel-17 (PIR database,
               accession number A41234), residues 232-241.
           (C) IDENTIFICATION METHOD:  This peptide was identified, from
               the Pmel-17 molecule, as fitting the consensus sequence
               for peptides binding to human HLA-A2.1. Pmel-17 was
               identified because of its homology to the Seq ID No. 14
               which has biologic activity.
           (D) OTHER INFORMATION:

(x) PUBLICATION INFORMATION:  Unpublished.

(xi) SEQUENCE DESCRIPTION: SEQ ID NO: 53:

Phe Leu Arg Asn Gln Pro Leu Thr Phe Ala
1               5                   10
```

```
(2) INFORMATION FOR SEQ ID NO: 54:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 54
        (B) LOCATION: Precursor protein Pmel-17 (PIR database,
            accession number A41234), residues 243-252.
        (C) IDENTIFICATION METHOD:  This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:

(x) PUBLICATION INFORMATION:  Unpublished.

(xi) SEQUENCE DESCRIPTION: SEQ ID NO:54:

Gln Leu His Asp Pro Ser Gly Tyr Leu Ala
1               5                   10

(2) INFORMATION FOR SEQ ID NO: 55:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 55
        (B) LOCATION: Precursor protein Pmel-17 (PIR database,
            accession number A41234), residues 250-259.
        (C) IDENTIFICATION METHOD:  This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
```

```
            (D) OTHER INFORMATION:

(x) PUBLICATION INFORMATION: Unpublished.

(xi) SEQUENCE DESCRIPTION: SEQ ID NO: 55:

Tyr Leu Ala Glu Ala Asp Leu Ser Tyr Thr
1               5                   10

(2) INFORMATION FOR SEQ ID NO: 56:

(i) SEQUENCE CHARACTERISTICS:
         (A) LENGTH: 10
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
         (A) CHROMOSOME/SEGMENT: 12
         (B) MAP POSITION:  unknown
         (C) UNITS:  unknown (ix) FEATURE:
         (A) NAME/KEY: SEQ ID NO: 56
         (B) LOCATION: Precursor protein Pmel-17 (PIR database,
             accession number A41234), residues 268-277.
         (C) IDENTIFICATION METHOD:  This peptide was identified, from
             the Pmel-17 molecule, as fitting the consensus sequence
             for peptides binding to human HLA-A2.1.  Pmel-17 was
             identified because of its homology to the Seq ID No. 14
             which has biologic activity.
         (D) OTHER INFORMATION:

(x) PUBLICATION INFORMATION: Unpublished.

(xi) SEQUENCE DESCRIPTION: SEQ ID NO: 56:

Thr Leu Ile Ser Arg Ala Pro Val Val Thr
1               5                   10

(2) INFORMATION FOR SEQ ID NO: 57:

(i) SEQUENCE CHARACTERISTICS:
         (A) LENGTH: 10
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
         (A) CHROMOSOME/SEGMENT: 12
         (B) MAP POSITION:  unknown
         (C) UNITS:  unknown
```

(ix) FEATURE:
            (A) NAME/KEY: SEQ ID NO: 57
            (B) LOCATION: Precursor protein Pmel-17 (PIR database,
                accession number A41234), residues 297-306.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:

(x) PUBLICATION INFORMATION:  Unpublished.

(xi) SEQUENCE DESCRIPTION: SEQ ID NO: 57:

Pro Leu Thr Ser Cys Gly Ser Ser Pro Val
1               5                   10

(2) INFORMATION FOR SEQ ID NO: 58:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (xi) SEQUENCE DESCRIPTION: SEQ ID NO: 58:

Thr Leu Ala Glu Met Ser Thr Pro Glu Ala
1               5                   10

(2) INFORMATION FOR SEQ ID NO: 59:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 59
            (B) LOCATION: Precursor protein Pmel-17 (PIR database,
                accession number A41234), residues 399-408.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:

(x) PUBLICATION INFORMATION:  Unpublished.

(xi) SEQUENCE DESCRIPTION: SEQ ID NO: 59:

Gly Met Thr Pro Ala Glu Val Ser Ile Val
1               5                   10

(2) INFORMATION FOR SEQ ID NO: 60:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 60
        (B) LOCATION: Precursor protein Pmel-17 (PIR database,
            accession number A41234), residues 409-418.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION:

(x) PUBLICATION INFORMATION:  Unpublished.

(xi) SEQUENCE DESCRIPTION: SEQ ID NO: 60:

```
Val Leu Ser Gly Thr Thr Ala Ala Gln Val
1               5                   10
```

(2) INFORMATION FOR SEQ ID NO: 61:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 61
        (B) LOCATION: Precursor protein Pmel-17 (PIRt database,
            accession number A41234), residues 453-462.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.

(D) OTHER INFORMATION:

(x) PUBLICATION INFORMATION: Unpublished.

(xi) SEQUENCE DESCRIPTION: SEQ ID NO: 61:

Ser Leu Gly Pro Leu Leu Asp Gly Thr Ala
1               5                   10

(2) INFORMATION FOR SEQ ID NO: 62:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown (ix) FEATURE:
            (A) NAME/KEY: SEQ ID NO: 62
            (B) LOCATION: Precursor protein Pmel-17 (PIR database,
                accession number A41234), residues 457-466.
            (C) IDENTIFICATION METHOD: This peptide was identified, from
                the Pmel-17 molecule, as fitting the consensus sequence
                for peptides binding to human HLA-A2.1. Pmel-17 was
                identified because of its homology
                to the Seq ID No. 14 which has biologic activity.
            (D) OTHER INFORMATION:

(x) PUBLICATION INFORMATION: Unpublished.

(xi) SEQUENCE DESCRIPTION: SEQ ID NO: 62:

Leu Leu Asp Gly Thr Ala Thr Leu Arg Leu
1               5                   10

(2) INFORMATION FOR SEQ ID NO: 63:

(i) SEQUENCE CHARACTERISTICS:
            (A) LENGTH: 10
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
            (A) CHROMOSOME/SEGMENT: 12
            (B) MAP POSITION: unknown
            (C) UNITS: unknown

```
    (ix) FEATURE:
        (A) NAME/KEY: SEQ ID NO: 63
        (B) LOCATION: Precursor protein Pmel-17 (PIR database,
            accession number A41234), residues 476-485.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION:

(x) PUBLICATION INFORMATION:  Unpublishled.

(xi) SEQUENCE DESCRIPTION: SEQ ID NO: 63:

Val Leu Tyr Arg Tyr Gly Ser Phe Ser Val
1               5                   10

(2) INFORMATION FOR SEQ ID NO: 64:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
        (A) CHROMOSOME/SEGMENT: 12
        (B) MAP POSITION:  unknown
        (C) UNITS:  unknown (ix) FEATURE:
        (A) NAME/KEY: SEQ ID NO: 64
        (B) LOCATION: Precursor protein Pmel-17 (PIR database,
            accession number A41234), residues 511-520.
        (C) IDENTIFICATION METHOD:  This peptide was identified, from
            the Pmel-17 molecule, as fitting the consensus sequence
            for peptides binding to human HLA-A2.1.  Pmel-17 was
            identified because of its homology to the Seq ID No. 14
            which has biologic activity.
        (D) OTHER INFORMATION:

(x) PUBLICATION INFORMATION:  Unpublished.

(xi) SEQUENCE DESCRIPTION: SEQ ID NO: 64:

Glu Leu Thr Val Ser Cys Gln Gly Gly Leu
1               5                   10

(2) INFORMATION FOR SEQ ID NO: 65:

(i) SEQUENCE CHARACTERISTICS:
        (A) LENGTH: 10
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment
```

(vi) ORIGINAL SOURCE: not applicable (vii) IMMEDIATE SOURCE:  not applicable (viii) POSITION IN GENOME:
             (A) CHROMOSOME/SEGMENT: 12
             (B) MAP POSITION:  unknown
             (C) UNITS:  unknown (ix) FEATURE:
             (A) NAME/KEY: SEQ ID NO: 65
             (B) LOCATION: Precursor protein Pmel-17 (PIR database,
                 accession number A41234), residues 519-528.
             (C) IDENTIFICATION METHOD:  This peptide was identified, from
                 the Pmel-17 molecule, as fitting the consensus sequence
                 for peptides binding to human HLA-A2.1.  Pmel-17 was
                 identified because of its homology to the Seq ID No. 14
                 which has biologic activity.
             (D) OTHER INFORMATION:

(x) PUBLICATION INFORMATION:  Unpublished.

(xi) SEQUENCE DESCRIPTION: SEQ ID NO: 65:

Gly Leu Pro Lys Glu Ala Cys Met Glu Ile
1               5                   10

(2) INFORMATION FOR SEQ ID NO: 66:

(i) SEQUENCE CHARACTERISTICS:
             (A) LENGTH: 10
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
             (A) CHROMOSOME/SEGMENT: 12
             (B) MAP POSITION:  unknown
             (C) UNITS:  unknown (ix) FEATURE:
             (A) NAME/KEY: SEQ ID NO: 66
             (B) LOCATION: Precursor protein Pmel-17 (PIR database,
                 accession number A41234), residues 544-553.
             (C) IDENTIFICATION METHOD:  This peptide was identified, from
                 the Pmel-17 molecule, as fitting the consensus sequence
                 for peptides binding to human HLA-A2.1.  Pmel-17 was
                 identified because of its homology to the Seq ID No. 14
                 which has biologic activity.
             (D) OTHER INFORMATION:

(x) PUBLICATION INFORMATION:  Unpublished.

(xi) SEQUENCE DESCRIPTION: SEQ ID NO: 66:

Val Leu Pro Ser Pro Ala Cys Gln Leu Val
1               5                   10

(2) INFORMATION FOR SEQ ID NO: 67:

(i) SEQUENCE CHARACTERISTICS:
             (A) LENGTH: 10
             (B) TYPE: amino acids
             (C) STRANDEDNESS: Not Relevant
             (D) TOPOLOGY: linear

```
      (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 67
           (B) LOCATION: Precursor protein Pmel-17 (PIR database,
               accession number A41234), residues 570-579.
           (C) IDENTIFICATION METHOD:  This peptide was identified, from
               the Pmel-17 molecule, as fitting the consensus sequence
               for peptides binding to human HLA-A2.1.  Pmel-17 was
               identified because of its homology to the Seq ID No. 14
               which has biologic activity.
           (D) OTHER INFORMATION:

(x) PUBLICATION INFORMATION:  Unpublished.

(xi) SEQUENCE DESCRIPTION: SEQ ID NO: 67:

Ser Leu Ala Asp Thr Asn Ser Leu Ala Val
1               5                   10

(2) INFORMATION FOR SEQ ID NO: 68:

(i) SEQUENCE CHARACTERISTICS:
           (A) LENGTH: 10
           (B) TYPE: amino acids
           (C) STRANDEDNESS: Not Relevant
           (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 68
           (B) LOCATION: Precursor protein Pmel-17 (PIR database,
               accession number A41234), residues 576-585.
           (C) IDENTIFICATION METHOD:  This peptide was identified, from
               the Pmel-17 molecule, as fitting the consensus sequence
               for peptides binding to human HLA-A2.1.  Pmel-17 was
               identified because of its homology to the Seq ID No. 14
               which has biologic activity.
           (D) OTHER INFORMATION:

(x) PUBLICATION INFORMATION:  Unpublished.

(xi) SEQUENCE DESCRIPTION: SEQ ID NO: 68:

Ser Leu Ala Val Val Ser Thr Gln Leu Ile
1               5                   10
```

(2) INFORMATION FOR SEQ ID NO:69:

(i) SEQUENCE CHARACTERISTICS:
       (A) LENGTH: 10
       (B) TYPE: amino acids
       (C) STRANDEDNESS: Not Relevant
       (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
       (A) CHROMOSOME/SEGMENT: 12
       (B) MAP POSITION:  unknown
       (C) UNITS:  unknown (ix) FEATURE:
       (A) NAME/KEY: SEQ ID NO: 69
       (B) LOCATION: Precursor protein Pmel-17 (PIR database,
           accession number A41234), residues 583-592.
       (C) IDENTIFICATION METHOD:  This peptide was identified, from
           the Pmel-17 molecule, as fitting the consensus sequence
           for peptides binding to human HLA-A2.1.  Pmel-17 was
           identified because of its homology to the Seq ID No. 14
           which has biologic activity.
       (D) OTHER INFORMATION:

(x) PUBLICATION INFORMATION:  Unpublished.

(xi) SEQUENCE DESCRIPTION: SEQ ID NO: 69:

Gln Leu Ile Met Pro Val Pro Gly Ile Leu
1               5                   10

(2) INFORMATION FOR SEQ ID NO: 70:

(i) SEQUENCE CHARACTERISTICS:
       (A) LENGTH: 10
       (B) TYPE: amino acids
       (C) STRANDEDNESS: Not Relevant
       (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
       (A) CHROMOSOME/SEGMENT: 12
       (B) MAP POSITION:  unknown
       (C) UNITS:  unknown (ix) FEATURE:
       (A) NAME/KEY: SEQ ID NO: 70
       (B) LOCATION: Precursor protein Pmel-17 (PIR database,
           accession number A41234), residues 609-618.
       (C) IDENTIFICATION METHOD:  This peptide was identified, from
           the Pmel-17 molecule, as fitting the consensus sequence
           for peptides binding to human HLA-A2.1.  Pmel-17 was
           identified because of its homology to the Seq ID No. 14

```
                    which has biologic activity.
             (D) OTHER INFORMATION:

(x) PUBLICATION INFORMATION:  Unpublished.

(xi) SEQUENCE DESCRIPTION: SEQ ID NO: 70:

Ile Leu Leu Val Leu Met Ala Val Val Leu
1               5                   10

(2) INFORMATION FOR SEQ ID NO: 71:

(i) SEQUENCE CHARACTERISTICS:
             (A) LENGTH: 10
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
             (A) CHROMOSOME/SEGMENT: 12
             (B) MAP POSITION:  unknown
             (C) UNITS:  unknown (ix) FEATURE:
             (A) NAME/KEY: SEQ ID NO 71
             (B) LOCATION: Precursor protein Pmel-17 (PIR database,
                 accession number A41234), residues 591-600.
             (C) IDENTIFICATION METHOD:  This peptide was identified, from
                 the Pmel-17 molecule, as fitting the consensus sequence
                 for peptides binding to human HLA-A2.1.  Pmel-17 was
                 identified because of its homology to the Seq ID No. 14
                 which has biologic activity.
             (D) OTHER INFORMATION:

(x) PUBLICATION INFORMATION:  Unpublished.

(xi) SEQUENCE DESCRIPTION: SEQ ID NO: 71:

Ile Leu Leu Thr Gly Gln Glu Ala Gly Leu
1               5                   10

(2) INFORMATION FOR SEQ ID NO: 72:

(i) SEQUENCE CHARACTERISTICS:
             (A) LENGTH: 10
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
             (A) CHROMOSOME/SEGMENT: 12
             (B) MAP POSITION:  unknown
             (C) UNITS:  unknown
```

```
    (ix) FEATURE:
         (A) NAME/KEY: SEQ ID NO: 72
         (B) LOCATION: Precursor protein Pmel-17 (PIR database,
             accession number A41234), residues 604-613.
         (C) IDENTIFICATION METHOD: This peptide was identified, from
             the Pmel-17 molecule, as fitting the consensus sequence
             for peptides binding to human HLA-A2.1. Pmel-17 was
             identified because of its homology to the Seq ID No. 14
             which has biologic activity.
         (D) OTHER INFORMATION:

(x) PUBLICATION INFORMATION: Unpublished.

(xi) SEQUENCE DESCRIPTION: SEQ ID NO: 72:

Pro Leu Ile Val Gly Ile Leu Leu Val Leu
1               5                   10

(2) INFORMATION FOR SEQ ID NO: 73:

(i) SEQUENCE CHARACTERISTICS:
         (A) LENGTH: 10
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
         (A) CHROMOSOME/SEGMENT: 12
         (B) MAP POSITION: unknown
         (C) UNITS: unknown (ix) FEATURE:
         (A) NAME/KEY: SEQ ID NO: 73
         (B) LOCATION: Precursor protein Pmel-17 (PIR database,
             accession number A41234), residues 610-619.
         (C) IDENTIFICATION METHOD: This peptide was identified, from
             the Pmel-17 molecule, as fitting the consensus sequence
             for peptides binding to human HLA-A2.1. Pmel-17 was
             identified because of its homology to the Seq ID No. 14
             which has biologic activity.
         (D) OTHER INFORMATION:

(x) PUBLICATION INFORMATION: Unpublished.

(xi) SEQUENCE DESCRIPTION: SEQ ID NO: 73:

Leu Leu Val Leu Met Ala Val Val Leu Ala
1               5                   10

(2) INFORMATION FOR SEQ ID NO: 74:

(i) SEQUENCE CHARACTERISTICS:
         (A) LENGTH: 10
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: internal fragment
```

(vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 74
             (B) LOCATION: Precursor protein Pmel-17 (PIR database,
                 accession number A41234), residues 612-621.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION:

(x) PUBLICATION INFORMATION: Unpublished.

(xi) SEQUENCE DESCRIPTION: SEQ ID NO: 74:

Val Leu Met Ala Val Val Leu Ala Ser Leu
1               5                   10

(2) INFORMATION FOR SEQ ID NO: 75:

(i) SEQUENCE CHARACTERISTICS:
             (A) LENGTH: 10
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 75
             (B) LOCATION: Precursor protein Pmel-17 (PIR database,
                 accession number A41234), residues 613-622.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION:

(x) PUBLICATION INFORMATION: Unpublished.

(xi) SEQUENCE DESCRIPTION: SEQ ID NO: 75:

Leu Met Ala Val Val Leu Ala Ser Leu Ile
1               5                   10

(2) INFORMATION FOR SEQ ID NO: 76:

(i) SEQUENCE CHARACTERISTICS:
             (A) LENGTH: 10
             (B) TYPE: amino acids
             (C) STRANDEDNESS: Not Relevant

```
              (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
              (A) CHROMOSOME/SEGMENT: 12
              (B) MAP POSITION:  unknown
              (C) UNITS:  unknown (ix) FEATURE:
              (A) NAME/KEY: SEQ ID NO: 76
              (B) LOCATION: Precursor protein Pmel-17 (PIR database,
                  accession number A41234), residues 636-645.
              (C) IDENTIFICATION METHOD:  This peptide was identified, from
                  the Pmel-17 molecule, as fitting the consensus sequence
                  for peptides binding to human HLA-A2.1.  Pmel-17 was
                  identified because of its homology to the Seq ID No. 14
                  which has biologic activity.
              (D) OTHER INFORMATION:

(x) PUBLICATION INFORMATION:  Unpublished.

(xi) SEQUENCE DESCRIPTION: SEQ ID NO: 76:

Gln Leu Pro His Ser Ser Ser His Trp Leu
1               5                   10

(2) INFORMATION FOR SEQ ID NO: 77:

(i) SEQUENCE CHARACTERISTICS:
              (A) LENGTH: 10
              (B) TYPE: amino acids
              (C) STRANDEDNESS: Not Relevant
              (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
              (A) CHROMOSOME/SEGMENT: 12
              (B) MAP POSITION:  unknown
              (C) UNITS:  unknown (ix) FEATURE:
              (A) NAME/KEY: SEQ ID NO: 77
              (B) LOCATION: Precursor protein Pmel-17 (PIR database,
                  accession number A41234), residues 96-105.
              (C) IDENTIFICATION METHOD:  This peptide was identified, from
                  the Pmel-17 molecule, as fitting the consensus sequence
                  for peptides binding to human HLA-A2.1.  Pmel-17 was
                  identified because of its homology to the Seq ID No. 14
                  which has biologic activity.
              (D) OTHER INFORMATION:

(x) PUBLICATION INFORMATION:  Unpublished.

(xi) SEQUENCE DESCRIPTION: SEQ ID NO: 77:

Val Leu Pro Asp Gly Gln Val Ile Trp Val
```

```
                            1               5                10
```

(2) INFORMATION FOR SEQ ID NO: 78:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO 78
        (B) LOCATION: Precursor protein Pmel-17 (PIR database,
            accession number A41234), residues 269-277.
        (C) IDENTIFICATION METHOD: This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:

(x) PUBLICATION INFORMATION: Unpublished.

(xi) SEQUENCE DESCRIPTION: SEQ ID NO: 78:

```
Leu Ile Ser Arg Ala Pro Val Val Thr
1               5
```

(2) INFORMATION FOR SEQ ID NO: 79:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO 79
        (B) LOCATION: Precursor protein Pmel-17 (PIR database,
            accession number A41234), residues 291-299.
        (C) IDENTIFICATION METHOD: This peptide was identified, from
            the Pmel-17 molecule, as fitting the consensus sequence
            for peptides binding to human HLA-A2.1. Pmel-17 was identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 79:

Val Leu Gln Ala Ala Ile Pro Leu Thr
1               5

(2) INFORMATION FOR SEQ ID NO: 80:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 80
            (B) LOCATION: Precursor protein Pmel-17 (PIR database,
                accession number A41234), residues 406-414.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:

(x) PUBLICATION INFORMATION: Unpublished.

(xi) SEQUENCE DESCRIPTION: SEQ ID NO: 80:

Ser Ile Val Val Leu Ser Gly Thr Thr
1               5

(2) INFORMATION FOR SEQ ID NO: 81:

(i) SEQUENCE CHARACTERISTICS:
            (A) LENGTH: 9
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown

```
            (C) UNITS:  unknown (ix) FEATURE:
           (A) NAME/KEY: SEQ ID NO: 81
           (B) LOCATION: Precursor protein Pmel-17 (PIR database,
               accession number A41234), residues 443-451.
           (C) IDENTIFICATION METHOD:  This peptide was identified, from
               the Pmel-17 molecule, as fitting the consensus sequence
               for peptides binding to human HLA-A2.1.  Pmel-17 was
               identified because of its homology to the Seq ID No. 14
               which has biologic activity.
           (D) OTHER INFORMATION:

(x) PUBLICATION INFORMATION:  Unpublished.

(xi) SEQUENCE DESCRIPTION: SEQ ID NO: 81:

Ser Ile Met Ser Thr Glu Ser Ile Thr
1               5

(2) INFORMATION FOR SEQ ID NO: 82:

(i) SEQUENCE CHARACTERISTICS:
           (A) LENGTH: 9
           (B) TYPE: amino acids
           (C) STRANDEDNESS: Not Relevant
           (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
           (A) CHROMOSOME/SEGMENT: 12
           (B) MAP POSITION:  unknown
           (C) UNITS:  unknown (ix) FEATURE:
           (A) NAME/KEY: SEQ ID NO: 82
           (B) LOCATION: Precursor protein Pmel-17 (PIR database,
               accession number A41234), residues 453-461.
           (C) IDENTIFICATION METHOD:  This peptide was identified, from
               the Pmel-17 molecule, as fitting the consensus sequence
               for peptides binding to human HLA-A2.1.  Pmel-17 was
               identified because of its homology to the Seq ID No. 14
               which has biologic activity.
           (D) OTHER INFORMATION:

(x) PUBLICATION INFORMATION:  Unpublished.

(xi) SEQUENCE DESCRIPTION: SEQ ID NO: 82:

Ser Leu Gly Pro Leu Leu Asp Gly Thr
1               5

(2) INFORMATION FOR SEQ ID NO: 83:

(i) SEQUENCE CHARACTERISTICS:
           (A) LENGTH: 11
           (B) TYPE: amino acids
           (C) STRANDEDNESS: Not Relevant
           (D) TOPOLOGY: linear (ii) MOLECULE TYPE: peptide (iii) HYPOTHETICAL: no (iv) ANTI-SENSE: no
```

```
        (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 83
             (B) LOCATION: Precursor protein Pmel-17 (PIR database,
                 accession number A41234), residues 9-19.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION:

(x) PUBLICATION INFORMATION: Unpublished.

(xi) SEQUENCE DESCRIPTION: SEQ ID NO: 83:

Leu Leu His Leu Ala Val Ile Gly Ala Leu Leu
  1               5                  10

(2) INFORMATION FOR SEQ ID NO: 84:

(i) SEQUENCE CHARACTERISTICS:
             (A) LENGTH: 11
             (B) TYPE: amino acids
             (C) STRANDEDNESS: Not Relevant
             (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
             (A) CHROMOSOME/SEGMENT: 12
             (B) MAP POSITION: unknown
             (C) UNITS: unknown (ix) FEATURE:
             (A) NAME/KEY: SEQ ID NO: 84
             (B) LOCATION: Precursor protein Pmel-17 (PIR database,
                 accession number A41234), residues 8-18.
             (C) IDENTIFICATION METHOD: This peptide was identified, from
                 the Pmel-17 molecule, as fitting the consensus sequence
                 for peptides binding to human HLA-A2.1. Pmel-17 was
                 identified because of its homology to the Seq ID No. 14
                 which has biologic activity.
             (D) OTHER INFORMATION:

(x) PUBLICATION INFORMATION: Unpublished.

(xi) SEQUENCE DESCRIPTION: SEQ ID NO: 84:

Cys Leu Leu His Leu Ala Val Ile Gly Ala Leu
  1               5                  10

(2) INFORMATION FOR SEQ ID NO: 85:

(i) SEQUENCE CHARACTERISTICS:
             (A) LENGTH: 11
             (B) TYPE: amino acids
```

```
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 85
            (B) LOCATION: Precursor protein Pmel-17 (PIR database,
                accession number A41234), residues 11-21.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:

(x) PUBLICATION INFORMATION:  Unpublished.

(xi) SEQUENCE DESCRIPTION: SEQ ID NO: 85:

His Leu Ala Val Ile Gly Ala Leu Leu Ala Val
1               5                   10

(2) INFORMATION FOR SEQ ID NO: 86:

(i) SEQUENCE CHARACTERISTICS:
            (A) LENGTH: 11
            (B) TYPE: amino acids
            (C) STRANDEDNESS: Not Relevant
            (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE:  not applicable (viii) POSITION IN GENOME:
            (A) CHROMOSOME/SEGMENT: 12
            (B) MAP POSITION:  unknown
            (C) UNITS:  unknown (ix) FEATURE:
            (A) NAME/KEY: SEQ ID NO: 86
            (B) LOCATION: Precursor protein Pmel-17 (PIR database,
                accession number A41234), residues 2-12.
            (C) IDENTIFICATION METHOD:  This peptide was identified, from
                the Pmel-17 molecule, as fitting the consensus sequence
                for peptides binding to human HLA-A2.1.  Pmel-17 was
                identified because of its homology to the Seq ID No. 14
                which has biologic activity.
            (D) OTHER INFORMATION:

(x) PUBLICATION INFORMATION:  Unpublished.

(xi) SEQUENCE DESCRIPTION: SEQ ID NO: 86:
```

```
Asp Leu Val Leu Lys Arg Cys Leu Leu His Leu
1               5                   10
```

(2) INFORMATION FOR SEQ ID NO: 87:

(i) SEQUENCE CHARACTERISTICS:
        (A) LENGTH: 11
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: internal fragment (vi) ORIGINAL SOURCE: not applicable (vii) IMMEDIATE SOURCE: not applicable (viii) POSITION IN GENOME:
        (A) CHROMOSOME/SEGMENT: 12
        (B) MAP POSITION: unknown
        (C) UNITS: unknown (ix) FEATURE:
        (A) NAME/KEY: SEQ ID NO: 87
        (B) LOCATION: Precursor protein Pmel-17 (PIR database,
            accession number A41234), residues 4-14.
        (C) IDENTIFICATION METHOD: This peptide was identified, from
            the Pmel-17 molecule, as fitting the consensus sequence
            for peptides binding to human HLA-A2.1. Pmel-17 was
            identified because of its homology to the Seq ID No. 14
            which has biologic activity.
        (D) OTHER INFORMATION:

(x) PUBLICATION INFORMATION: Unpublished.

(xi) SEQUENCE DESCRIPTION: SEQ ID NO: 87:

```
Val Leu Lys Arg Cys Leu Leu His Leu Ala Val
1               5                   10
```

(2) INFORMATION FOR SEQ ID NO: 88:

(i) SEQUENCE CHARACTERISTICS:
        (A) LENGTH: 9
        (B) TYPE: amino acids
        (C) STRANDEDNESS: Not Relevant
        (D) TOPOLOGY: linear (ii) MOLECULE TYPE: peptide (iii) HYPOTHETICAL: no (iv) ANTI-SENSE: no (v) FRAGMENT TYPE: not applicable (vi) ORIGINAL SOURCE:
        (A) ORGANISM: human
        (B) STRAIN:
        (C) INDIVIDUAL ISOLATE:
        (D) DEVELOPMENTAL STAGE: adult
        (E) HAPLOTYPE:
        (F) TISSUE TYPE: melanoma
        (G) CELL TYPE:
        (H) CELL LINE: DM6, gift from Duke Univerisity
        (I) ORGANELLE:

(vii) IMMEDIATE SOURCE: not applicable (viii) POSITION IN GENOME: unknown

```
    (ix) FEATURE:
         (A) NAME/KEY: SEQ ID NO: 88 (Peptide 864)
         (B) LOCATION: not applicable
         (C) IDENTIFICATION METHOD: This peptide was identified
             directly by tandem mass spectrometric analysis of
             peptides eluted from HLA-A2.1 molecules purified from the
             human melanoma cell line, DM6.
         (D) OTHER INFORMATION: This peptide was synthesized, but did
             not reconstitute an epitope for these CTL. A database
             search identified no homologous matches to known
             proteins.

(x) PUBLICATION INFORMATION:
         (A) AUTHORS: Cox, AL
             Skipper, J
             Chen, Y
             Henderson, R
             Darrow, TL
             Shabanowitz, J
             Engelhard, VH
             Hunt, DF
             Slingluff, CL.
         (B) TITLE: Identification of a Peptide Recognized by Five
             Melan oma-specific Human Cytotoxic T-Cell Lines
         (C) JOURNAL: Science
         (D) VOLUME: Submitted ( A copy of the manuscript is enclosed
             with this patent application.)
         (E) ISSUE:
         (F) PAGES:
         (G) DATE:

(xi) SEQUENCE DESCRIPTION: SEQ ID NO: 88:

Ser Met Ala Pro Gly Asn Thr Ser Val
1               5

(2) INFORMATION FOR SEQ ID NO: 89:

(i) SEQUENCE CHARACTERISTICS:
         (A) LENGTH: 9
         (B) TYPE: amino acids
         (C) STRANDEDNESS: Not Relevant
         (D) TOPOLOGY: linear (ii) MOLECULE TYPE: peptide (iii) HYPOTHETICAL: no (iv) ANTI-SENSE: no (v) FRAGMENT TYPE: not applicable (vi) ORIGINAL SOURCE:
         (A) ORGANISM: human
         (B) STRAIN:
         (C) INDIVIDUAL ISOLATE:
         (D) DEVELOPMENTAL STAGE: adult
         (E) HAPLOTYPE:
         (F) TISSUE TYPE: melanoma
         (G) CELL TYPE:
         (H) CELL LINE: DM6, gift from Duke University
         (I) ORGANELLE:

(vii) IMMEDIATE SOURCE: not applicable (viii) POSITION IN GENOME:
         (A) CHROMOSOME/SEGMENT:
         (B) MAP POSITION:
         (C) UNITS:

(ix) FEATURE:
         (A) NAME/KEY: SEQ ID NO: 89 (peptide 1046)
         (B) LOCATION: Cofilin residues 83-91.
         (C) IDENTIFICATION METHOD: This peptide was identified
             directly by tandem mass spectrometric analysis of
             peptides eluted from HLA-A2.1 molecules purified from the
             human melanoma cell line, DM6.
         (D) OTHER INFORMATION: This peptide was synthesized, but did
``` re constitute an epitope for these CTL. A database
search identified homo logy with cofilin, an actin-
modulating protein that is ubiquitously expressed in
mammalian cells. The sequence, when Xaa is Leu, corres
ponds to residues 83-91 of the cofilin protein (PIR
S12632;ref: Ogawa, K. et al. Nucleic Acids Res. 18: 7169
(1990). Wherein Xaa = Leu or Ile.

(x) PUBLICATION INFORMATION: Unpublished.

(xi) SEQUENCE DESCRIPTION: SEQ ID NO: 89:

Ala Xaa Tyr Asp Ala Thr Tyr Glu Thr
1               5

(2) INFORMATION FOR SEQ ID NO: 90:

(i) SEQUENCE CHARACTERISTICS:
      (A) LENGTH: 27
      (B) TYPE: nucleic acids
      (C) STRANDEDNESS: single
      (D) TOPOLOGY: linear (ii) MOLECULE TYPE: cDNA (iii) HYPOTHETICAL: no (iv) ANTI-SENSE: no (v) FRAGMENT TYPE: internal fragment (vi) ORIGINAL SOURCE:
      (A) ORGANISM: human
      (B) STRAIN:
      (C) INDIVIDUAL ISOLATE:
      (D) DEVELOPMENTAL STAGE: adult
      (E) HAPLOTYPE:
      (F) TISSUE TYPE: melanoma
      (G) CELL TYPE:
      (H) CELL LINE: DM6, a gift from Duke University
      (I) ORGANELLE:

(vii) IMMEDIATE SOURCE: not applicable
      (A) LIBRARY:
      (B) CLONE:

(viii) POSITION IN GENOME:
      (A) CHROMOSOME/SEGMENT: chromosome 12
      (B) MAP POSITION:
      (C) UNITS:

(ix) FEATURE:
      (A) NAME/KEY: SEQ ID NO: 90 (946 gene)
      (B) LOCATION: See identification method.
      (C) IDENTIFICATION METHOD: The protein data bank was searched
         for homology to the peptide directly identified as
         sequence ID No. 14. Homology to the Pmel-17 protein was
         identified at residues 849-875. The genetic sequence
         encoding those residues was identified from the gene bank
         and is listed above.
      (D) OTHER INFORMATION: The peptide encoded by this gene
         sequence is biologically very active as an epitope for
         melanoma-specific cyto-toxic T lymphocytes.

(x) PUBLICATION INFORMATION: None.

(xi) SEQUENCE DESCRIPTION: SEQ ID NO: 90:

TAC CTG GAG CCT GGC CCA GTC ACT GCC                                  27

(2) INFORMATION FOR SEQ ID NO: 91:

(i) SEQUENCE CHARACTERISTICS:
      (A) LENGTH: 2131
      (B) TYPE: nucleic acids
      (C) STRANDEDNESS: single
      (D) TOPOLOGY: linear (ii) MOLECULE TYPE: cDNA (iii) HYPOTHETICAL: no (iv) ANTI-SENSE: no (v) FRAGMENT TYPE: complete gene (vi) ORIGINAL SOURCE:
             (A) ORGANISM: human
             (B) STRAIN:
             (C) INDIVIDUAL ISOLATE:
             (D) DEVELOPMENTAL STAGE:
             (E) HAPLOTYPE:
             (F) TISSUE TYPE: melanocyte
             (G) CELL TYPE:
             (H) CELL LINE:
             (I) ORGANELLE:

(vii) IMMEDIATE SOURCE:
             (A) LIBRARY:
             (B) CLONE:

(viii) POSITION IN GENOME:
             (A) CHROMOSOME/SEGMENT: chromosome 12
             (B) MAP POSITION:
             (C) UNITS:

(ix) FEATURE:
             (A) NAME/KEY: SEQ ID NO: 91
             (B) LOCATION:  gene for Pmel-17 (accession number M77348)
             (C) IDENTIFICATION METHOD: This gene encodes the protein
                 Pmel-17, which was found to contain Seq ID No. 14, which
                 has biologic activity as an epitope for melanoma-specific
                 cytotoxic T lymphocytes.
             (D) OTHER INFORMATION:  This sequence has previously been des-
                 cribed.  We are claiming its use in a tumor vaccine for
                 the prevention and treatment of melanoma.

(x) PUBLICATION INFORMATION:
             (A) AUTHORS: Kwon, B. S. et al.
             (B) TITLE:  A Melanocyte Specific Gene, Pmel-17, Mapped Near
                 the Silver Coat Color Locus on Mouse Chromosone 10 and is
                 in A Syntenic Region on Human Chromosone 12
             (C) JOURNAL:  Proc. Natl. Acad. Sci. USA
             (D) VOLUME: 88
             (E) ISSUE:
             (F) PAGES: 9228:9232
             (G) DATE: 1991

(xi) SEQUENCE DESCRIPTION: SEQ ID NO: 91:

```
GGAAGAACAC AATGGATCTG GTGCTAAAAA GATGCCTTCT TCATTTGGCT GTGATAGGTG      60

CTTTGCTGGC TGTGGGGGCT ACAAAAGTAC CCAGAAACCA GGACTGGCTT GGTGTCTCAA     120

GGCAACTCAG AACCAAAGCC TGGAACAGGC AGCTGTATCC AGAGTGGACA GAAGCCCAGA     180

GACTTGACTG CTGGAGAGGT GGTCAAGTGT CCCTCAAGGT CAGTAATGAT GGGCCTACAC     240

TGATTGGTGC AAATGCCTCC TTCTCTATTG CCTTGAACTT CCCTGGAAGC CAAAAGGTAT     300

TGCCAGATGG GCAGGTTATC TGGGTCAACA ATACCATCAT CAATGGGAGC CAGGTGTGGG     360

GAGGACAGCC AGTGTATCCC AGGAAACTG ACGATGCCTG CATCTTCCCT GATGGTGGAC      420

CTTGCCCATC TGGCTCTTGG TCTCAGAAGA GAAGCTTTGT TTATGTCTGG AAGACCTGGG     480

GCCAATACTG GCAAGTTCTA GGGGGCCCAG TGTCTGGGCT GAGCATTGGG ACAGGCAGGG     540

CAATGCTGGG CACACACACC ATGGAAGTGA CTGTCTACCA TCGCCGGGGA TCCCGGAGCT     600

ATGTGCCTCT TGCTCATTCC AGCTCAGCCT TCACCATTAC TGACCAGGTG CCTTTCTCCG     660

TGAGCGTGTC CCAGTTGCGG GCCTTGGATG GAGGGAACAA GCACTTCCTG AGAAATCAGC     720

CTCTGACCTT TGCCCTCCAG CTCCATGACC CTAGTGGCTA TCTGGCTGAA GCTGACCTCT     780
```

-continued

```
CCTACACCTG GGACTTTGGA GACAGTAGTG GAACCCTGAT CTCTCGGGCA CCTGTGGTCA        840

CTCATACTTA CCTGGAGCCT GGCCCAGTCA CTGCCCAGGT GGTCCTGCAG GCTGCCATTC        900

CTCTCACCTC CTGTGGCTCC TCCCCAGTTC CAGGCACCAC AGATGGGCAC AGGCCAACTG        960

CAGAGGCCCC TAACACCACA GCTGGCCAAG TGCCTACTAC AGAAGTTGTG GGTACTACAC       1020

CTGGTCAGGC GCCAACTGCA GAGCCCTCTG GAACCACATC TGTGCAGGTG CCAACCACTG       1080

AAGTCATAAG CACTGCACCT GTGCAGATGC CAACTGCAGA GAGCACAGGT ATGACACCTG       1140

AGAAGGTGCC AGTTTCAGAG GTCATGGGTA CCACACTGGC AGAGATGTCA ACTCCAGAGG       1200

CTACAGGTAT GACACCTGCA GAGGTATCAA TTGTGGTGCT TTCTGGAACC ACAGCTGCAC       1260

AGGTAACAAC TACAGAGTGG GTGGAGACCA CAGCTAGAGA GCTACCTATC CCTGAGCCTG       1320

AAGGTCCAGA TGCCAGCTCA ATCATGTCTA CGGAAAGTAT TACAGGTTCC CTGGGCCCCC       1380

TGCTGGATGG TACAGCCACC TTAAGGCTGG TGAAGAGACA AGTCCCCCTG GATTGTGTTC       1440

TGTATCGATA TGGTTCCTTT TCCGTCACCC TGGACATTGT CCAGGGTATT GAAAGTGCCG       1500

AGATCCTGCA GGCTGTGCCG TCCGGTGAGG GGGATGCATT TGAGCTGACT GTGTCCTGCC       1560

AAGGCGGGCT GCCCAAGGAA GCCTGCATGG AGATCTCATC GCCAGGGTGC CAGCCCCCTG       1620

CCCAGCGGCT GTGCCAGCCT GTGCTACCCA GCCCAGCCTG CCAGCTGGTT CTGCACCAGA       1680

TACTGAAGGG TGGCTCGGGG ACATACTGCC TCAATGTGTC TCTGGCTGAT ACCAACAGCC       1740

TGGCAGTGGT CAGCACCCAG CTTATCATGC CTGTGCCTGG GATTCTTCTC ACAGGTCAAG       1800

AAGCAGGCCT TGGGCAGGTT CGGCTGATCG TGGGCATCTT GCTGGTGTTG ATGGCTGTGG       1860

TCCTTGCATC TCTGATATAT AGGCGCAGAC TTATGAAGCA AGACTTCTCC GTACCCCAGT       1920

TGCCACATAG CAGCAGTCAC TGGCTGCGTC TACCCCGCAT CTTCTGCTCT TGTCCCATTG       1980

GTGAGAATAG CCCCCTCCTC AGTGGGCAGC AGGTCTGAGT ACTCTCATAT GATGCTGTGA       2040

TTTTCCTGGA GTTGACAGAA ACACCTATAT TTCCCCCAGT CTTCCCTGGG AGACTACTAT       2100

TAACTGAAAT AAATACTCAG AGCCTGAAAA A                                     2131
```

(2) INFORMATION FOR SEQ ID NO: 92:

(i) SEQUENCE CHARACTERISTICS:
        (A) LENGTH: 27
        (B) TYPE: nucleic acids
        (C) STRANDEDNESS: single
        (D) TOPOLOGY: linear (ii) MOLECULE TYPE: cDNA (iii) HYPOTHETICAL: yes (iv) ANTI-SENSE: no (v) FRAGMENT TYPE: internal fragment (vi) ORIGINAL SOURCE: not applicable
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE: not applicable
        (A) LIBRARY:
        (B) CLONE:

(viii) POSITION IN GENOME: not applicable

```
            (A) CHROMOSOME/SEGMENT:
            (B) MAP POSITION:
            (C) UNITS:

(ix) FEATURE:
            (A) NAME/KEY: SEQ ID NO: 92 (YMDGTMSQV gene)
            (B) LOCATION: not applicable
            (C) IDENTIFICATION METHOD:  The peptide YMDGTMSQV was directly
                identified on HLA-A2.1 molecules of a human melanoma. We
                derived a gene sequence encoding YMDGTMSQV that shares
                all the nucleic acid residues 2365-2391 of the
                tyrosinase gene, which encode YMNGTMSQV, except for a
                change of A to G at residue 2371, encoding D (Asp) at
                position 3 of the peptide, instead of N (Asn).
            (D) OTHER INFORMATION: The reference for the tyrosinase
                sequence is Genomics 9, 435-445, 1991 Giebel, LB et al.
                Accession number for the tyrosine sequence is A38444 in
                the PIR databank.

(x) PUBLICATION INFORMATION: not published.

(xi) SEQUENCE DESCRIPTION: SEQ ID NO: 92:

TAT ATG GAT GGA ACA ATG TCC CAG GTA                                     27

(2) INFORMATION FOR SEQ ID NO:93:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: /note= "Xaa is Ile or Leu"

(xi) SEQUENCE DESCRIPTION: SEQ ID NO:93:

Tyr Xaa Glu Pro Gly Pro Val Thr Ala
1               5

(2) INFORMATION FOR SEQ ID NO:94:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:94:

Ala Leu Trp Gly Phe Phe Pro Val Leu
1               5

(2) INFORMATION FOR SEQ ID NO:95:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:95:

Ala Pro Arg Thr Val Ala Leu Thr Ala
1               5

(2) INFORMATION FOR SEQ ID NO:96:
```

```
        (i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:96:

Tyr Met Asn Gly Thr Met Ser Gln Val
1               5

(2) INFORMATION FOR SEQ ID NO:97:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:97:

Phe Leu Pro Ser Asp Tyr Phe Pro Ser Val
1               5                   10
```

What is claimed is:

1. A melanoma-specific immunogen in isolated form which is a peptide with a length of 9 to about 15 residues and which comprises the amino acid sequence of peptide 1030, SEQ ID NO:9, wherein said immunogen elicits a melanoma-specific, HLA-A2-restricted CTL response.

2. The immunogen of claim 1 wherein the length of said immunogen is 9–11 residues.

3. The immunogen of claim 1 which is identical to peptide 1030, SEQ ID NO:9.

4. A method of treating a patient for melanoma which comprises administering a therapeutically effective amount of the melanoma-specific immunogen of claim 1, thereby achieving a therapeutic effect.

5. A method of eliciting a melanoma specific CTL response which comprises administering a response-eliciting amount of the melanoma-specific immunogen of claim 1.

6. A method of treating a patient tor melanoma which comprises administering a therapeutically effective amount of the melanoma-specific immunogen of claim 3 thereby achieving a therapeutic effect.

7. A methed of eliciting a melanomna specific CTL response which comprises administering a response-eliciting amount or the melanoma-specific immunogen of claim 3.

8. A melanoma-specific immunogen in isolated form, which is a peptide with a length of 9 to about 15 amino acid residues, which comprises a single melanoma-specific CTL epitope, which comprises an amino acid sequence identical to peptide 946I (SEQ. ID. NO.:39), wherein said CTL epitope is an HLA-A2 restricted CTL epitope, and wherein said immunogen elicits a melanoma-specific, HLA-A2-restricted CTL response.

9. The immunogen of claim 8 where the length of said immunogen is 9–11 residues.

10. The immunogen of claim 8 which is identical to said epitope.

11. A method of treating a patient for melonoma which comprises administering a therapeutically effective amount of the melanoma-specific immunogen of claim 10.

12. A method of eliciting a melanoma specific CTL response which comprises administering a response-eliciting amount of the melanoma-specific immunogen of claim 10.

* * * * *